United States Patent
Andrews et al.

(10) Patent No.: US 7,655,652 B2
(45) Date of Patent: Feb. 2, 2010

(54) IMIDAZOLO-5-YL-2-ANILINOPYRIMIDINES AS AGENTS FOR THE INHIBITION OF CELL PROLIFERATION

(75) Inventors: David Michael Andrews, Macclesfield (GB); Maurice Raymond Finlay, Macclesfield (GB); Clive Green, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 447 days.

(21) Appl. No.: 10/586,954

(22) PCT Filed: Jan. 31, 2005

(86) PCT No.: PCT/GB2005/000303

§ 371 (c)(1), (2), (4) Date: Jul. 25, 2006

(87) PCT Pub. No.: WO2005/075461

PCT Pub. Date: Aug. 18, 2005

(65) Prior Publication Data

US 2007/0161615 A1    Jul. 12, 2007

(30) Foreign Application Priority Data

Feb. 3, 2004   (GB) ................... 0402277.8
May 28, 2004   (GB) ................... 0411998.8

(51) Int. Cl.
  C07D 403/04   (2006.01)
  A61K 31/505   (2006.01)
(52) U.S. Cl. .................. 514/235.8; 514/252.19; 514/275; 544/122; 544/295; 544/331
(58) Field of Classification Search ............... 544/122, 544/295, 331; 514/235.8, 252.19, 275
See application file for complete search history.

(56) References Cited

U.S. PATENT DOCUMENTS

| | | | |
|---|---|---|---|
| 4,983,608 A | 1/1991 | Effland et al. |
| 5,516,775 A | 5/1996 | Zimmermann et al. |
| 5,521,184 A | 5/1996 | Zimmermann |
| 5,610,303 A | 3/1997 | Kimura et al. |
| 5,739,143 A | 4/1998 | Adams et al. |
| 5,859,041 A | 1/1999 | Liverton et al. |
| 6,835,726 B2 | 12/2004 | Cushing et al. |
| 2003/0144303 A1 | 7/2003 | Hawley et al. |
| 2003/0191307 A1 | 10/2003 | Blumenkopf et al. |
| 2006/0079543 A1 | 4/2006 | Sum et al. |

FOREIGN PATENT DOCUMENTS

| | | |
|---|---|---|
| CA | 2231765 | 9/1998 |
| EP | 0135472 | 1/1989 |
| EP | 0363002 | 6/1994 |
| EP | 0379806 | 4/1996 |
| EP | 1056742 | 7/2003 |
| EP | 0945443 | 8/2003 |
| HU | 220630 | 3/2002 |
| WO | WO 91/18887 | 12/1991 |
| WO | WO 92/20642 | 11/1992 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/15952 | 6/1995 |
| WO | WO 96/05177 | 2/1996 |
| WO | WO 96/28427 | 9/1996 |
| WO | WO 96/40143 | 12/1996 |
| WO | WO 97/19065 | 5/1997 |
| WO | WO 97/35856 | 10/1997 |
| WO | WO 97/40017 | 10/1997 |
| WO | WO 97/44326 | 11/1997 |
| WO | WO 9747618 | 12/1997 |
| WO | WO 98/11095 | 3/1998 |
| WO | WO 98/16230 | 4/1998 |
| WO | WO 98/18782 | 5/1998 |
| WO | WO 98/25619 | 6/1998 |
| WO | WO 98/33798 | 8/1998 |
| WO | WO 98/41512 | 9/1998 |
| WO | WO 98/54093 | 12/1998 |
| WO | WO 98/56788 | 12/1998 |
| WO | WO 99/01136 | 1/1999 |
| WO | WO 99/18096 | 4/1999 |
| WO | WO 99/18942 | 4/1999 |
| WO | WO 99/31073 | 6/1999 |

(Continued)

OTHER PUBLICATIONS

Banker et al., Prodrugs, Modern Pharmaceutics, Third Edition, Revised and Expanded, pp. 451 and 596.*

(Continued)

*Primary Examiner*—Deepak Rao
(74) *Attorney, Agent, or Firm*—Morgan, Lewis & Bockius LLP

(57) ABSTRACT

Compounds of the formula (I), wherein variable groups are as defined within and a pharmaceutically acceptable salts and in vivo hydrolysable esters are described. Also described are processes for their preparation and their use as medicaments, particularly medicaments for producing a cell cycle inhibitory (anti cell proliferation) effect in a warm blooded animal, such as man.

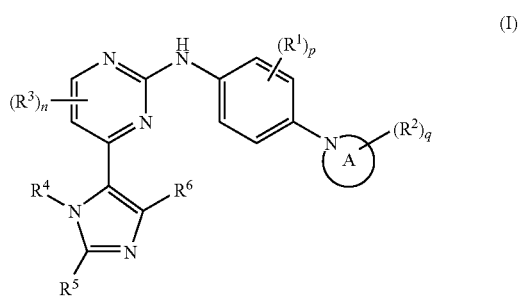

15 Claims, No Drawings

FOREIGN PATENT DOCUMENTS

| | | |
|---|---|---|
| WO | WO 99/32121 | 7/1999 |
| WO | WO 99/41253 | 8/1999 |
| WO | WO 99/50250 | 10/1999 |
| WO | WO 99/50251 | 10/1999 |
| WO | WO 00/12485 | 3/2000 |
| WO | WO 00/12486 | 3/2000 |
| WO | WO 00/17202 | 3/2000 |
| WO | WO 00/17203 | 3/2000 |
| WO | WO 00/21926 | 4/2000 |
| WO | WO 00/25780 | 5/2000 |
| WO | WO 00/26209 | 5/2000 |
| WO | WO 00/39101 | 6/2000 |
| WO | WO 00/44750 | 8/2000 |
| WO | WO 00/49018 | 8/2000 |
| WO | WO 00/53595 | 9/2000 |
| WO | WO 00/55161 | 9/2000 |
| WO | WO 00/59892 | 10/2000 |
| WO | WO 00/78731 | 12/2000 |
| WO | WO 01/14375 | 3/2001 |
| WO | WO 01/29009 | 4/2001 |
| WO | WO 01/30778 | 5/2001 |
| WO | WO 01/37835 | 5/2001 |
| WO | WO 01/47897 | 7/2001 |
| WO | WO 01/47921 | 7/2001 |
| WO | WO 01/60816 | 8/2001 |
| WO | WO 01/64653 | 9/2001 |
| WO | WO 01/64654 | 9/2001 |
| WO | WO 01/64655 | 9/2001 |
| WO | WO 01/64656 | 9/2001 |
| WO | WO 01/72717 | 10/2001 |
| WO | WO 02/04429 | 1/2002 |
| WO | WO 02/20512 A | 3/2002 |
| WO | WO 02/46170 | 6/2002 |
| WO | WO 02/46171 | 6/2002 |
| WO | WO 02/65979 | 8/2002 |
| WO | WO 02/066480 A | 8/2002 |
| WO | WO 02/66481 | 8/2002 |
| WO | WO 02/92573 | 11/2002 |
| WO | WO 02/96887 | 12/2002 |
| WO | WO 02/96888 | 12/2002 |
| WO | WO 03/007955 | 1/2003 |
| WO | WO 03/011837 | 2/2003 |
| WO | WO 03/029249 | 4/2003 |
| WO | WO 03/031446 | 4/2003 |
| WO | WO 03/037891 | 5/2003 |
| WO | WO 03/076433 | 9/2003 |
| WO | WO 03/076434 | 9/2003 |
| WO | WO 03/076435 | 9/2003 |
| WO | WO 03/076436 | 9/2003 |
| WO | WO 2004/005282 | 1/2004 |
| WO | WO 2004/005283 | 1/2004 |
| WO | WO 2004/043467 | 5/2004 |
| WO | WO 2004/043953 | 5/2004 |
| WO | WO 2004/087698 | 10/2004 |
| WO | WO 2004/087699 | 10/2004 |
| WO | WO 2004/101549 | 11/2004 |
| WO | WO 2004/101564 | 11/2004 |
| WO | WO 2005/012298 | 2/2005 |
| WO | WO 2005/037800 | 4/2005 |
| WO | WO 2005/068452 | 7/2005 |
| WO | WO 2005/075468 | 8/2005 |
| WO | WO 2005/113550 | 12/2005 |
| WO | WO 2005/116025 | 12/2005 |
| WO | WO 2006/034872 | 4/2006 |
| WO | WO 2006/044509 | 4/2006 |
| WO | WO 2006/050076 | 5/2006 |
| WO | WO 2006/064251 | 6/2006 |
| WO | WO 2006/075152 | 7/2006 |
| WO | WO 2006/095159 | 9/2006 |
| WO | WO 2007/015064 | 2/2007 |
| WO | WO 2007/036732 | 4/2007 |
| WO | WO 2007/040436 | 4/2007 |
| WO | WO 2007/040440 | 4/2007 |
| WO | WO 2007/138268 | 12/2007 |
| WO | WO 2007/138277 | 12/2007 |
| WO | WO 2007/148070 | 12/2007 |
| WO | WO 2008/002244 | 1/2008 |
| WO | WO 2008/002245 | 1/2008 |

OTHER PUBLICATIONS

Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Traxler, Protein tyrosine kinase inhibitors in cancer treatment, Expert Opinion on Therapeutic Patents, 7(6), pp. 571-588, 1997.*
Lu Valle et al., Cell Cycle Control in Growth Plate Chondrocytes, Frontiers in Biosciences 5, d493-503, May 2000.*
Fiziol Akt Veshchestva 7:68-72 (1975) (Translation enclosed).
Blain, S. et al. "Differential interaction of the cyclin-dependent kinase (Cdk) inhibitor p27$^{Kip1}$ with cyclin A-Cdk2 and cyclin D2-Cdk4" The Journal of Biological Chemistry, 1997, vol. 272, No. 41, pp. 25863-25872.
Boschelli, D. et al. "Synthesis and tyrosine kinase inhibitory activity of a series of 2-amino-8H-pyrido[2,3-d]pyrimidines: identification of potent, selective platelet-derived growth factor receptor tyrosine kinase inhibitors" J. Med. Chem., 1998, vol. 41, pp. 4365-4377.
Deady L. et al. "Reactions of some quinazoline compounds with ethoxymethylenemalonic acid derivatives" J. Heterocyclic Chem., 1989, vol. 26, pp. 161-168.
El-Kerdawy, M. et al. "2,4-Bis(substituted)-5-nitropyrimidines of expected diuretic action" Egypt. J. Chem., 1986, 29, vol. 2, No. 2, pp. 247-251.
Fiziol Alct Veshchestva, 1975, 7, pp. 68-72.
Ghosh, D. et al. "2,4-Bis(arylamino)-5-methylpyrimidines as antimicrobial agents" J. Med. Chem., 1967, vol. 10, pp. 974-975.
Ghosh, D., "2,4-Bis(arylamino)-6-methyl pyrimidines as antimicrobial agents" Chemical Abstracts, 1981, vol. 95, No. 11, Columbus, Ohio, US; Abstract No. 97712f; pp. 648; XP002109184 abstract & J. Indian Chem. Soc., 1981, vol. 58, No. 5, pp. 512-513, India.
Schmidt, H. et al. "A convenient synthesis of 2-substituted 4-amino-5-pyrimidinecarbonitriles" J. Heterocyclic Chem., 1987, vol. 24, pp. 1305-1307.
Simone, J. "Oncology: introduction" Bennett, J. Textbook of Medicine, 20th Edition, vol. 1, 1996, pp. 1004-1010.
Volin, M. et al. "Cell cycle implications in the pathogenesis of rheumatoid arthritis" Frontiers in Bioscience, 2000, 5, d594-601.
Zimmermann, J. et al. "Phenylamino-pyrimidine (PAP) derivatives: a new class of potent and selective inhibitors of protein kinase C (PKC)" Arch. Pharm. Pharm. Med. Chem. 1996, 329 (7), pp. 371-376.
Anderson et al, "Imidazo[1,2-a]pyridines: A potent and selective class of cyclin-dependent kinase inhibitors identified through structure-based hybridisation" Bioorganic & Medicinal Chemistry Letters 13(18):3021-3026 (2003).
Byth et al. "Imidazo[1,2-a]pyridines. Part 2: SAR and optimisation of a potent and selective class of cyclin-dependent kinase inhibitors" Bioorganic & Medicinal Chemistry Letters 14(9):2245-2248 (2004).
Byth et al. "Imidazo[1,2-b]pyridazines: a potent and selective class of cyclin-dependent kinase inhibitors" Bioorganic & Medicinal Chemistry Letters 14(9): 2249-2252 (2004).
Byth et al. "The Cellular phenotype of AZ703, a novel selective imidazo[1,2-a]pyridine cyclin-dependent kinase inhibitor" Molecular Cancer Therapeutics 5(3):655-664 (2006).

* cited by examiner

IMIDAZOLO-5-YL-2-ANILINOPYRIMIDINES AS AGENTS FOR THE INHIBITION OF CELL PROLIFERATION

This application is a 371 of PCT/GB05/00303 filed Jan. 31, 2005.

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

The cell cycle is fundamental to the survival, regulation and proliferation of cells and is highly regulated to ensure that each step progresses in a timely and orderly manner. The progression of cells through the cell cycle arises from the sequential activation and de-activation of several members of the cyclin-dependent kinase (CDK) family. The activation of CDKs is dependent on their interaction with a family of intracellular proteins called cyclins. Cyclins bind to CDKs and this association is essential for CDK activity (such as CDK1, CDK2, CDK4 and/or CDK6) within the cell. Different cyclins are expressed and degraded at different points in the cell cycle to ensure that activation and inactivation of CDKs occurs in the correct order for progression through the cell cycle.

Moreover, CDKs appear to be downstream of a number of oncogene signalling pathways. Deregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK1, CDK2 and/or CDK4 (which operate at the G2/M, G1/S-S-G2/M and G1-S phases respectively) should be of value as an active inhibitor of cell proliferation, such as growth of mammalian cancer cells.

The inhibition of cell cycle kinases is expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

WO 02/20512, WO 03/076435, WO 03/076436, WO 03/076434 and WO 03/076433 describe certain 2-anilino-4-imidazolylpyrimidine derivatives that inhibit the effect of cell cycle kinases. The present invention is based on the discovery that a novel group of 2-(4-heterocyclylanilino)-4-imidazolylpyrimidines surprisingly inhibit the effects of cell cycle kinases showing activity against CDK1 and CDK2, particularly CDK2, and thus possess anti-cell-proliferation properties. The compounds of the present invention are not specifically disclosed in any of the above applications and we have surprisingly found that these compounds possess beneficial properties in terms of one or more of their pharmacological activity (particularly as compounds which inhibit CDK2) and/or pharmacokinetic, efficacious, metabolic and toxicological profiles that make them particularly suitable for in vivo administration to a warm blooded animal, such as man. In particular these compounds show improved physical and metabolic properties compared to those previously disclosed.

Accordingly, the present invention provides a compound of formula (I):

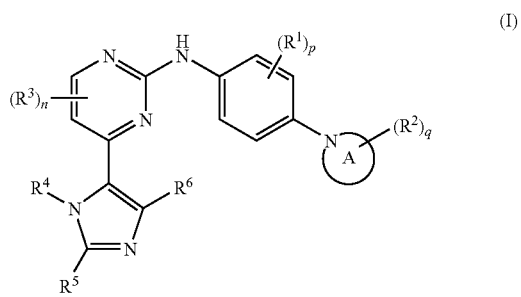

wherein:

Ring A is a nitrogen linked 4-7 membered saturated ring which optionally contains an additional nitrogen, oxygen or sulphur atom; wherein if Ring A contains an additional nitrogen atom that nitrogen may be optionally substituted by $R^7$;

$R^1$ is halo, nitro, cyano, hydroxy, amino, carboxy, carbamoyl, mercapto, $C_{1-6}$alkyl, $C_{1-6}$alkoxy, $C_{2-6}$alkenyl or $C_{2-6}$alkynyl;

p is 0-4; wherein the values of $R^1$ may be the same or different;

$R^2$ is selected from halo, nitro, cyano, hydroxy, trifluoromethoxy, amino, carboxy, carbamoyl, mercapto, azido, sulphamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, carbocyclyl-$R^{34}$—, heterocyclyl-$R^{35}$—, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$sulphamoyl; wherein $R^2$ independently may be optionally substituted on carbon by one or more $R^8$; or $R^2$ is —NHR$^9$, —NR$^{10}$R$^{11}$ or —O—R$^{12}$;

q is 0-2; wherein the values of $R^2$ maybe the same or different;

$R^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N—($C_{1-3}$alkyl)amino, N,N—($C_{1-3}$alkyl)$_2$amino, $C_{1-3}$alkanoylamino, N—($C_{1-3}$alkyl)carbamoyl, N,N—($C_{1-3}$alkyl)$_2$carbamoyl, $C_{1-3}$alkylS(O)$_a$ wherein a is 0 to 2, N—($C_{1-3}$alkyl)sulphamoyl or N,N—($C_{1-3}$alkyl)$_2$sulphamoyl; wherein $R^3$ may be independently optionally substituted on carbon by one or more $R^{13}$;

n is 0 to 2, wherein the values of $R^3$ may be the same or different;

$R^4$ is hydrogen, $C_{1-6}$alkyl, $C_{2-6}$alkenyl, $C_{2-6}$alkynyl, carbocyclyl or a carbon-linked heterocyclyl; wherein $R^4$ may be optionally substituted on carbon by one or more $R^{14}$; and wherein if said heterocyclyl contains an —NH— moiety that nitrogen may be optionally substituted by a group selected from $R^{15}$;

$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, $C_{3-8}$cycloalkyl or a 4-7 membered saturated heterocyclic group;

wherein $R^5$ and $R^6$ independently of each other may be optionally substituted on carbon by one or more $R^{16}$; and wherein if a 4-7 membered saturated heterocyclic group contains an —NH— moiety that nitrogen may be optionally substituted by a group selected from $R^{17}$;

$R^7$, $R^9$, $R^{10}$, $R^{11}$ and $R^{12}$ are independently selected from $C_{1-6}$alkyl, $C_{1-6}$alkanoyl, $C_{1-6}$alkylsulphonyl, $C_{2-6}$alkenylsulphonyl, $C_{2-6}$alkynylsulphonyl, $C_{1-6}$alkoxycarbonyl, carbamoyl, N—($C_{1-6}$alkyl)carbamoyl, N,N—($C_{1-6}$alkyl)carbamoyl, carbocyclyl, heterocyclyl, carbocyclyl-$R^{18}$— or heterocyclyl-$R^{19}$—; wherein $R^7$, $R^9$, $R^{10}$, $R^{11}$ and $R^{12}$ may be independently optionally substituted on carbon by a group selected from $R^{20}$; and wherein if said heterocyclyl contains an —NH— moiety that nitrogen may be optionally substituted by $R^{21}$;

$R^{14}$ and $R^{20}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkoxy$C_{1-6}$alkoxy, $C_{1-6}$alkoxy$C_{1-6}$alkoxy$C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl, heterocyclyl, carbocyclyl$C_{1-6}$alkyl-$R^{22}$—, heterocyclyl$C_{1-6}$allyl-$R^{23}$—, carbocyclyl-$R^{24}$— or heterocyclyl-$R^{25}$—; wherein $R^{14}$ and $R^{20}$ may be independently optionally substituted on carbon by one or more $R^{26}$; and wherein if said heterocyclyl contains an —NH— moiety that nitrogen may be optionally substituted by a group selected from $R^{27}$;

$R^{18}$, $R^{19}$, $R^{22}$, $R^{23}$, $R^{24}$, $R^{25}$, $R^{34}$ or $R^{35}$ are independently selected from —O—, —N($R^{28}$)—, —C(O)—, —N($R^{29}$)C(O)—, —C(O)N($R^{30}$)—, —S(O)$_s$—, —SO$_2$N($R^{31}$)— or —N($R^{32}$)SO$_2$—; wherein $R^{28}$, $R^{29}$, $R^{30}$, $R^{31}$ and $R^{32}$ are independently selected from hydrogen or $C_{1-6}$alkyl and s is 0-2;

$R^{15}$, $R^{17}$, $R^{21}$ and $R^{27}$ and are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^{15}$, $R^{17}$, $R^{21}$ and $R^{27}$ independently of each other may be optionally substituted on carbon by on or more $R^{33}$; and $R^8$, $R^{13}$, $R^{16}$, $R^{26}$ and $R^{33}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt or an in vivo hydrolysable ester thereof.

According to a further aspect of the invention there is provided a compound of formula (I) (as depicted above) wherein:

Ring A is a nitrogen linked 4-7 membered saturated ring which optionally contains an additional nitrogen, oxygen or sulphur atom; wherein if Ring A contains an additional nitrogen atom that nitrogen may be optionally substituted by $R^7$;

$R^1$ is halo, nitro, cyano, hydroxy, amino, carboxy, carbamoyl, mercapto, $C_{1-6}$alkyl, $C_{1-6}$alkoxy, $C_{2-6}$alkenyl or $C_{2-6}$alkynyl;

p is 0-4; wherein the values of $R^1$ may be the same or different;

$R^2$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$sulphamoyl; wherein $R^2$ independently may be optionally substituted on carbon by one or more $R^8$; or $R^2$ is —NHR$^9$, —NR$^{10}$R$^{11}$ or —O—R$^{12}$;

q is 0-2; wherein the values of $R^2$ maybe the same or different;

$R^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N—($C_{1-3}$alkyl)amino, N,N—($C_{1-3}$alkyl)$_2$amino, $C_{1-3}$alkanoylamino, N—($C_{1-3}$alkyl)carbamoyl, N,N—($C_{1-3}$alkyl)$_2$carbamoyl, $C_{1-3}$alkylS(O)$_a$ wherein a is 0 to 2, N—($C_{1-3}$alkyl)sulphamoyl or N,N—($C_{1-3}$alkyl)$_2$sulphamoyl; wherein $R^3$ may be independently optionally substituted on carbon by one or more $R^{13}$;

n is 0 to 2, wherein the values of $R^3$ may be the same or different;

$R^4$ is hydrogen, $C_{1-6}$alkyl, $C_{2-6}$alkenyl, $C_{2-6}$alkynyl, carbocyclyl or a carbon-linked heterocyclyl; wherein $R^4$ may be optionally substituted on carbon by one or more $R^{14}$; and wherein if said heterocyclyl contains an —NH— moiety that nitrogen may be optionally substituted by a group selected from $R^{15}$;

$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, $C_{3-8}$cycloalkyl or a 4-7 membered saturated heterocyclic group; wherein $R^5$ and $R^6$ independently of each other may be optionally substituted on carbon by one or more $R^{16}$; and wherein if a 4-7 membered saturated heterocyclic group contains an —NH— moiety that nitrogen may be optionally substituted by a group selected from $R^{17}$;

$R^7$, $R^9$, $R^{10}$, $R^{11}$ and $R^{12}$ are independently selected from $C_{1-6}$alkyl, $C_{1-6}$alkanoyl, $C_{1-6}$alkylsulphonyl, $C_{2-6}$alkenylsulphonyl, $C_{2-6}$alkynylsulphonyl, $C_{1-6}$alkoxycarbonyl, carbamoyl, N—($C_{1-6}$alkyl)carbamoyl, N,N—($C_{1-6}$alkyl)carbamoyl, carbocyclyl, heterocyclyl, carbocyclyl-$R^{18}$— or heterocyclyl-$R^{19}$—; wherein $R^7$, $R^9$, $R^{10}$, $R^{11}$ and $R^{12}$ may be independently optionally substituted on carbon by a group selected from $R^{20}$; and wherein if said heterocyclyl contains an —NH— moiety that nitrogen may be optionally substituted by $R^{21}$;

$R^{14}$ and $R^{20}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkoxy$C_{1-6}$alkoxy, $C_{1-6}$alkoxy$C_{1-6}$alkoxy$C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl, heterocyclyl, carbocyclyl$C_{1-6}$alkyl-$R^{22}$—, heterocyclyl$C_{1-6}$alkyl-$R^{23}$—, carbocyclyl-$R^{24}$— or heterocyclyl-$R^{25}$—; wherein $R^{14}$ and $R^{20}$ may be optionally substituted on carbon by one or more $R^{26}$; and wherein if said heterocyclyl contains an —NH— moiety that nitrogen may be optionally substituted by a group selected from $R^{27}$;

$R^{18}$, $R^{19}$, $R^{22}$, $R^{23}$, $R^{24}$, $R^{25}$ are independently selected from —O—, —N($R^{28}$)—, —C(O)—, —N($R^{29}$)C(O)—, —C(O)N($R^{30}$)—, —S(O)$_s$—, —SO$_2$N($R^{31}$)— or —N($R^{32}$)SO$_2$—; wherein $R^{28}$, $R^{29}$, $R^{30}$, $R^{31}$ and $R^{32}$ are independently selected from hydrogen or $C_{1-6}$alkyl and s is 0-2;

$R^{15}$, $R^{17}$, $R^{21}$ and $R^{27}$ and are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^{15}$, $R^{17}$, $R^{21}$ and $R^{27}$ independently of each other may be optionally substituted on carbon by on or more $R^{33}$; and $R^8$, $R^{13}$, $R^{16}$, $R^{26}$ and $R^{33}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt or an in vivo hydrolysable ester thereof.

According to a further aspect of the invention there is provided a compound of formula (I) (as depicted above) wherein:

Ring A is a nitrogen linked 4-7 membered saturated ring which optionally contains an additional nitrogen, oxygen or sulphur atom; wherein if Ring A contains an additional nitrogen atom that nitrogen may be optionally substituted by $R^7$;

$R^1$ is halo, nitro, cyano, hydroxy, amino, carboxy, carbamoyl, mercapto, $C_{1-6}$alkyl, $C_{1-6}$alkoxy, $C_{2-6}$alkenyl or $C_{2-6}$alkynyl;

p is 0-4; wherein the values of $R^1$ may be the same or different;

$R^2$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$sulphamoyl; wherein $R^2$ independently may be optionally substituted on carbon by one or more $R^8$; or $R^2$ is —NHR$^9$, —NR$^{10}$R$^{11}$ or —O—R$^{12}$;

q is 0-2; wherein the values of $R^2$ maybe the same or different;

$R^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N—($C_{1-3}$alkyl)amino, N,N—($C_{1-3}$alkyl)$_2$amino, $C_{1-3}$alkanoylamino, N—($C_{1-3}$alkyl)carbamoyl, N,N—($C_{1-3}$alkyl)$_2$carbamoyl, $C_{1-3}$alkylS(O)$_a$ wherein a is 0 to 2, N—($C_{1-3}$alkyl)sulphamoyl or N,N—($C_{1-3}$alkyl)$_2$sulphamoyl; wherein $R^3$ may be independently optionally substituted on carbon by one or more $R^{13}$;

n is 0 to 2, wherein the values of $R^3$ may be the same or different;

$R^4$ is hydrogen, $C_{1-6}$alkyl, $C_{2-6}$alkenyl, $C_{2-6}$alkynyl, carbocyclyl or a carbon-linked heterocyclyl; wherein $R^4$ may be optionally substituted on carbon by one or more $R^{14}$; and wherein if said heterocyclyl contains an —NH— moiety that nitrogen may be optionally substituted by a group selected from $R^{15}$;

$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, $C_{3-8}$cycloalkyl or a 4-7 membered saturated heterocyclic group; wherein $R^5$ and $R^6$ independently of each other may be optionally substituted on carbon by one or more $R^{16}$; and wherein if a 4-7 membered saturated heterocyclic group contains an —NH— moiety that nitrogen may be optionally substituted by a group selected from $R^{17}$;

$R^7$, $R^9$, $R^{10}$, $R^{11}$ and $R^{12}$ are independently selected from $C_{1-6}$alkyl, $C_{1-6}$alkanoyl, $C_{1-6}$alkylsulphonyl, $C_{2-6}$alkenylsulphonyl, $C_{2-6}$alkynylsulphonyl, $C_{1-6}$alkoxycarbonyl, carbamoyl, N—($C_{1-6}$alkyl)carbamoyl, N,N—($C_{1-6}$alkyl)carbamoyl, carbocyclyl, heterocyclyl, carbocyclyl-$R^{18}$— or heterocyclyl-$R^{19}$—; wherein $R^7$, $R^9$, $R^{10}$, $R^{11}$ and $R^{12}$ may be independently optionally substituted on carbon by a group selected from $R^{20}$; and wherein if said heterocyclyl contains an —NH— moiety that nitrogen may be optionally substituted by $R^{21}$;

$R^{14}$ and $R^{20}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkoxy$C_{1-6}$alkoxy, $C_{1-6}$alkoxy$C_{1-6}$alkoxy$C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl, heterocyclyl, carbocyclyl$C_{1-6}$alkyl-$R^{22}$—, heterocyclyl$C_{1-6}$alkyl-$R^{23}$—, carbocyclyl-$R^{24}$— or heterocyclyl-$R^{25}$—; wherein $R^{14}$ and $R^{20}$ may be optionally substituted on carbon by one or more $R^{26}$; and wherein if said heterocyclyl contains an —NH— moiety that nitrogen may be optionally substituted by a group selected from $R^{27}$;

$R^{18}$, $R^{19}$, $R^{22}$, $R^{23}$, $R^{24}$, $R^{25}$ are independently selected from —O—, —N($R^{28}$)—, —C(O)—, —N($R^{29}$)C(O)—, —C(O)N($R^{30}$)—, —S(O)$_s$—, —SO$_2$N($R^{31}$)— or —N($R^{32}$)SO$_2$—; wherein $R^{28}$, $R^{29}$, $R^{30}$, $R^{31}$ and $R^{32}$ are independently selected from hydrogen or $C_{1-6}$alkyl and s is 0-2;

$R^{15}$, $R^{17}$, $R^{21}$ and $R^{27}$ and are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^{15}$, $R^{17}$, $R^{21}$ and $R^{27}$ independently of each other may be optionally substituted on carbon by on or more $R^{33}$; and $R^8$, $R^{13}$, $R^{16}$, $R^{26}$ and $R^{33}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "carbocyclyl$C_{1-6}$alkyl-$R^{20}$" includes carbocyclylmethyl-$R^{20}$, 1-carbocyclylethyl-$R^{20}$ and 2-carbocyclylethyl-$R^{20}$. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)—, a ring nitrogen atom may optionally bear a $C_{1-6}$alkyl group and form a quaternary compound or a ring nitrogen and/or sulphur atom may be optionally oxidised to form the N-oxide and or the S-oxides. Examples and suitable values of the term "heterocyclyl" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. In one aspect of the invention a "heterocyclyl" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl.

A "4-7 membered saturated heterocyclic group" is a saturated monocyclic ring containing 4-7 atoms of which at least one atom is chosen from nitrogen, sulphur or oxygen, which may, unless otherwise specified, be carbon or nitrogen linked, wherein a —$CH_2$— group can optionally be replaced by a —C(O)— and a sulphur atom may be optionally oxidised to form the S-oxides. Examples and suitable values of the term "4-7 membered saturated heterocyclic group" are morpholino, piperidyl, 1,4-dioxanyl, 1,3-dioxolanyl, 1,2-oxathiolanyl, imidazolidinyl, pyrazolidinyl, piperazinyl, thiazolidinyl, pyrrolidinyl, thiomorpholino, homopiperazinyl and tetrahydropyranyl.

Ring A is a "nitrogen linked 4-7 membered saturated ring which optionally contains an additional nitrogen, oxygen or sulphur atom". A "nitrogen linked 4-7 membered saturated ring which optionally contains an additional nitrogen, oxygen or sulphur atom" is a saturated monocyclic ring containing 4-7 atoms linked to the phenyl moiety of formula (I) via a nitrogen atom contained in the ring, the ring optionally contains an additional heteroatom selected from nitrogen, sulphur or oxygen, wherein a —$CH_2$— group can optionally be replaced by a —C(O)—, and the optional sulphur atom may be optionally oxidised to form the S-oxides.

Examples of "$C_{1-3}$alkyl" include methyl, ethyl, propyl and isopropyl. An example of "$C_{1-6}$alkanoyloxy" is acetoxy. Examples of "$C_{1-6}$alkoxycarbonyl" include methoxycarbonyl, ethoxycarbonyl, n- and t-butoxycarbonyl. Examples of "$C_{1-6}$alkoxy" and "$C_{1-3}$alkoxy" include methoxy, ethoxy and propoxy. Examples of "$C_{1-6}$alkanoylamino" and "$C_{1-3}$alkanoylamino" include formamido, acetamido and propionylamino. Examples of "$C_{1-6}$alkylS(O)$_a$ wherein a is 0 to 2" and "$C_{1-3}$alkylS(O)$_a$ wherein a is 0 to 2" include methylthio, ethylthio, methylsulphinyl, ethylsulphinyl, mesyl and ethylsulphonyl. Examples of "$C_{1-6}$alkylS(O)$_r$ wherein r is 1 to 2" include methylsulphinyl, ethylsulphinyl, mesyl and ethylsulphonyl. Examples of "$C_{1-6}$alkanoyl" and "$C_{1-3}$alkanoyl" include propionyl and acetyl. Examples of "N—$C_{1-6}$alkylamino" and "N—$C_{1-3}$alkylamino" include methylamino and ethylamino. Examples of "N,N—($C_{1-6}$alkyl)$_2$amino" and "N,N—($C_{1-3}$alkyl)$_2$amino" include di-N-methylamino, di-(N-ethyl)amino and N-ethyl-N-methylamino. Examples of "$C_{2-6}$alkenyl" and "$C_{2-3}$alkenyl" are vinyl, allyl and 1-propenyl. Examples of "$C_{2-6}$alkynyl" and "$C_{2-3}$alkynyl" are ethynyl, 1-propynyl and 2-propynyl. Examples of "N—($C_{1-6}$alkyl)sulphamoyl" and "N—($C_{1-3}$alkyl)sulphamoyl" are N-(methyl)sulphamoyl and N-(ethyl)sulphamoyl. Examples of "N,N—($C_{1-6}$alkyl)$_2$sulphamoyl" and "N,N—($C_{1-3}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" and "N—($C_{1-3}$alkyl)carbamoyl" are methylaminocarbonyl and ethylaminocarbonyl. Examples of "N,N—($C_{1-6}$alkyl)$_2$carbamoyl" and "N,N—($C_{1-3}$alkyl)$_2$carbamoyl" are dimethylaminocarbonyl and methylethylaminocarbonyl. Examples of "$C_{3-8}$-cycloalkyl" are cyclopropyl, cyclobutyl, cyclopropyl and cyclohexyl. Examples of "$C_{1-6}$alkylsulphonylamino" include methylsulphonylamino, isopropylsulphonylamino and t-butylsulphonylamino. Examples of "$C_{1-6}$alkylsulphonyl" include methylsulphonyl, isopropylsulphonyl and t-butylsulphonyl. Examples of "$C_{2-6}$alkenylsulphonyl" include vinylsulphonyl, allylsulphonyl and 1-propenylsulphonyl. Examples of "$C_{2-6}$alkynylsulphonyl" include ethynylsulphonyl, 1-propynylsulphonyl and 2-propynylsulphonyl. Examples of "$C_{1-6}$alkoxy$C_{1-6}$alkoxy" include methoxyethoxy, 2-ethoxypropoxy and 2-isopropoxybutoxy. Examples of "$C_{1-6}$alkoxy$C_{1-6}$alkoxy$C_{1-6}$alkoxy" include methoxyethoxymethoxy, 2-ethoxypropoxymethoxy and 3-(2-isopropoxybutoxy)ethoxy. Examples of "$C_{2-6}$alkenyloxy" include vinyloxy and allyloxy. Examples of "$C_{2-6}$alkynyloxy" include ethynyloxy and 2-propynyloxy.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity. In particular the skilled reader will appreciate that when $R^4$ is hydrogen, the imidazole ring as drawn in formula (I) may tautomerise.

It is also to be understood that certain compounds of the formula (I) can exist in solvated as well as unsolvated forms such as, for example, hydrated forms. It is to be understood that the invention encompasses all such solvated forms which possess CDK inhibitory activity.

Particular values of variable groups are as follows. Such values may be used where appropriate with any of the definitions, claims or embodiments defined hereinbefore or hereinafter.

Ring A is a nitrogen linked 4-7 membered saturated ring which optionally contains an additional nitrogen or oxygen atom; wherein if Ring A contains an additional nitrogen atom that nitrogen may be optionally substituted by $R^7$; wherein $R^7$ is selected from $C_{1-6}$alkanoyl, $C_{1-6}$alkylsulphonyl, $C_{2-6}$alkenylsulphonyl, carbocyclyl-$R^{18}$— or heterocyclyl-$R^{19}$—; wherein $R^7$ may be independently optionally substituted on carbon by a group selected from $R^{20}$; and wherein if said heterocyclyl contains an —NH— moiety that nitrogen may be optionally substituted by $R^{21}$;

$R^{18}$ and $R^{19}$ are —C(O)—;

$R^{20}$ is selected from halo, cyano, hydroxy, $C_{1-6}$alkoxy, $C_{2-6}$alkynyloxy, $C_{1-6}$alkanoyloxy, N,N—$(C_{1-6}$alkyl$)_2$amino, $C_{1-6}$alkylS(O)$_a$ wherein a is 2 or heterocyclyl; wherein $R^{20}$ may be optionally substituted on carbon by one or more $R^{26}$;

$R^{21}$ is $C_{1-6}$alkyl; and $R^{26}$ is hydroxy.

Ring A is a nitrogen linked 4-7 membered saturated ring which optionally contains an additional nitrogen or oxygen atom; wherein if Ring A contains an additional nitrogen atom that nitrogen may be optionally substituted by $R^7$; wherein $R^7$ is selected from $C_{1-6}$alkanoyl, $C_{1-6}$alkylsulphonyl, $C_{2-6}$alkenylsulphonyl, carbocyclyl-$R^{18}$— or heterocyclyl-$R^{19}$—; wherein $R^7$ may be independently optionally substituted on carbon by a group selected from $R^{20}$; and wherein if said heterocyclyl contains an —NH— moiety that nitrogen may be optionally substituted by $R^{21}$;

$R^{18}$ and $R^{19}$ are —C(O)—;

$R^{20}$ is selected from halo, cyano, hydroxy, $C_{1-6}$alkoxy, $C_{2-6}$alkynyloxy, $C_{1-6}$alkanoyloxy, N,N—$(C_{1-6}$alkyl$)_2$amino, $C_{1-6}$alkylS(O)$_a$ wherein a is 2 or heterocyclyl; wherein $R^{20}$ may be optionally substituted on carbon by one or more $R^{26}$;

$R^{21}$ is $C_{1-6}$alkyl; and $R^{26}$ is hydroxy.

Ring A is a nitrogen linked 4-7 membered saturated ring which optionally contains an additional nitrogen, oxygen or sulphur atom; wherein if Ring A contains an additional nitrogen atom that nitrogen may be optionally substituted by $R^7$; wherein $R^7$ is selected from $C_{1-6}$alkanoyl, $C_{1-6}$alkylsulphonyl, $C_{2-6}$alkenylsulphonyl, carbocyclyl-$R^{18}$— or heterocyclyl-$R^{19}$—; wherein $R^7$ may be independently optionally substituted on carbon by a group selected from $R^{20}$; and wherein if said heterocyclyl contains an —NH— moiety that nitrogen may be optionally substituted by $R^{21}$;

$R^{20}$ is selected from halo, cyano, hydroxy, $C_{1-6}$alkoxy, $C_{2-6}$alkynyloxy, $C_{1-6}$alkanoyloxy, N,N—$(C_{1-6}$alkyl$)_2$amino, $C_{1-6}$alkylS(O)$_a$ wherein a is 2 or heterocyclyl; wherein $R^{20}$ may be optionally substituted on carbon by one or more $R^{26}$;

$R^{18}$ and $R^{19}$ are —C(O)—;

$R^{21}$ is $C_{1-6}$alkyl; and $R^{26}$ is hydroxy.

Ring A is a nitrogen linked 6 membered saturated ring which optionally contains an additional nitrogen atom; wherein if Ring A contains an additional nitrogen atom that nitrogen may be optionally substituted by $R^7$; wherein $R^7$ is selected from $C_{1-6}$alkanoyl, $C_{1-6}$alkylsulphonyl and $C_{2-6}$alkenylsulphonyl; wherein $R^7$ may be optionally substituted on carbon by a group selected from $R^{20}$; wherein $R^{20}$ is selected from hydroxy, $C_{1-6}$alkoxy, $C_{1-6}$alkanoyloxy and N,N—$(C_{1-6}$alkyl$)_2$amino.

Ring A is piperazin-1-yl, morpholino, pyrrolidinyl or azetidinyl; wherein said piperazin-1-yl may be optionally substituted on nitrogen by $R^7$; wherein $R^7$ is selected from acetyl, propionyl, 2,2-dimethylpropanoyl, 3-methylbutanoyl, butyryl, isobutyryl, mesyl, ethylsulphonyl, ethenylsulphonyl, cyclopropyl-$R^{18}$—, tetrahydrofuranyl-$R^{19}$— or pyrrolidinyl-$R^{19}$—; wherein $R^7$ may be independently optionally substituted on carbon by a group selected from $R^{20}$; and wherein if said heterocyclyl contains an —NH— moiety that nitrogen may be optionally substituted by $R^{21}$;

$R^{18}$ and $R^{19}$ are —C(O)—;

$R^{20}$ is selected from fluoro, chloro, cyano, hydroxy, methoxy, prop-2-yn-1-yloxy, acetoxy, dimethylamino, diethylamino, mesyl, tetrazolyl, pyrrolidinyl, morpholino, azetidinyl; wherein $R^{20}$ may be optionally substituted on carbon by one or more $R^{26}$;

$R^{21}$ is methyl; and $R^{26}$ is hydroxy.

Ring A is piperazin-1-yl or morpholino; wherein said piperazinyl may be optionally substituted on nitrogen by $R^7$; wherein $R^7$ is selected from acetyl, propionyl, 2-methylpropionyl, 2,2-dimethylpropionyl, butanoyl, 3-methylbutanoyl, mesyl, vinylsulphonyl, cyclopropyl-$R^{18}$—, pyrrolidin-2-yl-$R^{19}$—, tetrahydrofuran-2-yl-$R^{19}$— or tetrahydrofuran-3-yl-$R^{19}$—; wherein $R^7$ may be independently optionally substituted on carbon by a group selected from $R^{20}$; and wherein if said heterocyclyl contains an —NH— moiety that nitrogen may be optionally substituted by $R^{21}$;

$R^{20}$ is selected from fluoro, chloro, cyano, hydroxy, methoxy, 2-propynyloxy, acetoxy, dimethylamino, diethylamino, mesyl, azetidin-1-yl, pyrrolidin-1-yl, morpholino, tetrazol-1-yl or tetrazol-5-yl; wherein $R^{20}$ may be optionally substituted on carbon by one or more $R^{26}$;

$R^{18}$ and $R^{19}$ are —C(O)—;

$R^{21}$ is methyl; and $R^{26}$ is hydroxy.

Ring A is morpholino or piperazin-1-yl; wherein if Ring A is piperazin-1-yl the —NH— moiety may be optionally substituted by $R^7$; wherein $R^7$ is selected from acetyl, methylsulphonyl, ethylsulphonyl and vinylsulphonyl; wherein $R^7$ may be optionally substituted on carbon by a group selected from $R^{20}$; wherein $R^{20}$ is selected from hydroxy, methoxy, acetoxy and dimethylamino.

Ring A, $R^2$ and q together form piperazin-1-yl, morpholino, 4-mesylpiperazin-1-yl, 4-acetylpiperazin-1-yl, 4-(2-acetoxyacetyl)piperazin-1-yl, 4-(2-hydroxyacetyl)piperazin-1-yl, 4-(2-chloroacetyl)piperazin-1-yl, 4-(2-methoxyacetyl)piperazin-1-yl, (3-methoxypropanoyl)piperazin-1-yl, (3-hydroxy-3-methylbutanoyl)piperazin-1-yl, (3-hydroxy-2,2-dimethylpropanoyl)piperazin-1-yl, ((R)-3-methyl-2-hydroxybutanoyl)piperazin-1-yl, ((S)-3-methyl-2-hydroxybutanoyl)piperazin-1-yl, 4-(2-dimethylaminoacetyl)piperazin-1-yl, 4-[2-(dimethylamino)ethylsulphonyl]piperazin-1-yl, 4-[2-(methoxy)ethylsulphonyl]piperazin-1-yl, 4-[2-(hydroxy)ethylsulphonyl]piperazin-1-yl, 4-(cyclopropylcarbonyl)piperazin-1-yl, 4-(1-hydroxycyclopropylcarbonyl)piperazin-1-yl, 4-(1-cyanocyclopropylcarbonyl)piperazin-1-yl, 4-(2-hydroxy-2-methylpropanoyl)piperazin-1-yl, 4-((R)-2-hydroxypropanoyl)piperazin-1-yl, 4-((S)-2-hydroxypropanoyl)piperazin-1-yl, 4-((R)-2-methoxypropanoyl)piperazin-1-yl, 4-((S)-2-methoxypropanoyl)piperazin-1-yl, 4-((R)-tetrahydrofuran-2-ylcarbonyl)piperazin-1-yl, 4-((S)-tetrahydrofuran-2-ylcarbonyl)piperazin-1-yl, 4-(isobutyryl)piperazin-1-yl, 4-((R)-2-hydroxybutanoyl)piperazin-1-yl, 4-((S)-2-hydroxybutanoyl)piperazin-1-yl, (R)-3-acetylaminopyrrolidin-1-yl, (S)-3-acetylaminopyrrolidin-1-yl, (R)-2-(cyclopropylaminocarbonyl)pyrrolidin-1-yl, (R)-2-(N-methylcarbamoyl)pyrrolidin-1-yl, (S)-2-(N,N-dimethylcarbamoyl)pyrrolidin-1-yl, 4-(ethenylsulphonyl)piperazin-1-yl, 4-[2-(2-propyn-1-yloxy)acetyl]piperazin-1-yl, 4-(tetrahydrofuran-3-ylcarbonyl)piperazin-1-yl, 4-(3-dimethylaminopropanoyl)piperazin-1-yl, 4-[2-(N-methyl-N-hydroxymethylamino)acetyl]piperazin-1-yl, 4-[3-hydroxy-2-(hydroxymethyl)propanoyl]piperazin-1-yl, 4-[2-(1,2,3,4-tetrazol-1-yl)acetyl]piperazin-1-yl, 4-[2-(1,2,3,4-tetrazol-5-yl)acetyl]piperazin-1-yl, 4-(1-methyl-L-prolyl)piperazin-1-yl, 4-[2-(mesyl)acetyl]piperazin-1-yl, 4-(2,2-difluoroacetyl)piperazin-1-yl, 4-[2-(pyrrolidin-1-yl)acetyl]piperazin-1-yl, 4-[2-(morpholino)acetyl]piperazin-1-yl, 4-[2-(diethylamino)acetyl]piperazin-1-yl, 4-(propionyl)piperazin-1-yl, 4-(3-hydroxypropionyl)piperazin-1-yl, 4-[2-(azetidin-1-yl)acetyl]piperazin-1-yl, (R)-3-aminopyrrolidin-1-yl, (S)-3-aminopyrrolidin-1-yl, (3R,5S)-4-acetyl-3,5-dimethylpiperazin-1-yl, (2S,5R)-4-acetyl-2,5-dimethylpiperazin-1-yl, (2RS,6SR)-2,6-dimethylmorpholin-4-yl]phenyl, 3-hydroxyazetidin-1-yl, 3-acetylaminoazetidin-1-yl, 3-(2-hydroxyacetylamino)azetidin-1-yl, 3-mesylaminoazetidin-1-yl, 3-mesyloxyazetidin-1-yl, 3-azidoazetidin-1-yl, 3-aminoazetidin-1-yl, (3R)-3-{[(2S)-2-hydroxypropanoyl]amino}pyrrolidin-1-yl, (3S)-3-{[(2S)-2-hydroxypropanoyl]amino}pyrrolidin-1-yl, (3S)-3-(glycoloylamino)pyrrolidin-1-yl and (3R)-3-(glycoloylamino)pyrrolidin-1-yl.

Ring A is [4-(2-acetoxyacetyl)piperazin-1-yl; [4-(hydroxyacetyl)piperazin-1-yl; 4-((R)-2-hydroxybutanoyl)piperazin-1-yl; 4-((R)-2-hydroxypropionyl)piperazin-1-yl; 4-((R)-2-methoxypropionyl)piperazin-1-yl; 4-((R)-3-methyl-2-hydroxybutanoyl)piperazin-1-yl; 4-((R)-tetrahydrofur-2-ylcarbonyl)piperazin-1-yl; 4-((S)-2-hydroxybutanoyl)piperazin-1-yl; 4-((S)-2-methoxypropionyl)piperazin-1-yl; 4-((S)-3-methyl-2-hydroxybutanoyl)piperazin-1-yl; 4-((S)-tetrahydrofur-2-ylcarbonyl)piperazin-1-yl; 4-(1-cyanocycloprop-1-ylcarbonyl)piperazin-1-yl; 4-(1-hydroxycycloprop-1-ylcarbonyl)piperazin-1-yl; 4-(1-methyl-L-prolylcarbonyl)piperazin-1-yl; 4-(2-(R)-tetrahydrofur-2-ylcarbonyl)piperazin-1-yl; 4-(2-(S)-2-hydroxypropionyl)piperazin-1-yl)piperazin-1-yl; 4-(2-(S)-tetrahydrofur-2-yl)piperazin-1-yl; 4-(2,2-difluoroacetyl)piperazin-1-yl; 4-(2-acetoxyacetyl)piperazin-1-yl; 4-(2-dimethylaminoacetyl)piperazin-1-yl; 4-(2-dimethylaminoethylsulphonyl)piperazin-1-yl; 4-(2-hydroxy-2-methylpropionyl)piperazin-1-yl; 4-(2-hydroxyacetyl)piperazin-1-yl; 4-(2-hydroxyethylsulphonyl)piperazin-1-yl; 4-(2-hydroxypropionyl)piperazin-1-yl; 4-(2-mesylacetyl)piperazin-1-yl; 4-(2-methoxyacetyl)piperazin-1-yl; 4-(2-methoxyethylsulphonyl)piperazin-1-yl; 4-(2-methyl-2-hydroxypropionyl)piperazin-1-yl; 4-(2-methylpropionyl)piperazin-1-yl; 4-(2-morpholinoacetyl)piperazin-1-yl; 4-(2-pyrrolidin-1-ylacetyl)piperazin-1-yl; 4-(3-dimethylaminopropionyl)piperazin-1-yl; 4-(3-hydroxy-2,2-dimethylpropionyl)piperazin-1-yl; 4-(3-hydroxypropionyl)piperazin-1-yl; 4-(3-methoxypropionyl)piperazin-1-yl; 4-(3-methyl-3-hydroxybutanoyl)piperazin-1-yl; 4-(4-hydroxybutanoyl)piperazin-1-yl; 4-(acetoxyacetyl)piperazin-1-yl; 4-(acetyl)piperazin-1-yl; 4-(azetidin-1-ylacetyl)piperazin-1-yl; 4-(chloroacetyl)piperazin-1-yl; 4-(cyclopropyl)piperazin-1-yl; 4-(propionyl)piperazin-1-yl; 4-(tetrahydrofur-3-ylcarbonyl)piperazin-1-yl; 4-(vinylsulphonyl)piperazin-1-yl; 4-[2-(1H-tetrazol-5-yl)acetyl]piperazin-1-yl; 4-[2-(2-propynyloxy)acetyl]piperazin-1-yl; 4-[2-(N-hydroxymethyl-N-methylamino)acetyl]piperazin-1-yl; 4-[2-(tetrazol-1-yl)acetyl]piperazin-1-yl; 4-acetylpiperazin-1-yl; 4-mesylpiperazin-1-yl; morpholino; and piperazin-1-yl.

Ring A is 4-methylsulphonylpiperazin-1-yl, 4-vinylsulphonylpiperazin-1-yl, 4-acetylpiperazin-1-yl, 4-(acteoxyacetyl)piperazin-1-yl, 4-(hydroxyacetyl)piperazin-1-yl, 4-(dimethylaminoacetyl)piperazin-1-yl, 4-(2-dimethylaminoethylsulphonyl)piperazin-1-yl, 4-(2-methoxyethylsulphonyl)piperazin-1-yl, 4-(2-hydroxyethylsulphonyl)piperazin-1-yl, piperazin-1-yl or morpholino.

$R^1$ is halo or $C_{1-6}$alkyl.

$R^1$ is fluoro, chloro or methyl.

p is 0-2; wherein the values of $R^1$ may be the same or different.

p is 0 or 1.

p is 1.

p is 0.

$R^2$ is selected from hydroxy, amino, azido, $C_{1-6}$alkyl, N—($C_{1-6}$alkyl)carbamoyl, N,N—($C_{1-6}$alkyl)$_2$carbamoyl, carbocyclyl-$R^{34}$—, —NHR$^9$ or —O—R$^{12}$;

$R^9$ and $R^{12}$ are independently selected from $C_{1-6}$alkanoyl or $C_{1-6}$alkylsulphonyl; wherein $R^9$ and $R^{12}$ may be independently optionally substituted on carbon by a group selected from $R^{20}$;

$R^{20}$ is hydroxy; and $R^{34}$ is —N(R$^{29}$)C(O)—; wherein $R^{29}$ is hydrogen.

$R^2$ is selected from hydroxy, amino, azido, methyl, N-methylcarbamoyl, N,N-dimethylcarbamoyl, cyclopropyl-$R^{34}$—, —NHR$^9$ or —O—R$^{12}$;

$R^9$ and $R^{12}$ are independently selected from acetyl, propionyl or mesyl; wherein $R^9$ and $R^{12}$ may be independently optionally substituted on carbon by a group selected from $R^{20}$;

$R^{20}$ is hydroxy; and $R^{34}$ is —N(R$^{29}$)C(O)—; wherein $R^{29}$ is hydrogen.

$R^2$ is selected from hydroxy, amino, azido, methyl, N-methylcarbamoyl, N,N-dimethylcarbamoyl, acetamido, {[(2S)-2-hydroxypropanoyl]amino}, glycoloylamino, mesylamino, 2-hydroxyacetamido, mesyloxy or N-cyclopropylcarbamoyl.

q is 0 or 1.
q is 2.
q is 1.
q is 0.
$R^3$ is halo.
$R^3$ is fluoro or chloro.
$R^3$ is 5-fluoro or 5-chloro.
$R^3$ is 5-fluoro.
$R^3$ is 5-chloro.
n is 0 or 1.
n is 1.
n is 0.
$R^4$ is $C_{1-6}$alkyl or carbocyclyl; wherein $R^4$ may be optionally substituted on carbon by one or more $R^{14}$; wherein
$R^{14}$ is carbocyclyl.
$R^4$ is $C_{1-4}$alkyl or cyclobutyl; wherein $R^4$ may be optionally substituted on carbon by one or more $R^{14}$; wherein
$R^{14}$ is cyclopropyl.
$R^4$ is ethyl, isopropyl, isobutyl, cyclobutyl or cyclopropylmethyl.
$R^4$ is isopropyl.
$R^5$ and $R^6$ are independently selected from hydrogen or $C_{1-6}$alkyl; wherein $R^5$ and $R^6$ independently of each other may be optionally substituted on carbon by one or more $R^{16}$; wherein
$R^{16}$ is selected from methoxy.
$R^5$ and $R^6$ are independently selected from hydrogen methyl, ethyl or propyl; wherein $R^5$ and $R^6$ independently of each other may be optionally substituted on carbon by one or more $R^{16}$; wherein
$R^{16}$ is selected from methoxy.
$R^5$ and $R^6$ are independently selected from hydrogen, methyl, ethyl, methoxymethyl, propyl.
$R^5$ is $C_{1-6}$alkyl; wherein $R^5$ may be optionally substituted on carbon by one or more $R^{16}$; wherein
$R^{16}$ is methoxy.
$R^5$ is $C_{1-4}$alkyl; wherein $R^5$ may be optionally substituted on carbon by one or more $R^{16}$; wherein
$R^{16}$ is methoxy.
$R^5$ is methyl, ethyl, propyl or methoxymethyl.
$R^5$ is methyl.
$R^6$ is hydrogen.
$R^4$ is isopropyl, $R^5$ is methyl and $R^6$ is hydrogen.

Therefore in a further aspect of the invention there is provided a compound of formula (I) (as depicted above) wherein:

Ring A is a nitrogen linked 4-7 membered saturated ring which optionally contains an additional nitrogen or oxygen atom; wherein if Ring A contains an additional nitrogen atom that nitrogen may be optionally substituted by $R^7$;

$R^1$ is halo or $C_{1-6}$alkyl;

p is 0 or 1;

$R^2$ is selected from hydroxy, amino, azido, $C_{1-6}$alkyl, N—($C_{1-6}$alkyl)carbamoyl, N,N—($C_{1-6}$alkyl)$_2$carbamoyl, carbocyclyl-$R^{34}$—, —NHR$^9$ or —O—R$^{12}$;

q is 0-2; wherein the values of $R^2$ maybe the same or different;

$R^3$ is halo;

n is 0 or 1;

$R^4$ is $C_{1-6}$alkyl or carbocyclyl; wherein $R^4$ may be optionally substituted on carbon by one or more $R^{14}$;

$R^5$ and $R^6$ are independently selected from hydrogen or $C_{1-6}$alkyl; wherein $R^5$ and $R^6$ independently of each other may be optionally substituted on carbon by one or more $R^{16}$;

$R^7$ is selected from $C_{1-6}$alkanoyl, $C_{1-6}$alkylsulphonyl, $C_{2-6}$alkenylsulphonyl, carbocyclyl-$R^{18}$— or heterocyclyl-$R^{19}$—; wherein $R^7$ may be independently optionally substituted on carbon by a group selected from $R^{20}$; and wherein if said heterocyclyl contains an —NH— moiety that nitrogen may be optionally substituted by $R^{21}$;

$R^9$ and $R^{12}$ are independently selected from $C_{1-6}$alkanoyl or $C_{1-6}$alkylsulphonyl; wherein $R^9$ and $R^{12}$ may be independently optionally substituted on carbon by a group selected from $R^{20}$;

$R^{14}$ is carbocyclyl;

$R^{16}$ is selected from methoxy;

$R^{18}$ and $R^{19}$ are —C(O)—;

$R^{20}$ is selected from halo, cyano, hydroxy, $C_{1-6}$alkoxy, $C_{2-6}$alkynyloxy, $C_{1-6}$alkanoyloxy, N,N—($C_{1-6}$alkyl)$_2$amino, $C_{1-6}$alkylS(O)$_a$ wherein a is 2 or heterocyclyl; wherein $R^{20}$ may be optionally substituted on carbon by one or more $R^{26}$;

$R^{21}$ is $C_{1-6}$alkyl;

$R^{26}$ is hydroxy; or $R^{34}$ is —N(R$^{29}$)C(O)—; wherein $R^{29}$ is hydrogen;

or a pharmaceutically acceptable salt or an in vivo hydrolysable ester thereof.

Therefore in a further aspect of the invention there is provided a compound of formula (I) (as depicted above) wherein:

Ring A, $R^2$ and q together form piperazin-1-yl, morpholino, 4-mesylpiperazin-1-yl, 4-acetylpiperazin-1-yl, 4-(2-acetoxyacetyl)piperazin-1-yl, 4-(2-hydroxyacetyl)piperazin-1-yl, 4-(2-chloroacetyl)piperazin-1-yl, 4-(2-methoxyacetyl)piperazin-1-yl, (3-methoxypropanoyl)piperazin-1-yl, (3-hydroxy-3-methylbutanoyl)piperazin-1-yl, (3-hydroxy-2,2-dimethylpropanoyl)piperazin-1-yl, ((R)-3-methyl-2-hydroxybutanoyl)piperazin-1-yl, ((S)-3-methyl-2-hydroxybutanoyl)piperazin-1-yl, 4-(2-dimethylaminoacetyl)piperazin-1-yl, 4-[2-(dimethylamino)ethylsulphonyl]piperazin-1-yl, 4-[2-(methoxy)ethylsulphonyl]piperazin-1-yl, 4-[2-(hydroxy)ethylsulphonyl]piperazin-1-yl, 4-(cyclopropylcarbonyl)piperazin-1-yl, 4-(1-hydroxycyclopropylcarbonyl)piperazin-1-yl, 4-(1-cyanocyclopropylcarbonyl)piperazin-1-yl, 4-(2-hydroxy-2-methylpropanoyl)piperazin-1-yl, 4-((R)-2-hydroxypropanoyl)piperazin-1-yl, 4-((S)-2-hydroxypropanoyl)piperazin-1-yl, 4-((R)-2-methoxypropanoyl)piperazin-1-yl, 4-((S)-2-methoxypropanoyl)piperazin-1-yl, 4-((R)-tetrahydrofuran-2-ylcarbonyl)piperazin-1-yl, 4-((S)-tetrahydrofuran-2-ylcarbonyl)piperazin-1-yl, 4-(isobutyryl)piperazin-1-yl, 4-((R)-2-hydroxybutanoyl)piperazin-1-yl, 4-((S)-2-hydroxybutanoyl)piperazin-1-yl, (R)-3-acetylaminopyrrolidin-1-yl, (S)-3-acetylaminopyrrolidin-1-yl, (R)-2-(cyclopropylaminocarbonyl)pyrrolidin-1-yl, (R)-2-(N-methylcarbamoyl)pyrrolidin-1-yl, (S)-2-(N,N-dimethylcarbamoyl)pyrrolidin-1-yl, 4-(ethenylsulphonyl)piperazin-1-yl, 4-[2-(2-propyn-1-yloxy)acetyl]piperazin-1-yl, 4-(tetrahydrofuran-3-ylcarbonyl)piperazin-1-yl, 4-(3-dimethylaminopropanoyl)piperazin-1-yl, 4-[2-(N-methyl-N-hydroxymethylamino)acetyl]piperazin-1-yl, 4-[3-hydroxy-2-(hydroxymethyl)propanoyl]piperazin-1-yl, 4-[2-(1,2,3,4-tetrazol-1-yl)acetyl]piperazin-1-yl, 4-[2-(1,2,3,4-tetrazol-5-yl)acetyl]piperazin-1-yl, 4-(1-methyl-L-prolyl)piperazin-1-yl, 4-[2-(mesyl)acetyl]piperazin-1-yl, 4-(2,2-difluoroacetyl)piperazin-1-yl, 4-[2-(pyrrolidin-1-yl)acetyl]piperazin-1-yl, 4-[2-(morpholino)acetyl]piperazin-1-yl, 4-[2-(diethylamino)acetyl]piperazin-1-yl, 4-(propionyl)piperazin-1-yl, 4-(3-hydroxypropionyl)piperazin-1-yl, 4-[2-(azetidin-1-yl)acetyl]piperazin-1-yl, (R)-3-aminopyrrolidin-1-yl, (S)-3-aminopyrrolidin-1-yl, (3R,5S)-4-acetyl-3,5-dimethylpiperazin-1-yl, (2S,5R)-4-acetyl-2,5-dimethylpiperazin-1-yl, (2RS,6SR)-2,6-dimethylmorpholin-4-yl]phenyl, 3-hydroxyazetidin-1-yl, 3-acetylaminoazetidin-1-yl, 3-(2-hydroxyacetylamino)azetidin-1-yl, 3-mesylaminoazetidin-1-yl, 3-mesyloxyazetidin-1-yl, 3-azidoazetidin-1-yl, 3-aminoazetidin-1-yl, (3R)-3-{[(2S)-2-hydroxypropanoyl]amino}pyrrolidin-1-yl, (3S)-3-{[(2S)-2-hydroxypropanoyl]amino}pyrrolidin-1-yl, (3S)-3-(glycoloylamino)pyrrolidin-1-yl and (3R)-3-(glycoloylamino)pyrrolidin-1-yl;

$R^1$ is fluoro, chloro or methyl;
p is 0 or 1;
$R^2$ is selected from hydroxy, amino, azido, methyl, N-methylcarbamoyl, N,N-dimethylcarbamoyl, acetamido, {[(2S)-2-hydroxypropanoyl]amino}, glycoloylamino, mesylamino, 2-hydroxyacetamido, mesyloxy or N-cyclopropylcarbamoyl.
q is 0-2; wherein the values of $R^2$ maybe the same or different;
$R^3$ is 5-fluoro or 5-chloro;
n is 0 or 1;
$R^4$ is ethyl, isopropyl, isobutyl, cyclobutyl or cyclopropylmethyl;
$R^5$ and $R^6$ are independently selected from hydrogen, methyl, ethyl, methoxymethyl, propyl;

or a pharmaceutically acceptable salt or an in vivo hydrolysable ester thereof.

Therefore in a further aspect of the invention there is provided a compound of formula (I) (as depicted above) wherein:

Ring A is a nitrogen linked 4-7 membered saturated ring which optionally contains an additional nitrogen, oxygen or sulphur atom; wherein if Ring A contains an additional nitrogen atom that nitrogen may be optionally substituted by $R^7$; wherein
$R^3$ is halo;
$R^4$ is $C_{1-6}$alkyl or carbocyclyl; wherein $R^4$ may be optionally substituted on carbon by one or more $R^{14}$; wherein
$R^5$ and $R^6$ are independently selected from hydrogen or $C_{1-6}$alkyl; wherein $R^5$ and $R^6$ independently of each other may be optionally substituted on carbon by one or more $R^{16}$;
$R^7$ is selected from $C_{1-6}$alkanoyl, $C_{1-6}$alkylsulphonyl, $C_{2-6}$alkenylsulphonyl, carbocyclyl-$R^{18}$— or heterocyclyl-$R^{19}$—; wherein $R^7$ may be independently optionally substituted on carbon by a group selected from $R^{20}$; and wherein if said heterocyclyl contains an —NH— moiety that nitrogen may be optionally substituted by $R^{21}$;
$R^{14}$ is carbocyclyl;
$R^{16}$ is selected from methoxy;
$R^{18}$ and $R^{19}$ are —C(O)—;
$R^{20}$ is selected from halo, cyano, hydroxy, $C_{1-6}$alkoxy, $C_{2-6}$alkynyloxy, $C_{1-6}$alkanoyloxy, N,N—($C_{1-6}$alkyl)$_2$amino, $C_{1-6}$alkylS(O)$_a$ wherein a is 2 or heterocyclyl; wherein $R^{20}$ may be optionally substituted on carbon by one or more $R^{26}$;

$R^{21}$ is $C_{1-6}$alkyl;
$R^{26}$ is hydroxy;
p is 0;
q is 0;
n is 0 or 1;

or a pharmaceutically acceptable salt or an in vivo hydrolysable ester thereof.

Therefore in a further aspect of the invention there is provided a compound of formula (I) (as depicted above) wherein Ring A is a nitrogen linked 6 membered saturated ring which optionally contains an additional nitrogen atom; wherein if Ring A contains an additional nitrogen atom that nitrogen may be optionally substituted by $R^7$; wherein
$R^7$ is selected from $C_{1-6}$alkanoyl, $C_{1-6}$alkylsulphonyl and $C_{2-6}$alkenylsulphonyl; wherein $R^7$ may be optionally substituted on carbon by a group selected from $R^{20}$; wherein
$R^{20}$ is selected from hydroxy, $C_{1-6}$alkoxy, $C_{1-6}$alkanoyloxy and N,N—($C_{1-6}$alkyl)$_2$amino;
p is 0;
q is 0;
$R^3$ is halo;
n is 0 or 1.
$R^4$ is $C_{1-6}$alkyl or carbocyclyl; wherein $R^4$ may be optionally substituted on carbon by one or more $R^{14}$; wherein
$R^{14}$ is carbocyclyl;
$R^5$ is $C_{1-6}$alkyl; wherein $R^5$ may be optionally substituted on carbon by one or more $R^{16}$; wherein
$R^{16}$ is methoxy; and
$R^6$ is hydrogen.

or a pharmaceutically acceptable salt or an in vivo hydrolysable ester thereof.

Therefore in a further aspect of the invention there is provided a compound of formula (I) (as depicted above) wherein Ring A is 4-methylsulphonylpiperazin-1-yl, 4-vinylsulphonylpiperazin-1-yl, 4-acetylpiperazin-1-yl, 4-(acteoxyacetyl)piperazin-1-yl, 4-(hydroxyacetyl)piperazin-1-yl, 4-(dimethylaminoacetyl)piperazin-1-yl, 4-(2-dimethylaminoethylsulphonyl)piperazin-1-yl, 4-(2-methoxyethylsulphonyl)piperazin-1-yl, 4-(2-hydroxyethylsulphonyl)piperazin-1-yl, piperazin-1-yl or morpholino;
p is 0;
q is 0;
$R^3$ is halo;
n is 0 or 1;
$R^4$ is ethyl, isopropyl, isobutyl, cyclobutyl or cyclopropylmethyl;
$R^5$ is methyl, ethyl, propyl or methoxymethyl; and
$R^6$ is hydrogen;

or a pharmaceutically acceptable salt or an in vivo hydrolysable ester thereof.

In another aspect of the invention, preferred compounds of the invention are any one of the Examples or a pharmaceutically acceptable salt or an in vivo hydrolysable ester thereof.

In another aspect of the invention, preferred compounds of the invention are any one of Examples 18, 22, 87, 92, 94, 96, 104, 113, 118 or 121, or a pharmaceutically acceptable salt or an in vivo hydrolysable ester thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein variable groups are, unless otherwise specified, as defined in formula (I)) comprises of:

Process a) reaction of a pyrimidine of formula (II):

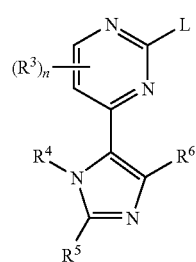
(II)

wherein L is a displaceable group; with an aniline of formula (III):

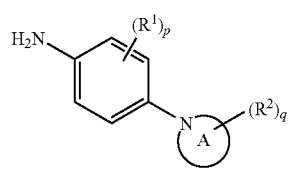
(III)

Process b) reacting a compound of formula (IV):

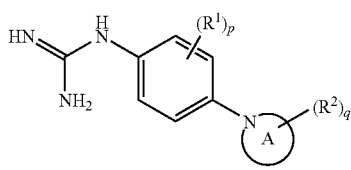
(IV)

with a compound of formula (V):

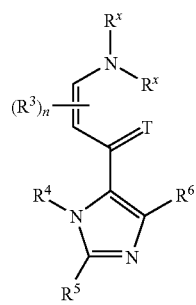
(V)

wherein T is O or S; $R^x$ may be the same or different and is selected from $C_{1-6}$alkyl; or Process c) reacting a pyrimidine of formula (VI):

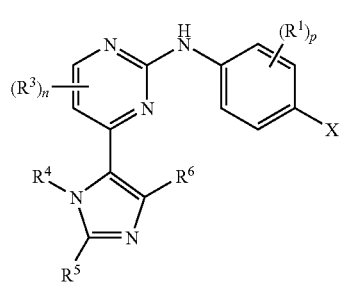
(VI)

wherein X is a displaceable group; with a heterocyclyl of formula (VII):

(VII)

or

Process d) for compounds of formula (I); reacting a pyrimidine of formula (VIII)

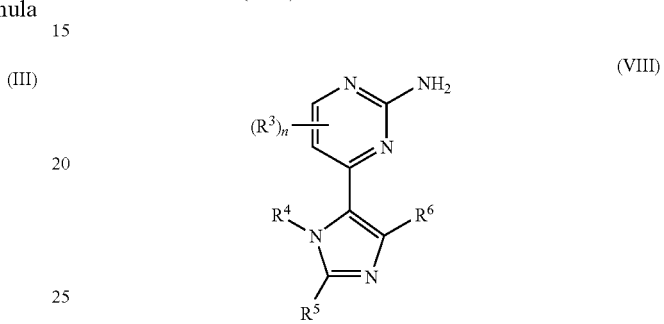
(VIII)

with a compound of formula (IX):

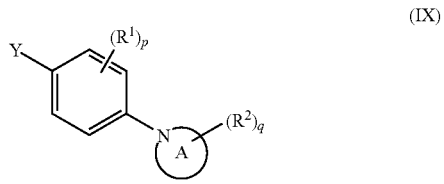
(IX)

where Y is a displaceable group;

and thereafter if necessary:

i) converting a compound of the formula (I) into another compound of the formula (I);

ii) removing any protecting groups;

iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

X is a displaceable group, suitable values for X are for example, a bromo or iodo group. Preferably X is bromo.

Y is a displaceable group, suitable values for Y are for example, a halogeno or sulphonyloxy group, for example a bromo, iodo or trifluoromethanesulphonyloxy group. Preferably Y is iodo.

Specific reaction conditions for the above reactions are as follows.

Process a) Pyrimidines of formula (II) and anilines of formula (III) may be reacted together:

i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) where L is chloro may be prepared according to Scheme 1:

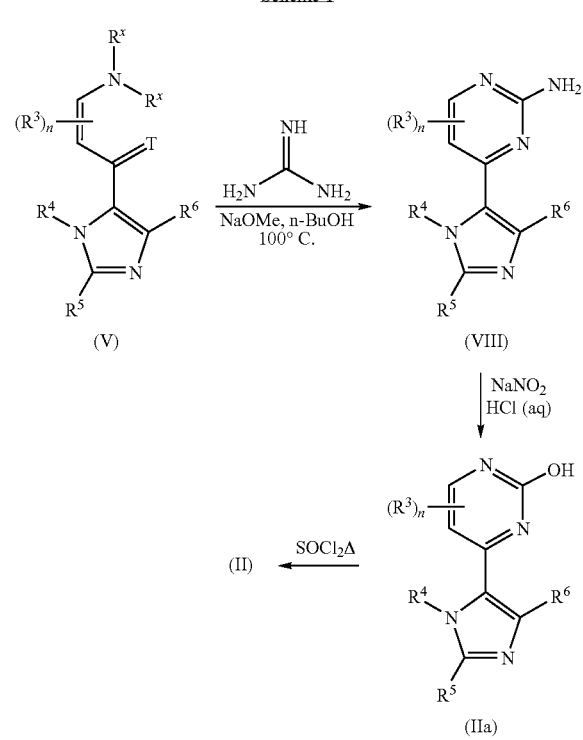

Anilines of formula (III) are commercially available compounds, or they are known in the literature, or they are prepared by standard processes known in the art.

Process b) Compounds of formula (IV) and compounds of formula (V) are reacted together in a suitable solvent such as N-methylpyrrolidinone or butanol at a temperature in the range of 100-200° C., preferably in the range of 150-170° C. The reaction is preferably conducted in the presence of a suitable base such as, for example, sodium hydride, sodium methoxide or potassium carbonate.

Compounds of formula (V) may be prepared according to Scheme 2:

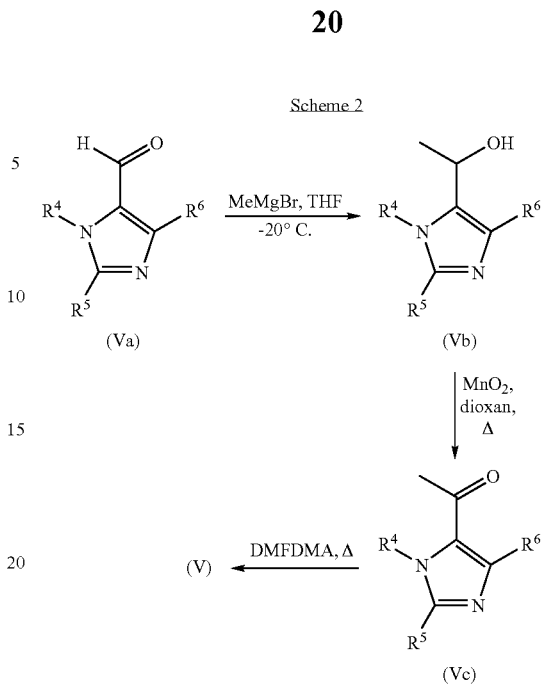

Compounds of formula (IV) and (Va) are commercially available compounds, or they are known in the literature, or they are prepared by standard processes known in the art.

Process c) Compounds of formula (VI) and amines of formula (VII) may be reacted together under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Compounds of formula (VI) may be prepared according to the procedures described in WO 02/20512.

Heterocyclyls of formula (VII) are commercially available compounds, or they are known in the literature, or they are prepared by standard processes known in the art.

Process d) Compounds of formula (VIII) and amines of formula (IX) may be reacted together under standard Buchwald conditions as described in Process a.

The synthesis of compounds of formula (VIII) is described in Scheme 1.

Compounds of formula (IX) are commercially available compounds, or they are known in the literature, or they are prepared by standard processes known in the art.

Amines of formula (VI) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedure set out below:

Assay

The following abbreviations have been used:

HEPES is N-[2-Hydroxyethyl]piperazine-N'-[2-ethanesulfonic acid]

DTT is Dithiothreitol

PMSF is Phenylmethylsulphonyl fluoride

The compounds were tested in an in vitro kinase assay in 96 well format using Scintillation Proximity Assay (SPA-obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.2 μl of CDK2/Cyclin E partially-purified enzyme (amount dependent on enzyme activity) diluted in 25 μl incubation buffer was added to each well then 20 μl of GST-Rb/ATP/ATP33 mixture (containing 0.5 μg GST-Rb and 0.2 μM ATP and 0.14 μCi [γ-33-P]-Adenosine Triphosphate in incubation buffer), and the resulting mixture shaken gently, then incubated at room temperature for 60 minutes.

To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH 7.5, 10 mM MnCl$_2$, 1 mM DTT, 100 μM Sodium vanadate, 100 μM NaF, 10 nM Sodium Glycerophosphate, BSA (1 mg/ml final).

Test Substrate

In this assay only part of the retinoblastoma protein (Science Mar. 13, 1987; 235 (4794):1394-1399; Lee W. H., Bookstein R., Hong F., Young L. J., Shew J. Y., Lee E. Y.) was used, fused to a GST tag. PCR of retinoblastoma gene encoding amino acids 379-928 (obtained from retinoblastoma plasmid ATCC pLRbRNL) was performed, and the sequence cloned into pGEx 2T fusion vector (Smith D. B. and Johnson, K. S. Gene 67, 31 (1988); which contained a tac promoter for inducible expression, internal lac I$^q$ gene for use in any *E. Coli* host, and a coding region for thrombin cleavage—obtained from Pharmacia Biotech) which was used to amplify amino acids 792-928. This sequence was again cloned into pGEx 2T.

The retinoblastoma 792-928 sequence so obtained was expressed in *E. Coli* (BL21 (DE3) pLysS cells) using standard inducible expression techniques, and purified as follows.

*E. coli* paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM $MgCl_2$, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792-927) were pooled and dialysed overnight against kinase buffer. The final product was analysed by Sodium Dodeca Sulfate (SDS) PAGE (Polyacrylamide gel) using 8-16% Tris-Glycine gels (Novex, San Diego, USA).

CDK2 and Cyclin E

The open reading frames of CDK and Cyclin E were isolated by reverse transcriptase-PCR using HeLa cell and activated T cell mRNA as a template and cloned into the insect expression vector pVL1393 (obtained from Invitrogen 1995 catalogue number: V1392-20). CDK2 and cyclin E were then dually expressed [using a standard virus Baculogold co-infection technique] in the insect SF21 cell system (*Spodoptera Frugiperda* cells derived from ovarian tissue of the Fall Army Worm—commercially available).

Example Production of Cyclin E/CDK2

The following Example provides details of the production of Cyclin E/CDK2 in SF21 cells (in TC100+10% FBS(TCS)+ 0.2% Pluronic) having dual infection MOI 3 for each virus of Cyclin E & CDK2.

SF21 cells grown in a roller bottle culture to $2.33 \times 10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Litres of culture was harvested. The total cell count at harvest was 1.58×10E6 cells/ml. (99% viable). The cells were spun out at 2500 rpm, 30 mins., 4° C. in Heraeus Omnifuge 2.0 RS in 250 ml. lots. The supernatant was discarded.

Partial Co-Purification of Cdk2 and Cyclin E

Sf21 cells were resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Biosystems, Hertford, UK). Cdk2 and Cyclin E were coeluted at the beginning of a 0-1M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK1 and CDK4 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at $IC_{50}$ concentrations or doses in the range 250 µM to 1 nM.

When tested in the above in-vitro assay the CDK2 inhibitory activity of Example 8 was measured as $IC_{50}=0.181$ µM.

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1-12). Thus, the following details are provided of measuring inhibition of cell growth:

Cells were plated in appropriate medium in a volume of 100 ml in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% $CO_2$) for three days.

At the end of three days TCA was added to the plates to a final concentration of 16% (v/v). Plates were then incubated at 4° C. for 1 hour, the supernatant removed and the plates washed in tap water. After drying, 100 ml SRB dye (0.4% SRB in 1% acetic acid) was added for 30 minutes at 37° C. Excess SRB was removed and the plates washed in 1% acetic acid. The SRB bound to protein was solubilised in 10 mM Tris pH 7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anticancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

Herein when cancer is referred to, in particular this refers to leukaemia, breast cancer, lung cancer, colon cancer, rectal cancer, stomach cancer, prostate cancer, bladder cancer, cancer of the pancreas, ovarian cancer, liver cancer, kidney cancer, skin cancer and cancer of the vulva.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into, or progression through, the S phase by inhibition of CDK2 and CDK4, especially CDK2, and M phase by inhibition of CDK1.

According to a further feature of the invention, there is provided a compound of the formula (I), or a pharmaceutically acceptable salt or in vivo hydrolysable ester thereof, as defined herein before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of the invention, there is provided the use of a compound of the formula (I), or a pharmaceutically acceptable salt or in vivo hydrolysable ester thereof, as defined herein before in the manufacture of a medicament for use in the treatment of cancer.

According to a further feature of the invention, there is provided the use of a compound of the formula (I), or a pharmaceutically acceptable salt or in vivo hydrolysable ester thereof, as defined herein before in the manufacture of a medicament for use in the production of a CDK inhibitory effect.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into, or progression through, the S phase by inhibition of CDK2 and CDK4, especially CDK2, and M phase by inhibition of CDK1.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of formula (I) or a pharmaceutically acceptable salt or in vivo hydrolysable ester thereof as defined herein before. Particularly, an inhibitory effect is produced by preventing entry into, or progression through, the S phase by inhibition of CDK2 and CDK4, especially CDK2, and M phase by inhibition of CDK1.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of producing a CDK inhibitory effect in a warm-blooded animal, such as man, in need of such treatment which comprises administering to said animal an effective amount of a compound of formula (I) or a pharmaceutically acceptable salt or in vivo hydrolysable ester thereof as defined herein before.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the production of a cell cycle inhibitory (anti-cell-proliferation) effect in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancer in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the production of a CDK inhibitory effect in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; antimetabolites such as methotrexate, 5-fluorouracil, gemcitabine and cytarabine; vinca alkaloids and analogues such as vincristine, vinblastine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:

a) a compound of formula (I), or a pharmaceutically acceptable salt or in vivo hydrolysable ester thereof, in a first unit dosage form;

b) a pharmaceutical agent for treating malignant conditions that is known to cause hair loss; in a second unit dosage form; and c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated; $^{19}F$ NMR is also recorded in DMSO-$d_6$ unless otherwise stated;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(H)^+$;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:
 THF tetrahydrofuran;
 DMF N,N-dimethylformamide;
 DMFDMA dimethylformamide dimethylacetal;
 EtOAc ethyl acetate;
 MeOH methanol;
 EtOH ethanol;
 DIPEA N,N-diisopropylethylamine;
 HATU O-(7-azabenzotriazol-1-yl)-1,1-3,3-tetramethyluronium hexafluorophosphate;
 HOBt 1-hydroxybenzotriazole
 EDAC 1-ethyl-3-(3-dimethylaminopropyl)carbodi-imide hydrochloride ether diethyl ether;
 TFA trifluoroacetic acid;
 DCM dichloromethane; and
 DMSO dimethylsulphoxide.

xvii) where an Isolute SCX-2 column is referred to, this means an "ion exchange" extraction cartridge for adsorption of basic compounds, i.e. a polypropylene tube containing a benzenesulphonic acid based strong cation exchange sorbent, used according to the manufacturers instructions obtained from International Sorbent Technologies Limited, Dyffryn Business Park, Hengeod, Mid Glamorgan, UK, CF82 7RJ;

xviii) where an Isolute amine column is referred to, this means an "ion exchange" extraction cartridge for adsorption of acidic compounds, i.e. a polypropylene tube containing a amino silane covalently bonded to a silica particle used according to the manufacturers instructions obtained from International Sorbent Technologies Limited, Dyffryn Business Park, Hengeod, Mid Glamorgan, UK, CF82 7RJ;

xix) where a Chemelut column is referred to, this means an extraction cartridge for removal of water, i.e. a polypropylene tube containing diatomaceous earth used according to the manufacturers instructions obtained from Varian, Harbor City, Calif., USA; and xx) where HPLC was performed on a Phenomenex column this refers to a Phenomenex 150×21.2 mm Luna 10 micron C18 column using a gradient of 5 to 95 of 0.2% TFA water-acetonitrile over 10 mins at 20 ml/minute flow rate;

xxi) macroporous polystyrene carbonate resin refers to, Argonaut Technologies MP carbonate resin with the capacity 3.0 Mole equivalents per gram of resin available from Argonaut Technologies, New Road, Hengoed, Mid Glamorgan United Kingdom, CF82 8AU.

Example 1

2-[4-(4-Mesylpiperazin-1-yl)anilino]-4-(1-isopropyl-2-methyl-1H-imidazol-5-yl)pyrimidine 2-Amino-4-(1-isopropyl-2-methyl-1H-imidazol-5-yl)pyrimidine (Method 39 of WO 03/076436; 220 mg, 1 mmol), 1-bromo-4-(4-mesylpiperazinyl)benzene (WO 2001062742; 319 mg, 1 mmol), tris(dibenzylideneacetone)dipalladium(0) (23 mg, 2 mol %), 2-(di-tert-butylphosphino)biphenyl (6 mg, 2 mol %) and sodium tert-butoxide (135 mg, 1.4 mmol) in anhydrous 1,4-dioxane (10 ml) was evacuated and refilled with nitrogen (3 times). The reaction was heated under nitrogen at 95° C. overnight before evaporating under reduced pressure. The residue was triturated with EtOAc (20 ml), filtered and re-evaporated to give a gum. Chromatography on silica gel with MeOH:DCM (2:98 to 5:95) gave the title compound as a yellow solid. (70 mg 15%). NMR: 1.39 (d, 6H), 2.47 (s, 3H), 2.92 (s, 3H), 3.17 (m, 4H), 3.26 (m, 4H), 5.70 (septuplet, 1H), 6.92 (d, 2H), 6.94 (d, 1H), 7.39 (s, 1H), 7.48 (d, 2H), 8.32 (d, 1H), 9.18 (s, 1H); m/z 456.

Example 2

2-[4-(4-Mesylpiperazin-1-yl)anilino]-4-(1-isopropyl-2-methyl-1H-imidazol-5-yl)-5-chloropyrimidine The title compound was prepared according to the procedure of Example 1 using 2-amino-5-chloro-4-(1-isopropyl-2-methyl-1H-imidazol-5-yl)pyrimidine (Method 5) heating for 30 hours at 100° C. Chromatography on silica gel with MeOH:DCM (2:98 to 6:94). NMR 1.36 (d, 6H), 2.46 (s, 3H), 2.80 (s, 3H), 3.16 (m, 4H), 3.23 (m, 4H), 4.79 (septuplet, 1H), 6.91 (d, 2H), 7.22 (s, 1H), 7.49 (d, 2H), 8.51 (d, 1H), 9.49 (s, 1H); m/z 490.

Example 3

2-[4-(4-Mesylpiperazin-1-yl)anilino]-4-(1-cyclobutyl-2-methyl-1H-imidazol-5-yl)pyrimidine 5-(3-Dimethylaminoprop-2-en-1-oyl)-1-cyclobutyl-2-methylimidazole (Method 37 of WO 03/076435; 233 mg 1 mmol) and N-{4-[4-(methylsulphonyl)piperazin-1-yl]phenyl}guanidine (Method 1; 390 mg 1.3 mmol) in 2-methoxyethanol (8 ml) was stirred and heated for 18 hours at 110° C. The reaction mixture was evaporated under reduced pressure and the residue purified by chromatography on silica gel with MeOH:DCM (3:97 to 8:92). After evaporation and trituration with ether, the title compound was obtained as a yellow solid. (227 mg 48.5%). NMR: 1.60-1.71 (2×m, 2H), 2.36 (m, 4H), 2.49 (s, 3H), 2.91 (s, 3H), 3.18 (m, 4H), 3.25 (m, 4H), 5.51 (quintet, 1H), 6.91 (d, 1H), 6.97 (d, 2H), 7.30 (s, 1H), 7.54 (d, 2H), 8.33 (d, 1H), 9.23 (s, 1H); m/z 468.

Examples 4-17

The following compounds were prepared by the procedure of Example 3 using the appropriate imidazole and N-{4-[4-(methylsulphonyl)piperazin-1-yl]phenyl}guanidine (Method 1) or N-[4-(4-acetylpiperazin-1-yl)phenyl]guanidine bicarbonate salt (Method 2).

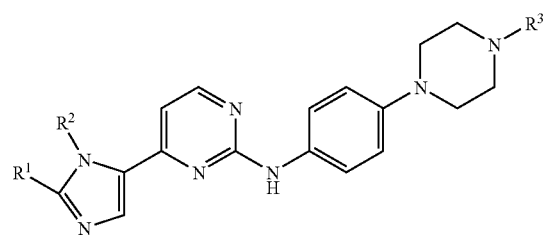

| Ex | $R^1$ | $R^2$ | $R^3$ | NMR | m/z | SM |
|---|---|---|---|---|---|---|
| 4[1] | Me | Cyclopropylmethyl | MeSO$_2$— | 0.09 (m, 2H), 0.28 (m, 2H), 1.00 (m, 1H), 2.39 (s, 3H), 2.92 (s, 3H), 3.18 (m, 4H), 3.24 (m, 4H), 4.49 (d, 2H), 6.94 (d, 2H), 7.02 (d, 1H), 7.47 (d, 2H), 7.58 (s, 1H), 8.30 (d, 1H), 9.15 (s, 1H) | 468 | Meth 41 in WO 03/076435 |

-continued

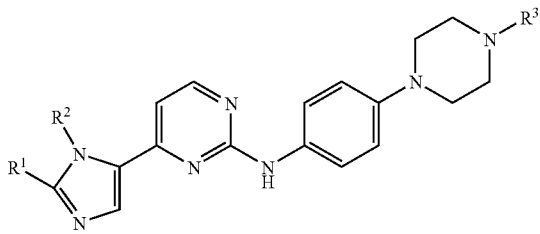

| Ex | R¹ | R² | R³ | NMR | m/z | SM |
|---|---|---|---|---|---|---|
| 5[2] | Et | Et | MeSO$_2$— | 1.11 (t, 3H), 1.24 (t, 3H), 2.71 (q, 2H), 2.91 (s, 3H), 3.18 (m, 4H), 3.23 (m, 4H), 4.50 (q, 2H), 6.95 (d, 2H), 7.03 (d, 1H), 7.47 (d, 2H), 7.61 (s, 1H), 8.28 (d, 1H), 9.12 (s, 1H) | 456 | Meth 55 of WO 03/076434 |
| 6[3] | Et | i-Pr | MeSO$_2$— | 1.28 (t, 3H), 1.40 (d, 6H), 2.79 (q, 2H), 2.91 (s, 3H), 3.17 (m, 4H), 3.24 (m, 4H), 5.61 (septuplet, 1H), 6.93 (d, 2H), 6.94 (d, 1H), 7.40 (s, 1H), 7.49 (d, 2H), 8.32 (d, 1H), 9.18 (s, 1H) | 470 | Meth 9 |
| 7[4] | MeOCH$_2$— | i-Pr | MeSO$_2$— | 1.42 (d, 6H), 2.92 (s, 3H), 3.17 (m, 4H), 3.24 (m, 4H), 3.27 (s, 3H), 4.53 (s, 2H), 5.52 (septuplet, 1H), 6.94 (d, 2H), 6.99 (d, 1H), 7.47 (s, 1H), 7.49 (d, 2H), 8.38 (d, 1H), 9.21 (s, 1H) | 486 | Meth 50 of WO 03/076434 |
| 8[5] | Pr | Et | MeSO$_2$— | 0.97 (t, 3H), 1.12 (t, 3H), 1.72 (sextuplet, 2H), 2.68 (t, 2H), 2.92 (s, 3H), 3.16 (m, 4H), 3.27 (m, 4H), 4.51 (q, 2H), 6.93 (d, 2H), 7.02 (d, 1H), 7.48 (d, 2H), 7.62 (s, 1H), 8.29 (d, 1H), 9.12 (s, 1H) | 470 | Meth 13 |
| 9[6] | Me | Et | MeSO$_2$— | 1.12 (t, 3H), 2.38 (s, 3H), 2.91 (s, 3H), 3.17 (m, 4H), 3.24 (m, 4H), 4.50 (q, 2H), 6.94 (d, 2H), 7.02 (d, 1H), 7.48 (d, 2H), 7.60 (s, 1H), 8.29 (d, 1H), 9.13 (s, 1H) | 442 | Meth 16 of WO 02/20512 |
| 10[7] | Me | i-Bu | MeSO$_2$— | 0.60 (d, 6H), 1.69 (septuplet, 1H), 2.36 (s, 3H), 2.92 (s, 3H), 3.16 (m, 4H), 3.25 (m, 4H), 4.32 (d, 2H), 6.94 (d, 2H), 7.01 (d, 1H), 7.47 (d, 2H), 7.58 (s, 1H), 8.29 (d, 1H), 9.18 (s, 1H) | 470 | Meth 29 of WO 03/076436 |
| 11[8] | Et | i-Pr | MeC(O)— | 1.28 (t, 3H), 1.40 (d, 6H), 2.02 (s, 3H), 2.79 (q, 2H), 3.00 (t, 2H), 3.08 (t, 2H), 3.57 (m, 4H), 5.60 (septuplet, 1H), 6.91 (d, 2H), 6.94 (d, 1H), 7.41 (s, 1H), 7.48 (d, 2H), 8.31 (d, 1H), 9.18 (s, 1H) | 434 | Meth 9 |
| 12 | Pr | Et | MeC(O)— | 0.95 (t, 3H), 1.10 (t, 3H), 1.70 (septuplet, 2H), 2.02 (s, 3H), 2.68 (t, 2H), 3.01 (t, 2H), 3.08 (t, 2H), 3.59 (q, 4H), 4.51 (q, 2H), 6.92 (d, 2H), 7.02 (d, 1H), 7.44 (d, 2H), 7.62 (s, 1H), 8.29 (d, 1H), 9.11 (s, 1H) | 434 | Meth 13 |

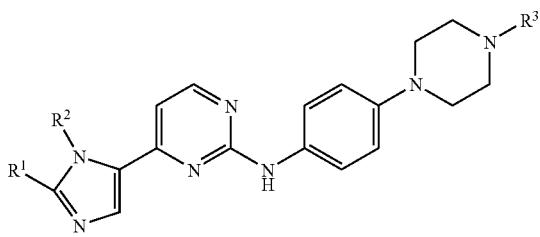

| Ex | R$^1$ | R$^2$ | R$^3$ | NMR | m/z | SM |
|---|---|---|---|---|---|---|
| 13 | Me | Cyclobutyl | MeC(O)— | 1.60 (sextet, 1H), 1.73 (q, 1H), 2.05 (s, 3H), 2.30-2.48 (m, 4H), 3.031 (t, 2H), 3.09 (t, 2H), 3.59 (q, 4H), 5.58 (quintet, 1H), 6.93 (d, 1H), 6.96 (d, 2H), 7.32 (s, 1H), 7.57 (d, 2H), 8.34 (d, 1H), 9.24 (s, 1H) | 432 | Meth 37 of WO 03/076435 |
| 14 | Et | Et | MeC(O)— | 1.12 (t, 3H), 1.24 (t, 3H), 2.03 (s, 3H), 2.71 (q, 2H), 3.01 (t, 2H), 3.08 (t, 2H), 3.57 (q, 4H), 4.49 (q, 2H), 6.92 (d, 2H), 7.01 (d, 1H), 7.45 (d, 2H), 7.61 (s, 1H), 8.29 (d, 1H), 9.10 (s, 1H) | 420 | Meth 55 of WO 03/076434 |
| 15 | Me | Et | MeC(O)— | 1.11 (t, 3H), 2.03 (s, 3H), 2.38 (s, 3H), 3.02 (t, 2H), 3.08 (t, 2H), 3.57 (q, 4H), 4.50 (q, 2H), 6.92 (d, 2H), 7.01 (d, 1H), 7.46 (d, 2H), 7.59 (s, 1H), 8.28 (d, 1H), 9.09 (s, 1H) | 406 | Meth 16 of WO 02/20512 |
| 16[9] | MeOCH$_2$— | i-Pr | MeC(O)— | 1.42 (d, 6H), 2.03 (s, 3H), 3.01 (t, 2H), 3.08 (t, 2H), 3.27 (s, 3H), 3.57 (q, 4H), 4.53 (s, 2H), 5.52 (septuplet, 1H), 6.91 (d, 2H), 6.99 (d, 1H), 7.44 (s, 1H), 7.47 (d, 2H), 8.38 (d, 1H), 9.20 (s, 1H) | 450 | Meth 50 of WO 03/076434 |
| 17[10] | Me | i-Bu | MeC(O)— | 0.60 (d, 6H), 1.69 (septuplet, 1H), 2.02 (s, 3H), 2.35 (s, 3H), 2.99 (t, 2H), 3.07 (t, 2H), 3.58 (q, 4H), 4.33 (d, 2H), 6.93 (d, 2H), 7.00 (d, 1H), 7.45 (d, 2H), 7.58 (s, 1H), 8.28 (d, 1H), 9.13 (s, 1H) | 434 | Meth 29 of WO 03/076436 |

[1] This compound required further chromatography on neutral alumina (activity II) eluting with EtOAc:DCM (1:1) then EtOAc:DCM (1:1) with 5% v/v MeOH. The title compound was crystallised from MeOH. (120 mg 25.6%).
[2] Chromatography with MeOH:DCM (2:98 to 6:94). The title compound was crystallised from acetonitrile. (149 mg 32.7%)
[3] Chromatography with MeOH:DCM (3:97 to 5:95). (127 mg 27%).
[4] Chromatography with MeOH:DCM (3:97). (180 mg 37%).
[5] Chromatography with MeOH:DCM (2:98 to 6:94). (290 mg 34.5%).
[6] Chromatography with MeOH:DCM (2:98 to 6:94). (340 mg 38.5%).
[7] Chromatography with MeOH:DCM (2:98 to 6:94). (350 mg 41.7%).
[8] 5-(3-Dimethylaminoprop-2-en-1-oyl)-1-isopropyl-2-ethylimidazole (Method 9; 470 mg 2 mmol) and N-[4-(4-acetylpiperazin-1-yl)phenyl]guanidine bicarbonate salt (Method 2; 740 mg 2.3 mmol) in 2-methoxyethanol (10 ml) was stirred and heated for 24 hours at 110° C. The reaction mixture was evaporated under reduced pressure and the residue purified by chromatography on silica gel with MeOH:DCM (2:98 to 6:94). After evaporation and trituration with ether, the title compound was obtained as a yellow solid. (290 mg 33.4%).
[9] Chromatography with MeOH:DCM (3:97 to 8:92). (186 mg 20.7%).
[10] Chromatography with MeOH:DCM (2:98 to 6:94). (372 mg 40%).

Example 18

2-[4-(4-Acetylpiperazin-1-yl)anilino]-4-(1-isopropyl-2-methyl-1H-imidazol-5-yl)pyrimidine (2E)-3-(Dimethylamino)-1-(1-isopropyl-2-methyl-1H-imidazol-5-yl)prop-2-en-1-one (Method 24 of WO 03/076436; 140 mg 0.63 mmol) and N-[4-(4-acetylpiperazin-1-yl)phenyl]guanidine bicarbonate salt (Method 2; 240 mg 0.74 mmol) in 2-methoxyethanol (4 ml) were reacted under nitrogen under microwave conditions at 200° C. for 30 minutes. After evaporation under reduced pressure, chromatography on silica gel with MeOH:DCM (2:98 to 6:94) gave the title compound, after ether trituration, as a yellow solid. (85 mg 31.5%). NMR: 1.39 (d, 6H), 2.02 (s, 3H), 2.45 (s, 3H), 3.00 (b t, 2H), 3.06 (b t, 2H), 3.56 (b q, 4H), 5.70 (septuplet, 1H), 6.91 (d, 2H), 6.95 (d, 1H), 7.38 (s, 1H), 7.46 (d, 2H), 8.31 (d, 1H), 9.15 (s, 1H); m/z 420.

Example 19

2-[4-(4-Acetylpiperazin-1-yl)anilino]-4-[1-(cyclopropylmethyl)-2-methyl-1H-imidazol-5-yl]pyrimidine The title compound was prepared by the procedure of Example 18 from 5-(3-dimethylaminoprop-2-en-1-oyl)-1-cyclopropylmethyl-2-methylimidazole (Method 41 in WO 03/076435) except that the reaction was heated in microwave at 200° C. for 40 minutes. 148 mg 53.4%. NMR: 0.10 (m, 2H), 0.28 (m, 2H), 1.02 (m, 1H), 2.03 (s, 3H), 2.38 (s, 3H), 3.01 (t, 2H), 3.08 (t, 2H), 3.57 (q, 4H), 4.48 (d, 2H), 6.92 (d, 2H), 7.01 (d, 1H), 7.43 (d, 2H), 7.57 (s, 1H), 8.281 (d, 1H), 9.12 (s, 1H); m/z 432.

Example 20

2-[4-(Piperazin-1-yl)anilino]-4-(1-isopropyl-2-methyl-1H-imidazol-5-yl)pyrimidine 2-[4-(4-Acetylpiperazin-1-yl)anilino]-4-(1-isopropyl-2-methyl-1H-imidazol-5-yl)pyrimidine (Example 18; 1.3 g) was stirred and heated in isopropanol (15 ml) and 33% hydrochloric acid (1.5 ml) at 90° C. for 4.5 hours. The reaction was evaporated under reduced pressure and then basified with 7N ammonia in MeOH and re-evaporated. Toluene was added and the mixture was re-evaporated (3 times). The residue was purified by chromatography on neutral alumina, activity II eluting with MeOH:DCM (5:95) to give the title compound as a yellow gum. (330 mg 28%). NMR: 1.40 (d, 6H), 2.46 (s, 3H), 2.82 (m, 4H), 2.96 (m, 4H), 5.69 (septuplet, 1H), 6.85 (d, 2H), 6.93 (d, 1H), 7.18 (s, 1H), 7.42 (d, 2H), 8.30 (d, 1H), 9.11 (s, 1H); m/z 378.

Example 21

2-{4-[4-(2-Acetoxyacetyl)piperazin-1-yl]anilino}-4-(1-isopropyl-2-methyl-1H-imidazol-5-yl)pyrimidine 2-[4-(Piperazin-1-yl)anilino]-4-(1-isopropyl-2-methyl-1H-imidazol-5-yl)pyrimidine (Example 20; 330 mg 0.88 mmol) was stirred in DCM (6 ml) at room temperature. Triethylamine was added (153 mg 1.51 mmol) followed by dropwise addition of acetoxyacetylchloride (143 mg 1.05 mmol). After stirring for 1.25 hours, DCM (10 ml) and brine (5 ml) were added. The reaction was stirred vigorously for 10 minutes then the organic layers were separated, dried and evaporated under reduced pressure to give the title compound as a yellow foam. Quantitative yield. The solid was triturated with ether and re-evaporated. NMR: 1.40 (d, 6H), 2.08 (s, 3H), 2.48 (s, 3H), 3.05 (b d, 4H), 3.54 (b d, 4H), 4.81 (s, 2H), 5.70 (septuplet, 1H), 6.92 (d, 2H), 6.95 (d, 1H), 7.40 (s, 1H), 7.48 (d, 2H), 8.31 (d, 1H), 9.18 (s, 1H); m/z 478.

Example 22

2-{4-[4-(2-Hydroxyacetyl)piperazin-1-yl]anilino}-4-(1-isopropyl-2-methyl-1H-imidazol-5-yl)pyrimidine 2-{4-[4-(2-Acetoxyacetyl)piperazin-1-yl]anilino}-4-(1-isopropyl-2-methyl-1H-imidazol-5-yl)pyrimidine (Example 21; 330 mg) was stirred in MeOH (5 ml) at room temperature and 7N ammonia in MeOH (1.6 ml) was added. After 28 hours, the reaction was evaporated under reduced pressure. Chromatography on silica gel using MeOH:DCM (4:96 to 5:95), yielded the title compound as a yellow solid. (108 mg 36%). NMR: 1.39 (d, 6H), 2.46 (s, 3H), 3.05 (b s, 4H), 3.48 (b s, 2H), 3.61 (b s, 2H), 4.12 (d, 2H), 4.57 (t, 1H), 5.69 (septuplet, 1H), 6.92 (d, 2H), 6.95 (d, 1H), 7.38 (s, 1H), 7.47 (d, 2H), 8.31 (d, 1H), 9.15 (s, 1H); m/z 436.

Example 23

2-{4-[4-(2-Dimethylaminoacetyl)piperazin-1-yl]anilino}-4-(1-isopropyl-2-methyl-1H-imidazol-5-yl)pyrimidine Chloroacetyl chloride (50 μl, 0.65 mmol) was added dropwise to a stirred solution of 2-[4-(piperazin-1-yl)anilino]-4-(1-isopropyl-2-methyl-1H-imidazol-5-yl)pyrimidine (Example 20; 200 mg, 0.53 mmol) and triethylamine (90 μl, 0.65 mmol) in DCM (5 ml) at room temperature. After 50 minutes, 2M dimethylamine in THF solution (2 ml, 4 mmol) was added and the reaction was stirred for 5 hours before evaporating under reduced pressure. Chromatography on neutral alumina (activity II) with MeOH:DCM (1:99 to 3:97) gave material which required further purification on silica gel with MeOH:DCM:7N NH₃MeOH (3:97:0.0025 to 10:90:0.0025) to give the title compound as a yellow foam. (150 mg 60% yield). NMR: 1.39 (d, 6H), 2.19 (s, 6H), 2.46 (s, 3H), 3.02 (b t, 2H), 3.06 (b t, 2H), 3.59 (b t, 2H), 3.68 (b t, 2H), 5.69 (septuplet, 1H), 6.92 (d, 2H), 6.94 (d, 1H), 7.39 (s, 1H), 7.47 (d, 2H), 8.31 (d, 1H), 9.17 (s, 1H); m/z 463.

Example 24

2-{4-[4-(Chloroacetyl)piperazin-1-yl]anilino}-4-(1-isopropyl-2-methyl-1H-imidazol-5-yl)pyrimidine 2-[4-(Piperazin-1-yl)anilino]-4-(1-isopropyl-2-methyl-1H-imidazol-5-yl)pyrimidine (Example 20; 1.89 g, 5 mmol), di-isopropylethylamine (0.956 ml, 5.5 mmol) in DCM (25 ml) was treated at 0° C. with chloroacetyl chloride (0.438 ml, 5.5 mmol). The mixture was stirred at ambient for 2 hours, diluted with DCM (25 ml), washed with aqueous saturated sodium bicarbonate solution (20 ml) and aqueous saturated sodium chloride solution (20 ml). The solution was dried and evaporated at reduced pressure to give the title compound, (1.96 g, 87%). NMR (CDCl₃) 8.30 (d, 1H), 7.44 (d, 2H), 7.35 (s, 1H), 6.96 (s, 1H), 6.92 (d, 1H), 6.85 (d, 1H), 5.68-5.56 (m, 1H), 4.12 (s, 2H), 3.83-3.76 (m, 2H), 3.72-3.67 (m, 2H), 3.22-3.11 (m, 4H), 2.59 (s, 3H), 1.48 (d, 6H); m/z 454.

Example 25

2-{4-[4-(Azetidin-1-ylacetyl)piperazin-1-yl]anilino}-4-(1-isopropyl-2-methyl-1H-imidazol-5-yl)pyrimidine hydrochloride 2-{4-[4-(Chloroacetyl)piperazin-1-yl]anilino}-4-(1-isopropyl-2-methyl-1H-imidazol-5-yl)pyrimidine (Example 24; 0.34 g, 0.75 mmol) and azetidine (2 ml) was stirred for 24 hours at ambient temperature. The solution was diluted with EtOAc (20 ml), washed with aqueous saturated sodium bicarbonate solution (10 ml) and aqueous saturated sodium chloride solution (10 ml), then dried and evaporated at reduced pressure. The residue was purified by chromatography on a 40 g silica column, eluted with a 3% MeOH-ammonia/DCM to 5% MeOH-ammonia/DCM gradient, to give the amine, which was converted to the hydrochloride salt by dissolving in EtOAc (3 ml) and treating with a 1.0 molar solution of ethereal-HCl (0.75 ml). The solid was triturated with ether (20 ml) and filtered to give the title compound (24 mg, 7%). NMR: 9.77 (s, 1H), 8.58 (d, 1H), 8.20 (s, 1H), 7.61 (d, 2H), 7.35-7.24 (m, 2H), 7.13 (d, 1H), 5.64-5.55 (m, 1H), 4.65 (brs, 1H), 4.44 (d, 2H), 4.23-4.11 (m, 2H), 4.09-3.96 (m, 2H), 3.81-3.71 (m, 2H), 3.69-3.59 (m, 2H), 3.42-3.31 (m, 2H), 3.30-3.17 (m, 2H), 2.48-2.24 (m, 2H), 2.81 (s, 3H), 1.48 (d, 6H); m/z 475.

Examples 26-28

The following salts were prepared using the procedure of Example 25 from 2-{4-[4-(chloroacetyl)piperazin-1-yl]anilino}-4-(1-isopropyl-2-methyl-1H-imidazol-5-yl)pyrimidine Example 24) and the appropriate amine.

Example 29

2-{4-[4-(Vinylsulphonyl)piperazin-1-yl]anilino}-4-(1-isopropyl-2-methyl-1H-imidazol-5-yl)pyrimidine 2-[4-(Piperazin-1-yl)anilino]-4-(1-isopropyl-2-methyl-1H-imidazol-5-yl)pyrimidine (Example 20; 370 mg 0.98 mmol) was stirred in DCM (10 ml) at room temperature. Triethylamine (150 mg 1.49 mmol) was added followed by dropwise addition of 2-chloro-1-ethanesulphonyl chloride (196 mg 1.2 mmol) in DCM (1 ml). After stirring for 1.25 hours, the reaction was evaporated under reduced pressure and triturated with ether. The resulting solid was treated with water (15 ml), the basified with saturated sodium hydrogen carbonate solution and extracted into DCM (2×20 ml). The organics were washed with brine (10 ml), dried and evaporated to give a gum. After chromatography on silica gel using MeOH:DCM (3:97 to 5:95), the title compound was obtained as a yellow solid (140 mg 30.4%). NMR 1.39 (d, 6H), 2.46 (s, 3H), 3.16 (s, 8H), 5.68 (septuplet, 1H), 6.20 (d, 1H), 6.85 (dd, 1H), 6.91 (d, 2H), 6.95 (d, 1H), 7.38 (s, 1H), 7.47 (d, 2H), 8.30 (d, 1H), 9.16 (s, 1H); m/z 468.

Example 30

2-{4-[4-(2-Dimethylaminoethylsulphonyl)piperazin-1-yl]anilino}-4-(1-isopropyl-2-methyl-1H-imidazol-5-yl)pyrimidine Dimethylamine (2.0 M) in THF (1.5 ml) was added to a stirred suspension of 2-{4-[4-(vinylsulphonyl)piperazin-1-yl]anilino}-4-(1-isopropyl-2-methyl-1H-imidazol-5-yl)pyrimidine (Example 29; 140 mg 0.3 mmol) in THF (3 ml) at room temperature. Additional dimethylamine solution (0.5

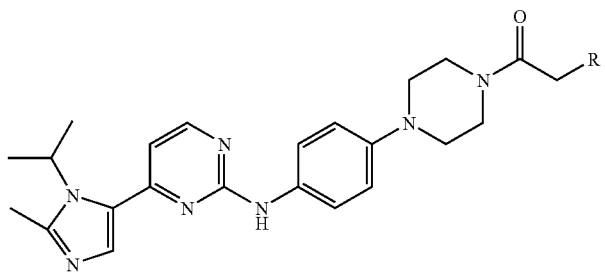

| Ex | R | NMR | m/z | Salt |
|---|---|---|---|---|
| 26 | pyrrolidinyl | 10.29 (brs, 1H), 9.91 (s, 1H), 8.60 (d, 1H), 8.23 (s, 1H), 7.68 (d, 2H), 7.53-7.42 (m, 2H), 7.17 (d, 1H), 5.65-5.56 (m, 1H), 4.48 (d, 2H), 3.94 (s, 2H), 3.80 (s, 2H), 3.64-3.53 (m, 2H), 3.51 (s, 2H), 3.41-3.31 (m, 2H), 3.18-3.02 (m, 2H), 2.83 (s, 3H), 2.06-1.84 (m, 4H), 1.49 (d, 6H) | 489 | HCl |
| 27 | morpholinyl | 9.90 (s, 1H), 8.60 (d, 1H), 8.22 (s, 1H), 7.66 (d, 2H), 7.48-7.37 (m, 2H), 7.16 (d, 1H), 5.65-5.55 (m, 1H), 4.99 (s, 2H), 4.53 (s, 1H), 4.01-3.70 (m, 8H), 3.51-3.41 (m, 4H), 3.38-3.31 (m, 2H), 3.27-3.12 (m, 2H), 2.82 (s, 3H), 1.49 (d, 6H) | 505 | HCl |
| 28 | N(Et)$_2$ | 9.98 (s, 1H), 9.57 (s, 1H), 8.61 (d, 1H), 8.23 (s, 1H), 7.71 (d, 2H), 7.52 (d, 2H), 7.18 (d, 1H), 5.65-5.56 (m, 1H), 4.38 (d, 2H), 3.98-3.78 (m, 4H), 3.55-3.37 (m, 4H), 3.24-3.12 (m, 4H), 2.83 (s, 3H), 1.50 (d, 6H), 1.24 (t, 6H) | 491 | HCl | ml) was added after 2 hours. The reaction was stirred for 1 hour then stood overnight. The reaction was evaporated under reduced pressure, triturated with ether and filtered to give the title compound as a yellow solid. (134 mg 89%). NMR: 1.40 (d, 6H), 2.46 (s, 3H), 2.62 (t, 2H), 3.13 (t, 4H), 3.20-3.35 (2H and 4H)[under exchangeables], 5.68 (septuplet, 1H), 6.92 (d, 2H), 6.95 (d, 1H), 7.38 (s, 1H), 7.47 (d, 2H), 8.31 (d, 1H), 9.18 (s, 1H) [+duetero acetic acid: 3.01 (b d, 2H), 3.14 (t, 4H), 3.33 (t, 4H), 3.37 (m, 2H)]; m/z 478.

Example 31

2-{4-[4-(2-Methoxyethylsulphonyl)piperazin-1-yl]anilino}-4-(1-isopropyl-2-methyl-1H-imidazol-5-yl)pyrimidine Sodium methoxide (40 mg 0.74 mmol) was added to 2-{4-[4-(vinylsulphonyl)piperazin-1-yl]anilino}-4-(1-isopropyl-2-methyl-1H-imidazol-5-yl)pyrimidine (Example 29; 300 mg 0.64 mmol) in MeOH (4 ml). After stirring at room temperature for 5 hours, the reaction was evaporated. After chromatography on silica gel using MeOH:DCM:EtOAc (5:47.5:47.5) and trituration with ether, the title compound was obtained as a yellow solid. NMR: 1.41 (d, 6H), 2.47 (s, 3H), 3.13 (m, 4H), 3.26 (4H alongside exchangeables), 3.37 (t, 2H), 3.67 (t, 2H), 5.69 (septuplet, 1H), 6.93 (d, 2H), 6.96 (d, 1H), 7.39 (s, 1H), 7.49 (d, 2H), 8.32 (d, 1H), 9.18 (s, 1H); m/z 500.

Example 32

2-{4-[4-(2-Hydroxyethylsulphonyl)piperazin-1-yl]anilino}-4-(1-isopropyl-2-methyl-1H-imidazol-5-yl)pyrimidine A mixture of 2-{4-[4-(vinylsulphonyl)piperazin-1-yl]anilino}-4-(1-isopropyl-2-methyl-1H-imidazol-5-yl) pyrimidine (Example 29; 260 mg 0.56 mmol) and barium hydroxide (560 mg 3.27 mmol) in water (10 ml) was heated at 65° C.-90° C. over 6 hours. 1,4-dioxane (1 ml) was added after 1, 2, 3 and 5 hours. After evaporation under reduced pressure, the residue was treated with water (10 ml) and saturated sodium hydrogen carbonate solution (10 ml). The suspension was extracted with DCM (30 ml and 2×20 ml) and EtOAc (25 ml). Both extracts were washed (separately) with brine (10 ml) and dried ($Na_2SO_4$). The extracts were combined and evaporated. After chromatography on silica gel using MeOH:DCM (4:96 to 8:92), the title compound was obtained as a yellow solid (108 mg 40%). NMR: 1.40 (d, 6H), 2.49 (s, 3H), 3.13 (m, 4H), 3.23 (t, 2H), 3.30 (m, 4H), 3.76 (q, 2H), 5.01 (t, 1H), 5.69 (septuplet, 1H), 6.93 (d, 2H), 6.96 (d, 1H), 7.39 (s, 1H), 7.48 (d, 2H), 8.31 (d, 1H), 9.18 (s, 1H); m/z 486.

Example 33

2-[4-(4-Acetylpiperazin-1-yl)anilino]-4-(1-isopropyl-2-methyl-1H-imidazol-5-yl)-5-chloropyrimidine (2E)-2-Chloro-3-(dimethylamino)-1-(1-isopropyl-2-methyl-1H-imidazol-5-yl)prop-2-en-1-one (1.68 g from Method 3-assumed 5 mmol) and N-[4-(4-acetylpiperazin-1-yl)phenyl]guanidine bicarbonate salt (Method 2) (1.94 g 6 mmol) in 2-methoxyethanol (25 ml) were heated under nitrogen at 110° C. for 3.5 hours before evaporation under reduced pressure. The residue was purified by chromatography on silica gel with MeOH:DCM (3:97 to 5:95) to give the title compound, after trituration with ether, as a foam. NMR: 1.36 (d, 6H), 2.02 (s, 3H), 2.48 (s, 3H), 3.00 (b t, 2H), 3.08 (b t, 2H), 3.56 (b q, 4H), 4.80 (septuplet, 1H), 6.90 (d, 2H), 7.21 (s, 1H), 7.47 (d, 2H), 8.50 (s, 1H), 9.48 (s, 1H); m/z 454.

Example 34

2-[4-(Piperazin-1-yl)anilino]-4-(1-isopropyl-2-methyl-1H-imidazol-5-yl)-5-chloropyrimidine The title compound was prepared from 2-[4-(4-acetylpiperazin-1-yl)anilino]-4-(1-isopropyl-2-methyl-1H-imidazol-5-yl)-5-chloropyrimidine (Example 33; 800 mg) by the method of Example 20. Except that after purification by chromatography on neutral alumina, activity II eluting with MeOH:DCM (3:97) the title compound was isolated as a yellow gum. Trituration with ether gave a foam (50 mg 7%). NMR: 1.34 (d, 6H), 2.45 (s, 3H), 2.82 (m, 4H), 2.96 (m, 4H), 4.82 (septuplet, 1H), 6.85 (d, 2H), 7.41 (s, 1H), 7.42 (d, 2H), 8.49 (s, 1H), 9.43 (s, 1H); m/z 412.

Example 35

2-{4-[4-(Acetoxyacetyl)piperazin-1-yl]anilino}-4-(1-isopropyl-2-methyl-1H-imidazol-5-yl)-5-chloropyrimidine The title compound was prepared using the procedure of Example 21 using 400 mg 0.97 mmol of 2-[4-(piperazin-1-yl)anilino]-4-(1-isopropyl-2-methyl-1H-imidazol-5-yl)-5-chloropyrimidine (Example 34). After work-up, the mixture was purified by chromatography on silica gel using MeOH:DCM (3:97 to 6:94) to give a solid (230 mg). NMR: 1.35 (d, 6H), 2.08 (s, 3H), 2.48 (s, 3H), 3.04 (b d, 4H), 3.52 (b d, 4H), 4.80 (septuplet, 1H), 4.81 (s, 2H), 6.92 (d, 2H), 7.22 (s, 1H), 7.48 (d, 2H), 8.51 (d, 1H), 9.49 (s, 1H); m/z 512.

Example 36

2-{4-[4-(Hydroxyacetyl)piperazin-1-yl]anilino}-4-(1-isopropyl-2-methyl-1H-imidazol-5-yl)-5-chloropyrimidine 2-{4-[4-(Acetoxyacetyl)piperazin-1-yl]anilino}-4-(1-isopropyl-2-methyl-1H-imidazol-5-yl)-5-chloropyrimidine (Example 35) was deprotected by the procedure of Example 22. The reaction mixture was evaporated under reduced pressure. The residue was dissolved in DCM (30 ml), washed with water (15 ml) and brine (15 ml), dried and evaporated. The residue was triturated with ether and re-evaporated to give the title compound as a solid (180 mg). NMR: 1.34 (d, 6H), 2.48 (s, 3H), 3.03 (b s, 4H), 3.52 (b d, 4H), 4.11 (d, 2H), 4.59 (t, 1H), 4.80 (septuplet, 1H), 6.91 (d, 2H), 7.21 (s, 1H), 7.47 (d, 2H), 8.51 (s, 1H), 9.49 (s, 1H); m/z 470.

Example 37

2-{4-[4-(2-Hydroxy-2-methylpropionyl)piperazin-1-yl]anilino}-4-(1-isopropyl-2-methyl-1H-imidazol-5-yl)-5-chloropyrimidine 2-Hydroxyisobutyric acid (162 mg. 1 mmol) was added to a solution of 1,1'-carbonyldiimidazole (162 mg. 1 mmol) in DCM (4 ml) and stirred at room temperature for 15 minutes. A solution of 2-[4-(piperazin-1-yl)anilino]-4-(1-isopropyl-2-methyl-1H-imidazol-5-yl)-5-chloropyrimidine (Example 34. 400 mg. 0.97 mmol) in DCM (8 ml) was added and stirring continued for 19 hours. DCM (25 ml) was added and the organic layer was washed with 5% (v/v) acetic acid (15 ml), water (15 ml), brine (15 ml) and dried before evaporating under reduced pressure. Chromatography on silica gel with MeOH:DCM (4:96 to 8:92) gave the title compound, after ether trituration, as a solid. (67 mg 14%). NMR: (500 MHz) 1.30 (d, 6H), 1.34 (d, 6H), 2.48 (s, 3H), 3.04 (t, 4H), 3.62 (b s, 4H), 4.00 (b s, 4H), 4.79 (septuplet, 1H), 5.41 (s, 1H), 6.90 (d, 2H), 7.22 (s, 1H), 7.48 (d, 2H), 8.51 (s, 1H), 9.49 (s, 1H); m/z 498.

Example 38

2-{4-[4-(2-(S)-2-Hydroxypropionyl)piperazin-1-yl]anilino}-4-(1-isopropyl-2-methyl-1H-imidazol-5-yl)-5-chloropyrimidine To a solution of 2-[4-(piperazin-1-yl)anilino]-4-(1-isopropyl-2-methyl-1H-imidazol-5-yl)-5-chloropyrimidine (Example 34; 276 mg, 1.00 mmol) in DMF (7 ml) was added L-lactic acid (90 mg, 1.50 mmol), and DIPEA (245 µl, 181 mg, 2.1 mmol). A solution of HATU (330 mg, 1.30 mmol) in DMF (3 ml) was added drop wise, then the mixture was stirred at ambient temperature for 20 hours. The solution was concentrated in vacuo then the residue dissolved in EtOAc (20 ml), and washed with aqueous sodium bicarbonate solution (15 ml), then brine (15 ml). The organic extract was dried and concentrated. The residue was purified by chromatography on silica gel with 2N $NH_3$-MeOH:DCM (3:97 to 5:95) to yield the title compound as a white solid (233 mg, 72%). NMR: 1.37 (d, 3H), 1.45 (d, 6H), 2.58 (s, 3H), 3.12-3.17 (m, 4H), 3.56-3.60 (m, 2H), 3.75-3.92 (m, 3H), 4.48-4.54 (m, 1H), 4.96 (quintet, 1H), 6.91 (d, 2H), 6.94 (s, 1H), 7.43 (d, 2H), 7.50 (s, 1H), 8.38 (s, 1H); m/z 484.

Examples 39-47

The following compounds were prepared by the procedure of Example 38 using the appropriate acid and 2-[4-(piperazin-1-yl)anilino]-4-(1-isopropyl-2-methyl-1H-imidazol-5-yl)-5-chloropyrimidine (Example 34).

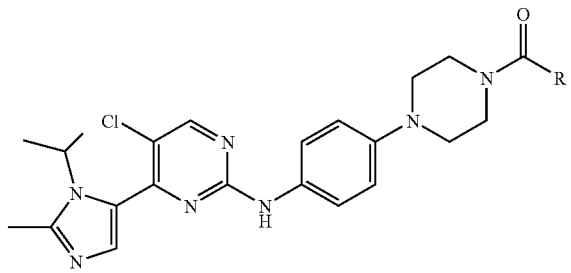

| Ex | R | NMR (300 MHz, $CDCl_3$) | m/z |
| --- | --- | --- | --- |
| 39 | (R)-MeCH(OH)— | 1.37 (d, 3H), 1.45 (d, 6H), 2.58 (s, 3H), 3.12-3.17 (m, 4H), 3.56-3.60 (m, 2H), 3.75-3.92 (m, 3H), 4.48-4.54 (m, 1H), 4.96 (quintet, 1H), 6.91 (d, 2H), 6.94 (s, 1H), 7.43 (d, 2H), 7.50 (s, 1H), 8.38 (s, 1H) | 484 |
| 40 | $MeOCH_2$— | 1.43 (d, 6H), 2.57 (s, 3H), 3.10-3.15 (m, 4H), 3.44 (s, 3H), 3.65-3.69 (m, 2H), 3.76-3.80 (m, 2H), 4.15 (s, 2H), 4.93 (quintet, 1H), 6.91 (d, 2H), 6.94 (s, 1H), 7.41 (d, 2H), 7.50 (s, 1H), 8.37 (s, 1H) | 484 |
| 41 | 1-Hydroxycycloprop-1-yl | (d6-DMSO): 0.74-0.78 (m, 2H), 0.90-0.95 (m, 2H), 1.34 (d, 6H), 2.46 (s, 3H), 3.04-3.08 (m, 4H), 3.68-3.80 (m, 4H), 4.79 (quintet, 1H), 6.33 (s, 1H), 6.91 (d, 2H), 7.21 (s, 1H), 7.45, (d, 2H), 8.50 (s, 1H), 9.48 (s, 1H) | 496 |
| 42 | (R)-MeCH(OMe)— | 1.42-1.46 (m, 911), 2.58 (s, 3H), 3.11-3.16 (m, 4H), 3.37 (s, 3H), 3.78-3.86 (m, 4H), 4.20 (q, 1H), 4.94 (quintet, 1H), 6.91 (d, 2H), 6.93 (s, 1H), 7.42 (d, 2H), 7.51 (s, 1H), 8.38 (s, 1H) | 498 |
| 43 | (S)-MeCH(OMe)— | 1.42-1.46 (m, 9H), 2.58 (s, 3H), 3.11-3.16 (m, 4H), 3.37 (s, 3H), 3.78-3.86 (m, 4H), 4.20 (q, 1H), 4.94 (quintet, 1H), 6.91 (d, 2H), 6.93 (s, 1H), 7.42 (d, 2H), 7.51 (s, 1H), 8.38 (s, 1H) | 498 |
| 44 | (S)-$MeCH_2$CH(OH)— | 1.01 (t, 3H), 1.43 (d, 6H), 1.49-1.58 (m, 1H), 1.69-1.78 (m, 1H), 2.57 (s, 3H), 3.11-3.15 (m, 4H), 3.55-3.59 (m, 2H), 3.70-3.90 (m, 3H), 4.34-4.38 (m, 1H), 4.92 (quintet, 1H), 6.91 (d, 2H), 6.96 (s, 1H), 7.42 (d, 2H), 7.51 (s, 1H), 8.37 (s, 1H) | 498 |
| 45 | MeCH(Me)— | 1.17 (d, 6H), 1.44 (d, 6H), 2.58 (s, 3H), 2.82-2.89 (m, 1H), 3.09-3.15 (m, 4H), 3.66-3.72 (m, 2H), 3.76-3.82 (m, 2H), 4.94 (quintet, 1H), 6.91 (d, 2H), 6.93 (s, 1H), 7.41 (d, 2H), 7.51 (s, 1H), 8.38 (s, 1H) | 482 |
| 46 | Cyclopropyl- | 0.77-0.83 (m, 2H), 1.00-1.05 (m, 2H), 1.44 (d, 6H), 1.74-1.81 (m, 1H), 2.58 (s, 3H), 3.11-3.19 (m, 4H), 3.79-3.87 (m, 4H), 4.94 (quintet, 1H), 6.91 (d, 2H), 6.94 (s, 1H), 7.41 (d, 2H), 7.51 (s, 1H), 8.37 (s, 1H) | 480 |
| 47 | (R)-$MeCH_2$CH(OH)— | 1.01 (t, 3H), 1.43 (d, 6H), 1.49-1.58 (m, 1H), 1.69-1.78 (m, 1H), 2.57 (s, 3H), 3.11-3.15 (m, 4H), 3.55-3.59 (m, 2H), 3.70-3.90 (m, 3H), 4.34-4.38 (m, 1H), 4.92 (quintet, 1H), 6.91 (d, 2H), 6.96 (s, 1H), 7.42 (d, 2H), 7.51 (s, 1H), 8.37 (s, 1H) | 498 |

Examples 48-64

The following compounds were prepared by the procedure of Example 38 using the appropriate acid and 2-[4-(piperazin-1-yl)anilino]-4-(1-isopropyl-2-methyl-1H-imidazol-5-yl)-5-chloropyrimidine (Example 34). The isolated free bases were then dissolved in EtOAc (3 ml) with the addition of a few drops of MeOH to aid dissolution. 1.0M hydrogen chloride in ether solution (1 equivalent) was added, and the resultant hydrochloride salts were triturated with ether then filtered and dried in vacuo.

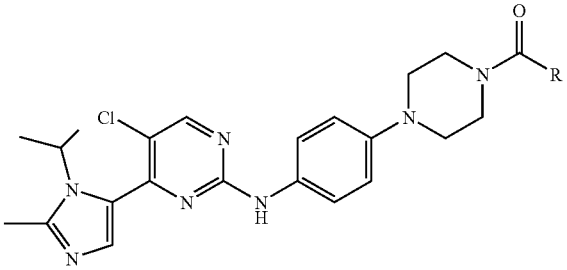

| Ex | R | NMR | m/z |
|---|---|---|---|
| 48 | MeOCH$_2$CH$_2$— | 1.42 (d, 6H), 2.48 (s, 3H), 2.63 (t, 2H), 2.79 (s, 3H), 3.23-3.30 (m, 4H), 3.57 (t, 2H), 3.77-3.82 (m, 4H), 4.80 (quintet, 1H), 7.34-7.38 (m, 2H), 7.62 (d, 2H), 7.99 (s, 1H), 8.76 (s, 1H), 10.08 (brs, 1H) | 498 |
| 49 | 1-Cyanocycloprop-1-yl- | 1.42 (d, 6H), 1.52-1.56 (m, 2H), 1.60-1.64 (m, 2H), 2.78 (s, 3H), 3.27-3.33 (m, 4H), 3.85-3.91 (m, 4H), 4.80 (quintet, 1H), 7.24 (d, 2H), 7.59 (d, 2H), 7.98 (s, 1H), 8.74 (s, 1H), 10.01 (brs, 1H) | 505 |
| 50 | (R)-Tetrahydrofur-2-yl- | 1.42 (d, 6H), 1.79-1.87 (m, 2H), 1.98-2.11 (m, 2H), 2.78 (s, 3H), 3.19-3.27 (m, 4H), 3.70-3.83 (m, 6H), 4.70 (dd, 1H), 4.80 (quintet, 1H), 7.23-7.30 (m, 2H), 7.59 (d, 2H), 7.98 (s, 1H), 8.74 (s, 1H), 10.02 (brs, 1H) | 510 |
| 51 | (S)-Tetrahydrofur-2-yl- | 1.42 (d, 6H), 1.79-1.87 (m, 2H), 1.98-2.11 (m, 2H), 2.78 (s, 3H), 3.19-3.27 (m, 4H), 3.70-3.83 (m, 6H), 4.70 (dd, 1H), 4.80 (quintet, 1H), 7.23-7.30 (m, 2H), 7.59 (d, 2H), 7.98 (s, 1H), 8.74 (s, 1H), 10.02 (brs, 1H) | 510 |
| 52 | MeC(Me)(OH)CH$_2$— | 1.19 (s, 6H), 1.42 (d, 6H), 2.50 (s, 2H), 2.79 (s, 3H), 3.25-3.33 (m, 4H), 3.81-3.89 (m, 4H), 4.80 (quintet, 1H), 7.34-7.40 (m, 2H), 7.63 (d, 2H), 7.99 (s, 1H), 8.76 (s, 1H), 10.08 (brs, 1H) | 512 |
| 53 | HOCH$_2$C(Me)$_2$— | 1.18 (s, 6H), 1.42 (d, 6H), 2.79 (s, 3H), 3.25-3.29 (m, 4H), 3.44 (s, 2H), 3.84-3.90 (m, 4H), 4.80 (quintet, 1H), 7.32-7.40 (m, 2H), 7.62 (d, 2H), 7.99 (s, 1H), 8.76 (s, 1H), 10.07 (brs, 1H) | 512 |
| 54 | (R)-MeCH(Me)CH(OH)— | 0.84 (d, 3H), 0.88 (d, 3H), 1.42 (d, 6H), 1.82-1.90 (m, 1H), 2.79 (s, 3H), 3.27-3.33 (m, 4H), 3.85-3.92 (m, 4H), 4.06 (d, 1H), 4.79 (quintet, 1H), 7.38-7.42 (m, 2H), 7.64 (d, 2H), 7.99 (s, 1H), 8.76 (s, 1H), 10.09 (brs, 1H) | 512 |
| 55 | (S)-MeCH(Me)CH(OH)— | 0.84 (d, 3H), 0.88 (d, 3H), 1.42 (d, 6H), 1.82-1.90 (m, 1H), 2.79 (s, 3H), 3.27-3.33 (m, 4H), 3.85-3.92 (m, 4H), 4.06 (d, 1H), 4.79 (quintet, 1H), 7.3 8-7.42 (m, 2H), 7.64 (d, 2H), 7.99 (s, 1H), 8.76 (s, 1H), 10.09 (brs, 1H) | 512 |
| 56 | HC≡CCH$_2$OCH$_2$— | 1.42 (d, 6H), 2.78 (s, 3H), 3.22-3.30 (m, 4H), 3.49 (t, 1H), 3.67-3.75 (m, 4H), 4.23 (d, 2H), 4.26 (s, 2H), 4.80 (quintet, 1H), 7.26-7.33 (m, 2H), 7.61 (d, 2H), 7.99 (s, 1H), 8.75 (s, 1H), 10.04 (brs, 1H) | 508 |
| 57 | Tetrahydrofur-3-yl- | 1.42 (d, 6H), 2.03 (q, 2H), 2.78 (s, 3H), 3.22-3.30 (m, 4H), 3.36-3.45 (m, 1H), 3.66-3.76 (m, 4H), 3.77-3.84 (m, 4H), 4.80 (quintet, 1H), 7.28-7.36 (m, 2H), 7.61 (d, 2H), 7.99 (s, 1H), 8.75 (s, 1H), 10.05 (brs, 1H) | 510 |
| 58 | (Me)$_2$NCH$_2$CH$_2$— | 1.42 (d, 6H), 2.74-2.78 (m, 9H), 2.93 (t, 2H), 3.21-3.32 (m, 6H), 3.72-3.78 (m, 4H), 4.80 (quintet, 1H), 7.22-7.28 (m, 2H), 7.59 (d, 2H), 7.99 (s, 1H), 8.74 (s, 1H), 10.01 (brs, 1H) | 511 |

-continued

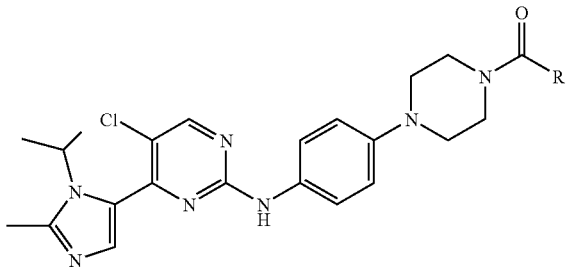

| Ex | R | NMR | m/z |
|---|---|---|---|
| 59 | HOCH$_2$N(Me)CH$_2$— | 1.42 (d, 6H), 2.78 (s, 3H), 2.88-2.95 (7H, m), 3.20-3.31 (m, 4H), 3.42-3.51 (m, 4H), 4.80 (quintet, 1H), 7.05 (d, 2H), 7.52 (d, 2H), 7.98 (s, 1H), 8.71 (s, 1H), 9.89 (brs, 1H) | 511 |
| 60 | (HOCH$_2$)$_2$C— | 1.42 (d, 6H), 2.78 (s, 3H), 3.05-3.11 (m, 1H), 3.22-3.30 (m, 4H), 3.48-3.52 (m, 4H), 3.78-3.90 (m, 4H), 4.80 (quintet, 1H), 7.29-7.35 (m, 2H), 7.61 (d, 2H), 7.99 (s, 1H), 8.75 (s, 1H), 10.04 (brs, 1H) | 514 |
| 61 | Tetrazol-1-yl-CH$_2$— | 1.42 (d, 6H), 2.78 (s, 3H), 3.20-3.28 (m, 2H), 3.32-3.40 (m, 2H), 3.70-3.85 (m, 4H), 4.80 (quintet, 1H), 5.72 (s, 2H), 7.20-7.26 (m, 2H), 7.59 (d, 2H), 7.99 (s, 1H), 8.74 (s, 1H), 9.31 (s, 1H), 10.04 (brs, 1H) | 522 |
| 62 | 1H-Tetrazol-5-yl-CH$_2$— | (MeOD): 1.54 (d, 6H), 2.82 (s, 3H), 3.57-3.63 (m, 2H), 3.75-3.81 (m, 2H), 4.03-4.12 (m, 4H), 4.32 (s, 2H), 4.92 (quintet, 1H), 7.55 (d, 2H), 7.83 (d, 2H), 7.86 (s, 1H), 8.68 (s, 1H) | 522 |
| 63 | 1-Methyl-L-prolyl- | 1.42 (d, 6H), 1.84-1.92 (m, 2H), 2.04-2.14 (m, 1H), 2.52-2.59 (m, 1H), 2.79-2.82 (m, 6H), 3.11-3.22 (m, 4H), 3.59-3.85 (m, 6H), 4.70-4.84 (m, 2H), 7.10 (d, 2H), 7.54 (d, 2H), 7.97 (s, 1H), 8.72 (s, 1H), 9.66 (brs, 1H), 9.93 (s, 1H) | 523 |
| 64 | MeSO$_2$CH$_2$— | 1.42 (d, 6H), 2.79 (s, 3H), 3.11 (s, 3H), 3.22-3.30 (m, 4H), 3.78-3.88 (m, 4H), 4.54 (s, 2H), 4.80 (quintet, 1H), 7.23-7.27 (m, 2H), 7.59 (d, 2H), 7.98 (s, 1H), 8.74 (s, 1H), 10.02 (brs, 1H) | 532 |

Examples 65-86

The following compounds were prepared by the procedure of Example 38 using the appropriate acid and 2-[4-(piperazin-1-yl)anilino]-4-(1-isopropyl-2-methyl-1H-imidazol-5-yl)pyrimidine (Example 20).

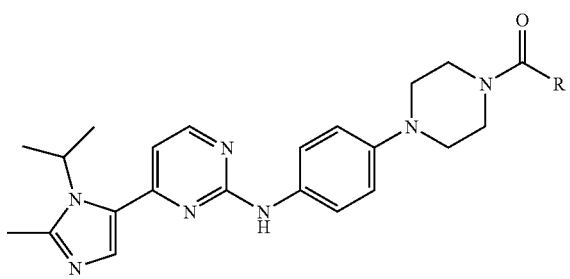

| Ex | R | H NMR (300 MHz) | m/z |
|---|---|---|---|
| 65 | (R)-HOCH(Me) | (CDCL3) 8.31 (d, 1H), 7.46 (d, 2H), 7.38 (s, 1H), 6.92 (d, 2H), 6.86 (d, 2H), 5.66-5.56 (m, 1H), 4.51 (q, 1H), 3.96-3.72 (m, 2H), 3.64-3.54 (m, 2H), 3.21-3.10 (m, 4H), 2.72 (brs, 1H), 2.62 (s, 3H), 1.48 (d, 6H), 1.37 (d, 3H) | 450 |

-continued

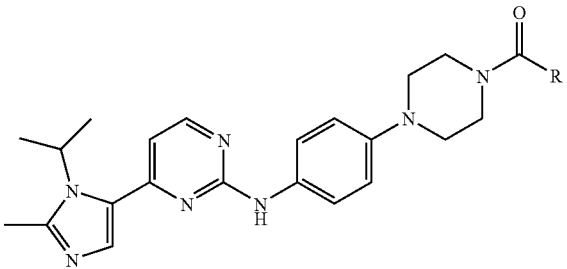

| Ex | R | H NMR (300 MHz) | m/z |
|---|---|---|---|
| 66 | Cyclopropyl | 9.19 (s, 1H), 8.31 (d, 1H), 7.47 (d, 2H), 7.39 (s, 1H), 6.97 (s, 1H), 6.94 (d, 2H), 5.74-5.65 (m, 1H), 3.88-3.71 (m, 2H), 3.69-3.54 (m, 2H), 3.17-2.94 (m, 4H), 2.42 (s, 3H), 2.06-1.95 (m, 1H), 1.40 (d, 6H), 0.79-0.67 (m, 4H) | 447 |
| 67 | MeOCH$_2$— | 9.18 (s, 1H), 8.33 (d, 1H), 7.49 (s, 1H), 7.47 (d, 2H), 6.96 (d, 1H), 6.92 (d, 2H), 5.72-5.63 (m, 1H), 4.13 (s, 2H), 3.62-3.49 (m, 4H), 3.29 (s, 3H), 3.H-3.00 (m, 4H), 2.48 (s, 3H), 1.40 (d, 6H) | 450 |
| 68 | (S)-MeOCH(Me)— | 9.22 (s, 1H), 8.32 (d, 1H), 7.47 (d, 2H), 7.43 (s, 1H), 6.93 (d, 2H), 6.95 (s, 1H), 5.73-5.64 (m, 1H), 4.24 (q, 1H), 3.65 (d, 4H), 3.24 (s, 3H), 3.10 (brs, 4H), 2.47 (s, 3H), 1.40 (d, 6H), 1.23 (d, 3H) | 464 |
| 69 | (S)-HOCH(Me)— | 9.18 (s, 1H), 8.30 (s, 1H), 7.47 (d, 2H), 7.40 (s, 1H), 6.95 (d, 2H), 6.92 (d, 1H), 5.74-5.64 (m, 1H), 4.92 (d, 1H), 4.50-4.41 (m, 1H), 3.72 - 3.50 (m, 4H), 3.13-2.97 (m, 4H), 2.47 (s, 3H), 1.40 (d, 6H), 1.20 (d, 3H) | 450 |
| 70 | (R)-MeOCH(Me)— | 9.20 (s, 1H), 8.31 (d, 1H), 7.47 (d, 2H), 7.41 (s, 1H), 6.93 (d, 2H), 6.95 (s, 1H), 5.74-5.64 (m, 1H), 4.24 (q, 1H), 3.65 (d, 4H), 3.23 (s, 3H), 2.47 (s, 3H), 1.40 (d, 6H), 1.23 (d, 3H) | 464 |
| 71 | i-Pr- | 9.21 (s, 1H), 8.31 (d, 1H), 7.47 (d, 2H), 7.40 (s, 1H), 6.94 (d, 1H), 6.92 (d, 2H), 5.74-5.64 (m, 1H), 3.67 (brs, 4H), 3.04 (d, 4H), 2.94-2.86 (m, 1H), 2.47 (s, 3H), 1.40 (d, 6H), 1.01 (d, 6H) | 448 |
| 72 | MeC(Me)(OH)CH$_2$— | 9.19 (s, 1H), 8.30 (d, 1H), 7.47 (d, 2H), 7.38 (d, 1H), 6.94 (d, 1H), 6.92 (d, 2H), 5.74-5.64 (m, 1H), 4.80 (s, 2H), 3.68-3.59 (m, 4H), 3.29 (s, 1H), 3.10-2.98 (m, 4H), 2.47 (s, 3H), 1.39 (d, 6H), 1.20 (s, 6H) | 478 |
| 73 | 2-(R)-Tetrahydrofur-2-yl | 9.20 (s, 1H), 8.31 (d, 1H), 7.47 (d, 2H), 7.42 (s, 1H), 6.94 (d, 1H), 6.92 (d, 2H), 5.73-5.64 (m, 1H), 4.69 (t, 1H), 3.81-3.70 (m, 2H), 3.69 - 3.55 (m, 4H), 3.10-2.98 (m, 4H), 2.48 (s, 3H), 2.10-1.93 (m, 2H), 1.90-1.76 (m, 2H), 1.40 (d, 6H) | 476 |
| 74 | 2-(S)-Tetrahydrofur-2-yl | 9.20 (s, 1H), 8.32 (d, 1H), 7.47 (d, 2H), 7.42 (s, 1H), 6.94 (d, 1H), 6.92 (d, 2H), 5.73-5.64 (m, 1H), 4.69 (t, 1H), 3.82-3.70 (m, 2H), 3.69 - 3.55 (m, 4H), 3.10-2.99 (m, 4H), 2.48 (s, 3H), 2.09-1.98 (m, 2H), 1.90-1.77 (m, 2H), 1.40 (d, 6H) | 476 |
| 75[1] | 1-Hydroxycycloprop-1-yl | 9.95 (s, 1H), 8.62 (d, 1H), 8.22 (s, 1H), 7.76-7.57 (m, 4H), 7.18 (d, 1H), 5.64-5.55 (m, 1H), 4.24-3.87 (m, 4H), 3.51 (s, 4H), 2.82 (s, 3H), 1.50 (d, 7H), 1.04-0.97 (m, 2H), 0.83-0.77 (m, 2H) | 462 |
| 76[1] | (S)-MeCH$_2$CH(OH)— | 9.83 (s, 1H), 8.60 (d, 1H), 8.20 (s, 1H), 7.65 (d, 2H), 7.50 (s, 2H), 7.15 (d, 1H), 5.64-5.54 (m, 2H), 4.97 (s, 1H), 4.25 (q, 1H), 3.99-3.70 (m, 4H), 3.42-3.25 (m, 4H), 2.81 (s, 3H), 1.72 - 1.58 (m, 2H), 1.49 (d, 6H), 0.89 (t, 3H) | 464 |

-continued

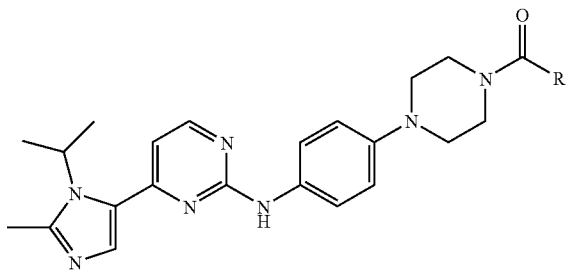

| Ex | R | H NMR (300 MHz) | m/z |
|---|---|---|---|
| 77[1] | (R)-MeCH$_2$CH(OH)— | 9.90 (s, 1H), 8.61 (d, 1H), 8.21 (s, 1H), 7.68 (d, 2H), 7.50 (d, 2H), 7.16 (d, 1H), 5.64-5.55 (m, 1H), 4.25 (q, 1H), 4.02-3.73 (m, 4H), 3.45 - 3.30 (m, 4H), 2.80 (s, 3H), 1.72-1.57 (m, 2H), 1.49 (d, 6H), 0.89 (t, 3H) | 464 |
| 78[1] | 1-Cyanocycloprop-1-yl | 9.74 (s, 1H), 8.58 (d, 1H), 8.20 (s, 1H), 7.58 (d, 2H), 7.26 (d, 2H), 7.12 (d, 1H), 5.64-5.55 (m, 1H), 4.97 (brs, 1H), 4.00-3.76 (m, 4H), 3.36 - 3.25 (m, 4H), 2.80 (s, 3H), 1.65-1.53 (m, 4H), 1.48 (d, 6H) | 471 |
| 79[1] | (R)-MeCH(Me)CH(OH)— | 9.98 (s, 1H), 8.62 (d, 1H), 8.23 (s, 1H), 7.71 (d, 2H), 7.58 (d, 2H), 7.18 (d, 1H), 5.64-5.55 (m, 1H), 5.38 (s, 2H), 4.07 (d, 1H), 4.04-3.78 (m, 4H), 3.48-3.35 (m, 4H), 2.82 (s, 3H), 1.94 - 1.82 (m, 1H), 1.50 (d, 6H), 0.87 (dd, 6H) | 478 |
| 80[1] | (S)-MeCH(Me)CH(OH)— | 9.87 (s, 1H), 8.60 (d, 1H), 8.21 (s, 1H), 7.64 (d, 2H), 7.47-7.34 (m, 2H), 7.15 (d, 1H), 5.64 - 5.54 (m, 1H), 4.20 (brs, 2H), 4.08 (d, 1H), 3.98 -3.70 (m, 4H), 3.38-3.25 (m, 4H), 2.81 (s, 3H), 1.93-1.82 (m, 1H), 1.49 (d, 6H), 0.88 (d, 3H), 0.85 (d, 3H) | 478 |
| 81[1] | 1 MeOCH$_2$CH$_2$— | 10.04 (s, 1H), 8.62 (d, 1H), 8.24 (s, 1H), 7.20 (d, 1H), 5.66-5.56 (m, 1H), 4.80 (brs, ill), 4.02 (s, 4H), 3.58 (t, 2H), 3.52 (s, 4H), 3.26 (s, 3H), 2.84 (s, 3H), 2.65 (t, 2H), 1.50 (d, 6H) | 464 |
| 82[1] | HOCH$_2$C(Me)$_2$— | 9.98 (s, 1H), 8.62 (d, 1H), 8.22 (s, 1H), 7.79-7.60 (m, 4H), 7.19 (d, 1H), 5.64-5.55 (m, 2H), 5.22 (s, 1H), 4.08-3.90 (m, 4H), 3.48 (s, 2H), 3.46-3.38 (m, 4H), 2.82 (s, 3H), 1.50 (d, 6H), 1.20 (s, 6H) | 478 |
| 83[1] | F$_2$CH— | 9.73 (s, 1H), 8.57 (d, 1H), 8.20 (s, 1H), 7.57 (d, 2H), 7.22 (d, 2H), 7.12 (d, 1H), 6.79 (t, 1H), 5.64-5.55 (m, 1H), 4.69 (s, 1H), 3.83-3.71 (m, 4H), 3.34-3.21 (m, 4H), 2.80 (s, 3H), 1.47 (d, 6H) | 456 |
| 84[1] | HC≡CCH$_2$OCH$_2$— | 9.89 (s, 1H), 8.60 (d, 1H), 8.23 (s, 1H), 7.67 (d, 2H), 7.55-7.41 (m, 2H), 7.16 (d, 1H), 5.64 - 5.55 (m, 1H), 4.60 (s, 1H), 4.29 (s, 2H), 4.24 (d, 2H), 3.49 (t, 1H), 2.81 (s, 3H), 1.50 (s, 6H) | 474 |
| 85[1] | HOC(Me)$_2$— | 9.24 (brs, 1H), 8.55 (d, 1H), 7.54 (d, 2H), 7.19 -7.13 (m, 2H), 7.09 (d, 1H), 5.63-5.54 (m, 1H), 4.84 (brs, 1H), 3.97 (s, 4H), 3.24 (s, 4H), 2.81 (s, 3H), 1.52 (d, 6H), 1.41 (s, 6H) | 464 |
| 86[1] | Et— | 9.89 (s, 1H), 8.61 (d, 1H), 8.21 (s, 1H), 7.68 (d, 2H), 7.57 (s, 2H), 7.16 (d, 1H), 5.64-5.54 (m, 1H), 4.86 (s, 1H), 3.90 (s, 4H), 3.44-3.30 (m, 4H), 2.81 (s, 3H), 2.39 (q, 2H), 1.49 (d, 6H), 1.01 (t, 3H) | 471 |

[1]The isolated free base was dissolved in EtOAc (3 ml) with the addition of a few drops of MeOH to aid dissolution. 1.0 M hydrogen chloride in ether solution (1 equivalent) was added, and the resultant hydrochloride salts were triturated with ether then filtered and dried in vacuo.

Example 87
2-{4-[4-(Acetyl)piperazin-1-yl]anilino}-4-(1-isopropyl-2-methyl-1H-imidazol-5-yl)-5-fluoropyrimidine A solution of (2Z)-3-(dimethylamino)-2-fluoro-1-(1-isopropyl-2-methyl-1H-imidazol-5-yl)prop-2-en-1-one (Method 14; 6.0 g, 25 mmol) and N-[4-(4-acetylpiperazin-1-yl)phenyl]guanidine bicarbonate salt (Method 2; 12.12 g, 37.5 mmol) in 2-methoxyethanol (90 ml) was heated under reflux for 18 hrs. The reaction mixture was evaporated under reduced pressure and the title compound was isolated by MPLC on silica gel (3% MeOH/DCM). It was obtained as a crisp foam on evaporation. Yield=8.9 g (81%). NMR: 1.36 (d, 6H), 2.03 (s, 3H), [2.5 (s, 3H) under DMSO signal], 2.98 (m, 2H), 3.08 (m, 2H), 3.57 (m, 4H), 5.44 (septuplet, 1H), 6.90 (d, 2H), 7.34 (d, 1H), 7.42 (d, 2H), 8.44 (d, 1H), 9.24 (s, 1H); m/z 438.

Example 88
2-[4-(Piperazin-1-yl)anilino]-4-(1-isopropyl-2-methyl-1H-imidazol-5-yl)-5-fluoropyrimidine hydrochloride The title compound was prepared from 2-{4-[4-(acetyl) piperazin-1-yl]anilino}-4-(1-isopropyl-2-methyl-1H-imidazol-5-yl)-5-fluoropyrimidine (Example 87) by the procedure of Example 20). The title compound crystallized from the reaction mixture as the HCl salt and was filtered off, washed with isopropanol and ether. Yield=8.01 g (98%). NMR: 1.46 (d, 6H), 2.78 (s, 3H), 3.21 (brs, 4H), 3.32 (m, 4H), 5.24 (septuplet, 1H), 6.96 (d, 2H), 7.47 (d, 1H), 8.05 (d, 2H), 8.70 (d, 1H), 9.42 (brs, 1H), 9.65 (s, 1H); m/z 396.

Examples 89-102

The following compounds were prepared by the procedure of Example 38 using the appropriate acid and 2-[4-(piperazin-1-yl)anilino]-4-(1-isopropyl-2-methyl-1H-imidazol-5-yl)-5-fluoropyrimidine hydrochloride (Example 88).

For Examples 89-96, the isolated free bases were dissolved in EtOAc (3 ml) with the addition of a few drops of MeOH to aid dissolution. 1.0M hydrogen chloride in ether solution (1 equivalent) was added, and the resultant hydrochloride salts were triturated with ether then filtered and dried in vacuo.

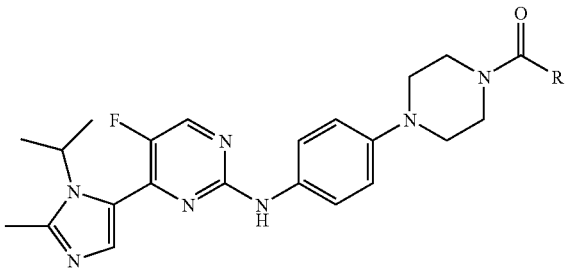

| Ex | R | NMR (CDCl₃) | m/z |
|---|---|---|---|
| 89 | Et— | 1.01 (t, 3H), 1.46 (d, 6H), 2.38 (q, 2H), 2.80 (s, 3H), 3.23-3.33 (m, 4H), 3.73-3.81 (m, 4H), 5.25 (quintet, 1H), 7.32-7.40 (m, 2H), 7.61 (d, 2H), 8.07 (d, 1H), 8.75 (d, 1H). 9.85 (brs, 1H). | 452 |
| 90 | HOCH₂CH₂— | 1.46 (d, 6H), 2.53 (t, 2H), 2.78 (s, 3H), 3.10-3.17 (m, 4H), 3.62-3.68 (m, 4H), 3.70 (t, 2H), 5.28 (quintet, 1H), 6.97 (d, 2H), 7.44 (d, 2H), 7.90 (d, 1H), 8.60 (d, 1H). 9.18 (brs, 1H). | 468 |
| 91 | MeOCH₂CH₂— | 1.45 (d, 6H), 2.62 (t, 2H), 2.79 (s, 3H), 3.14-3.22 (m, 4H), 3.23 (s, 3H), 3.57 (t, 2H), 33.69-3.77 (m, 4H), 5.25 (quintet, 1H), 7.18-2.26 (m, 2H), 7.55 (d, 2H), 8.06 (d, 1H), 8.73 (d, 1H), 9.76 (brs, 1H). | 482 |
| 92 | MeOCH₂— | 1.47 (d, 6H), 2.80 (s, 3H), 3.30 (s, 3H), 3.3 1-3.38 (m, 4H), 3.73-3.82 (m, 4H), 4.15 (s, 2H), 5.24 (quintet, 1H), 7.40-7.47 (m, 2H), 7.63 (d, 2H), 8.08 (d, 1H), 8.76 (d, 1H), 9.90 (brs, 1H). | 468 |
| 93 | i-Pr- | 1.01 (d, 6H), 1.45 (d, 6H), 2.75 (s, 3H), 2.90 (quintet, 1H), 3.10-3.18 (m, 4H), 3.66-3.74 (m, 4H), 5.25 (quintet, 1H), 7.08-7.16 (m, 2H), 7.51 (d, 2H), 8.06 (d, 1H), 8.72 (d, 1H), 9.69 (brs, 1H). | 466 |
| 94 | (R)-MeCH(OH)— | 1.10 (d, 3H), 1.45 (d, 6H), 2.79 (s, 3H), 3.20-3.33 (m, 4H), 3.75-3.87 (m, 4H), 4.47 (q, 1H), 5.25 (quintet, 1H), 7.27-7.33 (m, 2H), 7.57 (d, 2H), 8.07 (d, 1H), 8.73 (d, 1H), 9.81 (brs, 1H). | 468 |
| 95 | MeC(Me)(OH)— | 1.34 (s, 36H), 1.47 (d, 6H), 2.80 (s, 3H), 3.34-3.41 (m, 4H), 3.80-4.00 (m, 4H), 5.24 (quintet, 1H), 7.47-7.55 (m, 2H), 7.65 (d, 2H), 8.08 (d, 1H), 8.77 (d, 1H), 9.92 (brs, 1H). | 482 |

-continued

| | | | | | |
|---|---|---|---|---|---|
| 96 | (S)-MeCH(OH)— | | | 1.21 (d, 3H), 1.48 (d, 6H), 2.78 (s, 3H), 3.15 (b s, 4H), 3.74 (b s, 4H), 4.46 (q, 1H), 5.27 (septuplet, 1H), 7.90 (b s, 2H), 7.50 (b d, 2H), 8.09 (d, 1H), 8.72 (d, 1H), 9.57 (bs, 1H) | | 468 |

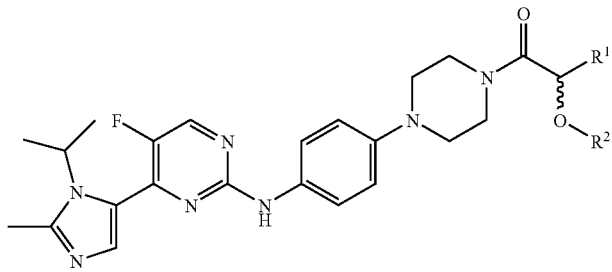

| Ex | R¹ | R² | form | NMR (CDCl₃) | ¹⁹F NMR | m/z |
|---|---|---|---|---|---|---|
| 97 | Et | H | R | 1.02 (t, 3H), 1.47 (d, 6H), 1.55 (m, 1H), 1.75 (m, 1H), 2.59 (s, 3H), 3.15 (m, 4H), 3.58 (brs, 2H), 3.69 (d, 1H), 3.80 (m, 1H), 3.88 (m, 1H), 4.36 (m, 1H), 5.54 (septuplet, 1H), 6.80 (s, 1H), 6.92 (d, 2H), 7.40 (d, 2H), 7.57 (d, 1H), 8.23 (d, 1H) | −147.82 | 482 |
| 98 | Me | Me | R | 1.42 (d, 3H), 1.47 (d, 6H), 2.59 (s, 3H), 3.15 (m, 4H), 3.38 (s, 3H), 3.80 (m, 4H), 4.20 (q, 1H), 5.54 (septuplet, 1H), 6.80 (s, 1H), 6.92 (d, 2H), 7.40 (d, 2H), 7.57 (d, 1H), 8.23 (d, 1H) | −147.93 | 482 |
| 99 | i-Pr | H | R | 0.83 (d, 3H), 1.10 (d, 3H), 1.47 (d, 6H), 1.55 (m, 1H), 1.87 (septuplet, 1H), 2.59 (s, 3H), 3.13 (m, 4H), 3.58 (m, 3H), 3.69 (d, 1H), 3.80 (m, 1H), 3.88 (m, 1H), 4.28 (dd, 1H), 5.54 (septuplet, 1H), 6.80 (s, 1H), 6.91 (d, 2H), 7.40 (d, 2H), 7.57 (d, 1H), 8.23 (d, 1H) | −147.82 | 496 |
| 100 | Et | H | S | 1.02 (t, 3H), 1.47 (d, 6H), 1.55 (m, 1H), 1.75 (m, 1H), 2.59 (s, 3H), 3.15 (m, 4H), 3.58 (brs, 2H), 3.69 (d, 1H), 3.80 (m, 1H), 3.88 (m, 1H), 4.36 (m, 1H), 5.54 (septuplet, 1H), 6.80 (s, 1H), 6.92 (d, 2H), 7.40 (d, 2H), 7.57 (d, 1H), 8.23 (d, 1H) | −147.82 | 482 |
| 101 | Me | Me | S | 1.42 (d, 3H), 1.47 (d, 6H), 2.59 (s, 3H), 3.15 (m, 4H), 3.38 (s, 3H), 3.80 (m, 4H), 4.20 (q, 1H), 5.54 (septuplet, 1H), 6.80 (s, 1H), 6.92 (d, 2H), 7.40 (d, 2H), 7.57 (d, 1H), 8.23 (d, 1H) | −147.93 | 482 |
| 102² | i-Pr | H | S | 0.83 (d, 3H), 1.10 (d, 3H), 1.47 (d, 6H), 1.55 (m, 1H), 1.87 (septuplet, 1H), 2.59 (s, 3H), 3.13 (m, 4H), 3.58 (m, 3H), 3.69 (d, 1H), 3.80 (m, 1H), 3.88 (m, 1H), 4.28 (dd, 1H), 5.54 (septuplet, 1H), 6.80 (s, 1H), 6.91 (d, 2H), 7.40 (d, 2H), 7.57 (d, 1H), 8.23 (d, 1H) | −147.82 | 496 |

[1] Chromatography with 5% MeOH•NH₃ (7 N) in DCM:EtOAc (1:1) solution
[2] Compound required further chromatography eluting with 5% MeOH in EtOAc

Example 103

2-{4-[4-(2-Acetoxyacetylpiperazin-1-yl]anilino}-4-(1-isopropyl-2-methyl-1H-imidazol-5-yl)-5-fluoropyrimidine The title compounds was prepared using the procedure of Example 21 using 2-[4-(piperazin-1-yl)anilino]-4-(1-isopropyl-2-methyl-1H-imidazol-5-yl)-5-fluoropyrimidine hydrochloride (Example 88; 200 mg 0.5 mmol). After work-up, the mixture was purified by chromatography on silica gel using MeOH:DCM (3:97 to 6:94) to give a solid 170 mg. M/z 496.

Example 104

2-{4-[4-(2-Hydroxyacetyl)piperazin-1-yl]anilino}-4-(1-isopropyl-2-methyl-1H-imidazol-5-yl)-5-fluoropyrimidine hydrochloride 2-{4-[4-(2-Acetoxyacetyl)piperazin-1-yl]anilino}-4-(1-isopropyl-2-methyl-1H-imidazol-5-yl)-5-fluoropyrimidine (Example 103) was deprotected by the procedure of Example 22. The reaction mixture was evaporated under reduced pressure. The residue was dissolved in DCM (15 ml), washed with water (10 ml) and brine (10 ml), dried and evaporated. The residue was triturated with ether and re-evaporated to give the title compound as a solid 134 mg. This was converted to the hydrochloride salt from EtOH by the addition of 1M ether/HCl. After evaporation and trituration with ether a solid was obtained. NMR: 1.46 (d, 6H), 2.78 (s, 3H), 3.14 (b s, 4H), 3.58 (b s, 2H), 3.68 (b s, 2H), 4.13 (s, 2H), 5.26 (septuplet, 1H), 7.10 (b s, 2H), 7.50 (d, 2H), 8.08 (d, 1H), 8.72 (d, 1H), 9.68 (b s, 1H); m/z 454.

Example 105

2-{4-[4-(Acetyl)piperazin-1-yl]anilino}-4-(1-cyclobutyl-2-methyl-1H-imidazol-5-yl)-5-fluoropyrimidine The title compound was prepared from (2Z)-1-(1-cyclobutyl-2-methyl-1H-imidazol-5-yl)-3-(dimethylamino)-2-fluoroprop-2-en-1-one (Method 16; 1.406 g) and N-[4-(4-acetylpiperazin-1-yl)phenyl]guanidine bicarbonate salt (Method 2, 2.71 g) by the procedure of Example 18 to yield a white solid (2.21 g, 88%). NMR: 1.61-1.72 (m, 2H), 2.06 (s, 3H), 2.30-2.43 (m, 4H), 2.75 (s, 3H), 3.27-3.39 (m, 4H), 3.77-3.85 (m, 4H), 5.22 (quintet, 1H), 7.42-7.48 (m, 2H), 7.69 (d, 2H), 8.09 (d, 1H), 8.74 (d, 1H), 9.97 (brs, 1H); m/z 450.

Example 106

2-[4-(Piperazin-1-yl)anilino]-4-(1-cyclobutyl-2-methyl-1H-imidazol-5-yl)-5-fluoropyrimidine The title compound was prepared from 2-{4-[4-(acetyl)piperazin-1-yl]anilino}-4-(1-cyclobutyl-2-methyl-1H-imidazol-5-yl)-5-fluoropyrimidine (Example 105; 1.89 g) by the procedure of Example 20 to yield a yellow solid (1.538 g, 90%). NMR (CDCl$_3$): 1.61-1.78 (m, 2H), 2.35-2.45 (m, 4H), 2.59 (s, 3H), 3.03-3.09 (m, 4H), 3.10-3.15 (m, 4H), 5.33 (quintet, 1H), 6.93 (s, 1H), 6.95 (d, 2H), 7.42 (d, 2H), 7.49 (d, 1H), 8.22 (d, 1H); m/z 408.

Examples 107-110

The following compounds were prepared by the procedure of Example 38 using the appropriate acid and 2-[4-(piperazin-1-yl)anilino]-4-(1-cyclobutyl-2-methyl-1H-imidazol-5-yl)-5-fluoropyrimidine (Example 106). The isolated free bases were dissolved in EtOAc (3 ml) with the addition of a few drops of MeOH to aid dissolution. 1.0M hydrogen chloride in ether solution (1 equivalent) was added, and the resultant hydrochloride salts were triturated with ether then filtered and dried in vacuo

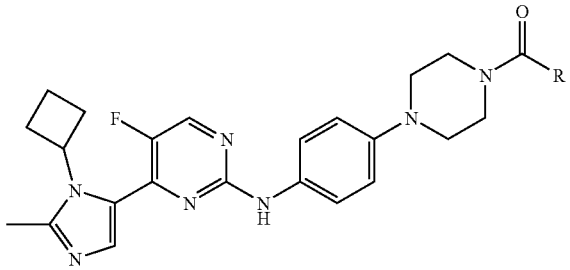

| Ex | R | NMR (300 MHz, CDCl$_3$) | m/z |
|---|---|---|---|
| 107 | HOCH$_2$— | 1.61-1.72 (m, 2H), 2.31-2.44 (m, 4H), 2.75 (s, 3H), 3.28-3.36 (m, 4H), 3.70-3.85 (m, 4H), 4.15 (s, 2H), 5.22 (quintet, 1H), 7.42 (m, 2H, 7.68 (d, 2H), 8.09 (s, 1H), 8.74 (1H, s), 9.95 (brs, 1H). | 466 |
| 108 | (S)-MeCH(OH)— | 1.22 (d, 3H), 1.63-1.72 (m, 2H), 2.30-2.43 (m, 4H), 2.75 (s, 3H), 3.30-3.38 (m, 4H), 3.80-3.96 (m, 4H), 4.46 (q, 1H), 5.22 (quintet, 1H), 7.39-7.47 (m, 2H), 7.68 (d, 2H), 8.08 (d, 1H), 8.74 (d, 1H), 9.95 (brs, 1H). | 480 |
| 109 | (R)-MeCH(OH)— | 1.22 (d, 3H), 1.63-1.72 (m, 2H), 2.30-2.43 (m, 4H), 2.75 (s, 3H), 3.30-3.38 (m, 4H), 3.80-3.96 (m, 4H), 4.46 (q, 1H), 5.22 (quintet, 1H), 7.39-7.47 (m, 2H), 7.68 (d, 2H), 8.08 (d, 1H), 8.74 (d, 1H), 9.95 (brs, 1H). | 480 |
| 110 | MeOCH$_2$— | 1.62-1.72 (m, 2H), 2.30-2.44 (m, 4H), 2.75 (s, 3H), 3.31 (s, 3H), 3.32-3.39 (m, 4H), 3.75-3.85 (m, 4H), 4.16 (s, 2H), 5.22 (quintet, 1H), 7.43-7.50 (m, 2H), 7.70 (d, 2H), 8.09 (d, 1H), 8.75 (d, 1H), 9.99 (brs, 1H). | 480 |

Example 111

2-[4-(Morpholino)anilino]-4-(1-isopropyl-2-methyl-1H-imidazol-5-yl)pyrimidine (2E)-3-(Dimethylamino)-1-(1-isopropyl-2-methyl-1H-imidazol-5-yl)prop-2-en-1-one (Method 24 of WO 03/076436); (10 mg 0.5 mmol) and N-[4-(morpholino)phenyl]guanidine bicarbonate salt (Method 4; 170 mg 0.6 mmol) in dimethylacetamide (4 ml) were heated for 20 minutes at 200° C. in a microwave. The reaction mixture was evaporated under reduced pressure and the residue purified by chromatography on silica gel with MeOH:DCM (4:96 to 8:92) to give the title compound, after trituration with ether, as a solid 90 mg 50%. NMR 1.42 (d, 6H), 2.48 (s, 3H), 3.06 (t, 4H), 3.75 (t, 4H), 5.71 (septuplet, 1H), 6.91 (d, 2H), 6.97 (d, 1H), 7.40 (s, 1H), 7.48 (d, 2H), 8.32 (s, 1H), 9.18 (s, 1H); m/z 379.

Example 112

2-[4-(Morpholino)anilino]-4-(1-ethyl-2-methyl-1H-imidazol-5-yl)-5-fluoropyrimidine hydrochloride (2E)-3-(Dimethylamino)-1-(1-ethyl-2-methyl-1H-imidazol-5-yl)-2-fluoro-prop-2-en-1-one (Method 15; 250 mg 1.11 mmol) and N-[4-(morpholino)phenyl]guanidine bicarbonate salt (Method 4; 405 mg 1.44 mmol) in 2-methoxyethanol (4.5 ml) were heated for 30 minutes at 200° C. in a microwave. The reaction mixture was evaporated under reduced pressure and the residue purified by chromatography on neutral alumina (activityII) with MeOH:DCM:EtOAc (1:79.5:19.5) to give the title compound, after trituration with ether, as a solid 230 mg 54%. This was converted to the hydrochloride salt from MeOH with 1M ether/HCl. Trituration with ether and evaporation gave the title compound as a solid. NMR 1.19 (t, 3H), 2.70 (s, 3H), 3.12 (b s, 4H), 3.60 (b s, exchangeables), 3.79 (t, 4H), 4.59 (q, 2H), 7.05 (b s, 2H), 7.44 (d, 2H), 8.20 (d, 1H), 8.68 (d, 1H), 9.54 (s, 1H); m/z 383.

Example 113

2-[4-(Morpholino)anilino]-4-(1-isopropyl-2-methyl-1H-imidazol-5-yl)-5-fluoropyrimidine (2E)-3-(Dimethylamino)-2-fluoro-1-(1-isopropyl-2-methyl-1H-imidazol-5-yl)prop-2-en-1-one (Method 14; 240 mg 1.0 mmol) and N-[4-(morpholino)phenyl]guanidine bicarbonate salt (Method 4; 367 mg 1.3 mmol) in 2-methoxyethanol (4.5 ml) were heated for 40 minutes at 160° C. then 20 minutes at 180° C. in a microwave. The reaction mixture was evaporated under reduced pressure and the residue purified by chromatography on silica gel with MeOH:DCM:EtOAc (4:48:48 to 10:45:45) to give the title compound as a solid 180 mg 45%. This was converted to the hydrochloride salt from MeOH with 1M ether/HCl. Trituration with ether and evaporation gave the title compound as a solid. NMR (373K): 1.48 (d, 6H), 2.77 (s, 3H), 3.09 (t, 4H), 3.78 (t, 4H), 5.30 (septuplet, 1H), 6.94 (d, 2H), 7.43 (d, 2H), 7.88 (d, 1H), 8.602 (d, 1H); m/z 397.

Example 114

2-[4-(Morpholino)anilino]-4-(1-cyclobutyl-2-methyl-1H-imidazol-5-yl)pyrimidine

The title compound was prepared from (2E)-1-(1-cyclobutyl-2-methyl-1H-imidazol-5-yl)-3-(dimethylamino)prop-2-en-1-one (Method 37 of WO 03/076435; 233 mg) and N-(4-morpholin-4-ylphenyl)guanidine (Method 4, 405 mg) by the procedure of Example 111 to yield a white solid (228 mg, 61%). NMR: 1.59-1.72 (m, 2H), 2.32-2.44 (m, 4H), 2.75 (s, 3H), 3.21-3.28 (m, 4H), 3.84-3.92 (m, 4H), 5.40 (quintet, 1H), 7.09 (d, 1H), 7.24-7.32 (m, 2H), 7.66 (d, 2H), 8.11 (s, 1H), 8.57 (d, 1H), 9.77 (brs, 1H); m/z 391.

Example 115

2-[4-(Morpholino)anilino]-4-(1-cyclobutyl-2-methyl-1H-imidazol-5-yl)-5-fluoropyrimidine The title compound was prepared from (2Z)-1-(1-cyclobutyl-2-methyl-1H-imidazol-5-yl)-3-(dimethylamino)-2-fluoroprop-2-en-1-one (Method 16; 234 mg) and N-(4-morpholin-4-ylphenyl)guanidine (Method 4; 410 mg) by the procedure of Example 111 to yield a white solid (288 mg, 76%). NMR: 1.61-1.72 (m, 2H), 2.29-2.45 (m, 4H), 2.75 (s, 3H), 3.26-3.34 (m, 4H), 3.90-3.97 (m, 4H), 5.22 (quintet, 1H), 7.38-7.45 (m, 2H), 7.68 (d, 2H), 8.08 (d, 1H), 8.73 (d, 1H), 9.95 (brs, 1H); m/z 409.

Example 116

2-{4-[4-(Acetyl)piperazin-1-yl]3-methylanilino}-4-(1-isopropyl-2-methyl-1H-imidazol-5-yl)-5-fluoropyrimidine A solution of (2Z)-3-(dimethylamino)-2-fluoro-1-(1-isopropyl-2-methyl-1H-imidazol-5-yl)prop-2-en-1-one (Method 14, 1.53 g, 6.4 mmol) and N-[4-(4-acetylpiperazin-1-yl)3-methylphenyl]guanidine bicarbonate salt (Method 31, 3.23 g, 9.60 mmol) in 2-methoxyethanol (10 ml) was heated under reflux for 24 hrs. The reaction mixture was evaporated under reduced pressure and the residue purified by chromatography on silica gel with MeOH:DCM:EtOAc (1:49.5:49.5 to 10:45:45) to give a solid which required further purification with MeOH:DCM (1:99 to 10:90). After trituration with ether and evaporation of the solvent, the title compound was obtained as a crisp foam which was dried in vac oven overnight at 50° C. (1.91 g, 66%). NMR (400 MHz) 1.40 (d, 6H), 2.05 (s, 3H), 2.26 (s, 3H), 2.55 (s, 3H, under DMSO signal), 2.77 (dt, 4H), 3.58 (m, 4H), 5.41 (septet, 1H), 6.98 (d, 1H), 7.34 (d, 1H), 7.35 (d, 1H), 7.42 (dd, 1H), 8.49 (d, 1H), 9.28 (s, 1H); $^{19}$F NMR (400 MHz) −149.40 (t, 1F); m/z 452.

Example 117-118

The following compounds were prepared using the procedure of Example 116 from (2Z)-3-(dimethylamino)-2-fluoro-1-(1-isopropyl-2-methyl-1H-imidazol-5-yl)prop-2-en-1-one (Method 14) and the appropriate guanidine.

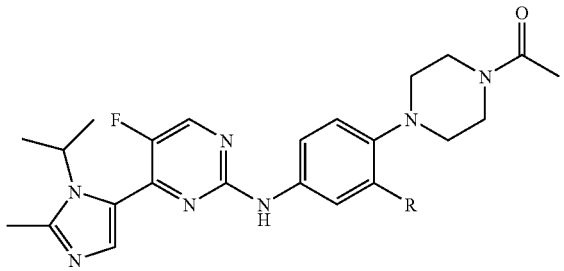

| Ex | R | NMR (400 MHz) | m/z | SM |
|---|---|---|---|---|
| 117[1] | Cl | 1.43 (d, 6H), 2.05 (s, 3H), 2.51 (s, 3H, under DMSO signal), 2.89 (dt, 4H), 3.59 (m, 4H), 5.37 (septet, 1H), 7.12 (d, 1H), 7.36 (d, 1H), 7.53 (dd, 1H), 7.77 (d, 1H), 8.55 (d, 1H), 9.54 (s, 1H); $^{19}$F NMR (400 MHz) -148.33 (t, 1F) | 472-474 | Method 32 |
| 118[2] | F | 1.44 (d, 6H), 2.04 (s, 3H), 2.57 (s, 3H, under DMSO signal), 2.92 (dt, 4H), 3.58 (m, 4H), 5.42 (septet, 1H), 7.00 (t, 1H), 7.30 (dd, 1H), 7.36 (d, 1H), 7.58 (dd, 1H), 8.55 (d, 1H), 9.55 (s, 1H); $^{19}$F NMR (400 MHz) -148.47 (t, 1F) | 456 | Method 33 |

[1]Chromatography with MeOH:DCM:EtOAc(1:49.5:49.5 to 10:45:45). (469.8 mg, 69%).
[2]Chromatography with MeOH:DCM:EtOAc (1:49.5:49.5 to 10:45:45). (2.72 g, 72%).

Example 119

2-{4-[4-(Acetyl)piperazin-1-yl]3-methylanilino}-4-(1-isopropyl-2-methyl-1H-imidazol-5-yl)pyrimidine The title compound was prepared from (2E)-3-(dimethylamino)-1-(1-isopropyl-2-methyl-1H-imidazol-5-yl)prop-2-en-1-one (Method 24 of WO 03/076436; 331.8 g, 1.5 mmol) and N-[4-(4-acetylpiperazin-1-yl)3-methylphenyl]guanidine bicarbonate salt (Method 31; 758.3 mg, 2.25 mmol) by the procedure of Example 116. The reaction mixture was evaporated under reduced pressure and the residue purified by chromatography on silica gel with MeOH:DCM:EtOAc (1:49.5:49.5 to 10:45:45) to give a solid (419.4 mg, 65%) NMR: 1.41 (d, 6H), 2.05 (s, 3H), 2.27 (s, 3H), 2.48 (s, 3H), 2.77 (dt, 4H), 3.58 (m, 4H), 5.66 (septet, 1H), 6.97 (d, 1H), 6.99 (d, 1H), 7.37 (d, 1H), 7.41 (s, 1H), 7.47 (dd, 1H), 8.35 (d, 1H), 9.20 (s, 1H); m/z 434.

Examples 120-121

The following compounds were prepared using the procedure of Example 119 from (2E)-3-(dimethylamino)-1-(1-isopropyl-2-methyl-1H-imidazol-5-yl)prop-2-en-1-one (Method 24 of WO 03/076436) and the appropriate guanidine.

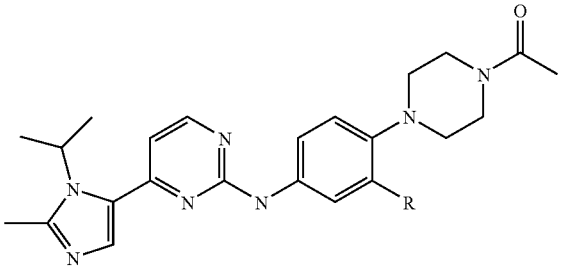

| Ex | R | NMR (400 MHz) | m/z | SM |
|---|---|---|---|---|
| 120[1] | Cl | 1.45 (d, 6H), 2.05 (s, 3H), 2.50 (s, 3H+DMSO), 2.90 (dt, 4H), 3.59 (m, 4H), 5.62 (septet, 1H), 7.05 (d, 1H), 7.12 (d, 1H), 7.43 (s, 1H), 7.57 (dd, 1H), 7.81 (d, 1H), 8.40 (d, 1H), 9.45 (s, 1H) | 454-456 | Method 32 |
| 121[2] | F | 1.45 (d, 6H), 2.04 (s, 3H), 2.57 (s, 3H+DMSO), 2.93 (dt, 4H), 3.59 (m, 4H), 5.68 (septet, 1H), 7.00 (t, 2H), 7.05 (d, 2H), 7.33 (dd, 1H), 7.42 (s, 1H), 7.64 (dd, 1H), 8.39 (d, 1H), 9.46 (s, 1H) | 438 | Method 33 |

[1]This compound required further chromatography on Basic prep HPLC with acetonitrile:1% NH$_3$/H$_2$O (25:75 to 70:30). (475 mg, 52%).
[2](413.5 mg, 63%).

Example 122

2-[4-(Piperazin-1-yl)3-methylanilino]-4-(1-isopropyl-2-methyl-1H-imidazol-5-yl)-5-fluoropyrimidine 2-{4-[4-(Acetyl)piperazin-1-yl]3-methylanilino}-4-(1-isopropyl-2-methyl-1H-imidazol-5-yl)-5-fluoropyrimidine (Example 116; 1.89 g, 4.19 mmol) was stirred and heated in isopropanol (20 ml), $H_2O$ (5 ml) and 33% hydrochloric acid (4 ml) at 90° C. for 10 hours. The solvent was evaporated under reduced pressure to give a residue which was partitioned between water and DCM, basified with sat. sodium hydrogen carbonate and the aqueous layer was extracted with DCM twice. The organics were combined, washed with brine, dried and evaporation of solvent to give the title compound as a crisp foam which was dried in vac oven overnight at 50° C. (1.53 g, 89%) NMR (400 MHz) 1.39 (d, 6H), 2.23 (s, 3H), 2.51 (s, 3H, under DMSO signal), 2.72 (m, 4H), 2.85 (m, 4H), 3.29 (s, 1H under $H_2O$ signal), 5.42 (septet, 1H), 6.95 (d, 1H), 7.30 (d, 1H), 7.35 (d, 1H), 7.40 (dd, 1H), 8.48 (d, 1H), 9.24 (s, 1H); $^{19}$F NMR (400 MHz) −149.59 (t, 1F); m/z 410.

Example 123

2-[4-(Piperazin-1-yl)3-fluoroanilino]-4-(1-isopropyl-2-methyl-1H-imidazol-5-yl)-5-fluoropyrimidine The compound was prepared from 2-{4-[4-(acetyl)piperazin-1-yl]3-fluoroanilino}-4-(1-isopropyl-2-methyl-1H-imidazol-5-yl)-5-fluoropyrimidine (Example 118, 455 mg, 1 mmol) by the procedure of Example 122. The title compound was obtained as a crisp foam which was dried in vac oven overnight at 50° C. (337.8 mg, 82%). NMR (400 MHz) 1.41 (d, 6H), 2.23 (s, 3H), 2.50 (s, 3H, under DMSO signal), 2.90 (s, 8H), 3.29 (s, 1H under $H_2O$ signal), 5.43 (septet, 1H), 6.96 (t, 1H), 7.29 (dd, 1H), 7.36 (d, 1H), 7.53 (dd, 1H), 8.53 (d, 1H), 9.50 (s, 1H); $^{19}$F NMR (400 MHz) −148.60 (t, 1F); m/z 414.

Example 124

2-{4-[4-((2S)-2-Hydroxypropionyl)piperazin-1-yl]3-methylanilino}-4-(1-isopropyl-2-methyl-1H-imidazol-5-yl)-5-fluoropyrimidine A solution of 2-[4-(piperazin-1-yl)3-methylanilino]-4-(1-isopropyl-2-methyl-1H-imidazol-5-yl)-5-fluoropyrimidine (Example 122; 490.8 mg, 1.20 mmol), L-lactic acid (129.7 mg, 1.44 mmol), HOBt.$H_2O$ (220.5 mg, 1.44 mmol) and DIPEA (0.24 ml, 1.44 mmol) in DMF (5 ml) was cooled to 0° C., followed by addition of EDAC (230.05 mg, 1.44 mmol) in portions. The mixture was then stirred at ambient temperature for 3.5 hours. The solution was concentrated in vacuo, then the residue was partitioned between DCM and water+sat. sodium hydrogen carbonate. The organic extract was washed with water (3 times), brine, dried and concentrated. To a solution of crude product in MeOH (5 ml) was added 1 pellet of KOH and the mixture was stirred at ambient temperature for 20 min. The residue obtained on evaporation was purified by chromatography on silica gel with MeOH:DCM (1:99 to 5:95) to yield the title compound, after trituration with ether, as a solid which was dried in vac oven overnight at 50° C. (415 mg, 72%). NMR: (500 MHz at 373K) 1.27 (d, 3H), 1.40 (d, 6H), 2.28 (s, 3H), 2.48 (s, 3H, under DMSO signal), 2.82 (m, 4H), 3.65 (m, 4H), 4.47 (m, 2H), 5.38 (septet, 1H), 7.00 (d, 1H), 7.35 (m, 2H), 7.40 (dd, 1H), 8.40 (d, 1H), 8.80 (s, 1H); $^{19}$F NMR (400 MHz) −149.33 (t, 1F); m/z 482.

Examples 125-128

The following compounds were prepared by the procedure of Example 124 using the appropriate acid and pyrimidine.

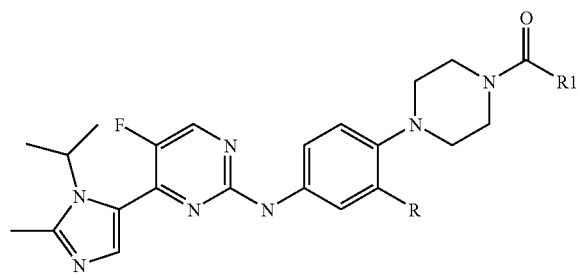

| Ex | R | R1 | NMR (500 MHz) at 373 K | m/z | SM |
|---|---|---|---|---|---|
| 125[1] | Me | $CH_2OH$ | 1.40 (d, 6H), 2.27 (s, 3H), 2.50 (s, 3H, under DMSO signal), 2.80 (m, 4H), 3.57 (m, 4H), 4.13 (d, 2H), 4.20 (t, 1H), 5.37 (septet, 1H), 6.98 (d, 1H), 7.31 (m, 2H), 7.38 (dd, 1H), 8.40 (d, 1H), 8.80 (s, 1H); 19F NMR (400 MHz) −149.31 (t, iF) | 468 | Example 122 |
| 126[2] | F | $CH_2OH$ | 1.44 (d, 6H), 2.59 (s, 3H under DMSO signal), 2.94 (brs, 4H), 3.57 (brd, 4H), 4.13 (brd, 2H), 4.59 (br t, 1H), 5.43 (septet, 1H), 7.00 (t, 1H), 7.30 (dd, 1H), 7.36 (d, 1H), 7.58 (dd, 1H), 8.55 (d, 1H), 9.55 (s, 1H); $^{19}$F NMR −148.46 (t, 1F) | 472 | Example 123 |
| 127[3] | F | (S)-MeCH(OH)— | 1.25 (d, 3H), 1.44 (d, 6H), 2.50 (s, 3H, under DMSO signal), 3.00 (m, 4H), 3.66 (m, 4H), 4.46 (m, 2H), 5.38 (septet, 1H), 6.99 (t, 1H), 7.28 (dd, 1H), 7.33 (d, 1H), 7.49 (dd, 1H), 8.44 (d, 1H), 9.09 (s, 1H); $^{19}$F NMR (500 MHz) −148.40 (t, 1F), −122.6 (s, 1F) | 486 | Example 123 |

-continued

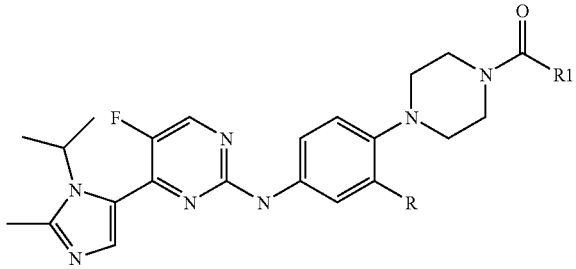

| Ex | R | R1 | NMR (500 MHz) at 373 K | m/z | SM |
|---|---|---|---|---|---|
| 128[4] | F | CH$_2$OMe | 1.43 (d, 6H), 2.50 (s, 3H, under DMSO signal), 3.00 (m, 4H), 3.33 (s, 3H), 3.60 (m, 4H), 4.10 (s, 2H), 5.40 (septet, 1H), 7.00 (t, 1H), 7.30 (dd, 1H), 7.33 (d, 1H), 7.50 (dd, 1H), 8.43 (d, 1H), 9.09 (s, 1H); $^{19}$F NMR (500 MHz) -148.40 (t, 1F), -122.7 (s, 1F) | 486 | Example 123 |

[1] Extra acid (9 mg) and EDAC (23 mg) added and Reaction time = 4.5 h, (365 mg, 65%)
[2] Extra acid (10 mg) and EDAC (20 mg) added and Reaction time = 5.5 h, NMR (400 MHz, RT). Chromatography with MeOH:DCM:(1:99 to 6:94), (334.5 mg, 71%)
[3] Extra acid (10 mg) and EDAC (19 mg) added and Reaction time = 6 h, (378 mg, 78%)
[4] No need to treat the crude product with KOH in MeOH, (310 mg, 64%)

Example 129

2-{4-[(3R,5S)-4-Acetyl-3,5-dimethylpiperazin-1-yl]anilino}-4-(1-isopropyl-2-methyl-1H-imidazol-5-yl)-5-fluoropyrimidine The title compound was prepared from (2Z)-3-(dimethylamino)-2-fluoro-1-(1-isopropyl-2-methyl-1H-imidazol-5-yl)prop-2-en-1-one (Method 14, 331 mg, 1.38 mmol) and N-[4-((3R,5S)-4-acetyl-3,5-dimethylpiperazin-1-yl)phenyl]guanidine (Method 34; 737.1 mg, 2.10 mmol) by the procedure of Example 116. The reaction mixture was evaporated under reduced pressure and the residue purified by chromatography on silica gel with MeOH:DCM:EtOAc (1:49.5:49.5 to 10:45:45) to give a solid which was dried in vac oven overnight at 50° C. (485 mg, 76%) NMR: (400 MHz) 1.30 (s, 6H), 1.41 (d, 6H), 2.05 (s, 3H), 2.50 (s, 3H under DMSO signal), 2.73 (m, 2H), 3.40 (d, 2H), 4.30 (brs, 2H), 5.45 (septet, 1H), 6.95 (d, 2H), 7.35 (d, 1H), 7.45 (d, 2H), 8.49 (d, 1H), 9.25 (s, 1H); $^{19}$F NMR (400 MHz) -149.80 (t, 1F); m/z 466.

Example 130

2-{4-[(2S5R)-4-Acetyl-2,5-dimethylpiperazin-1-yl]anilino}-4-(1-isopropyl-2-methyl-1H-imidazol-5-yl)-5-fluoropyrimidine The title compound was prepared from (2Z)-3-(dimethylamino)-2-fluoro-1-(1-isopropyl-2-methyl-1H-imidazol-5-yl)prop-2-en-1-one (Method 14; 335 mg, 1.40 mmol) and N-[4-((2S,5R)-4-acetyl-2,5-dimethylpiperazin-1-yl)phenyl]guanidine (Method 35; 737.1 mg, 2.10 mmol) by the procedure of Example 116. The reaction mixture was evaporated under reduced pressure and the residue purified by chromatography on silica gel with MeOH:DCM:EtOAc (1:49.5:49.5 to 6:47:47) to give a solid which required further purification with MeOH:DCM (1:99 to 6:94). After trituration with ether and evaporation of the solvent, the title compound was obtained as a solid which was dried in vac oven overnight at 50° C. (330 mg, 51%). NMR: (500 MHz) 0.95 (d, 3H), 1.33 (d, 3H), 1.40 (d, 6H), 2.03 (s, 3H), 2.50 (s, 3H+DMSO), 3.17 (m, 2H), 3.43 (brs, 1H), 3.83 (brs, 1H), 4.00 (m, 1H), 4.47 (brs, 1H), 5.40 (septet, 1H), 6.83 (d, 2H), 7.32 (d, 1H), 7.37 (d, 2H), 8.35 (d, 1H), 8.7 (s, 1H); $^{19}$F NMR (500 MHz MHz) -149.95 (t, 1F); m/z 466.

Example 131

2-(3-Chloro-4-piperazin-1-yl)anilino-4-(1-isopropyl-2-methyl-1H-imidazol-5-yl)pyrimidine hydrochloride 2-[3-Chloro-4-(4-acetylpiperazin-1-yl)anilino]-4-(1-isopropyl-2-methyl-1H-imidazol-5-yl)pyrimidine (Example 120; 4.1 g, 9.1 mmol) was stirred and heated in isopropanol (41 ml) and 33% hydrochloric acid (4.1 ml) at 85° C. for 25 hours. The reaction was evaporated under reduced pressure and then diluted with water (200 ml), washed with DCM (200 ml), basified with aqueous saturated sodium bicarbonate solution and extracted with chloroform (2×400 ml). The solution was dried and evaporated under reduced pressure to give the amine, which was converted to the hydrochloride salt by dissolving in MeOH:DCM (60 ml, 1:1) and treating with a 1.0 molar solution of ethereal-HCl (9.1 ml). The solid was triturated with ether (40 ml) and filtered to give the title compound (3.2 g, 77%). NMR: 1.42 (d, 6H), 2.61 (s, 3H), 3.16 (m, 4H), 3.40 (m, 4H), 5.58 (septet, 1H), 7.10 (d, 1H), 7.14 (d, 1H), 7.48 (dd, 1H), 7.81 (s, 2H), 8.49 (d, 1H), 9.64 (s, 1H); m/z 412.

Example 132

2-[3-Chloro-4-(hydroxyacetyl)piperazin-1-yl]anilino-4-(1-isopropyl-2-methyl-1H-imidazol-5-yl)pyrimidine To a solution of 2-(3-chloro-4-piperazin-1-yl)anilino-4-(1-isopropyl-2-methyl-1H-imidazol-5-yl)pyrimidine hydrochloride (Example 131; 0.44 g, 1.0 mmol) in DCM:DMF (14 ml, 6:1) at 0° C. was added glycolic acid (90 mg, 1.2 mmol), HOBt.H₂O (0.16 g, 1.2 mmol) and DIPEA (1.4 ml, 8.0 mmol). EDAC (0.23 g, 1.2 mmol) was added at 0° C., then the mixture was stirred at ambient temperature for 43 hours. The solution was diluted with DCM (40 ml), then washed with water (3×50 ml), 1.0 molar solution of KOH (50 ml), brine (50 ml) and water (50 ml). The organic extract was dried and concentrated. The residue was purified by chromatography on silica gel with MeOH:DCM (2.5:97.5) to yield the title compound as a pale yellow solid (0.13 g, 28%). NMR: 1.19 (t, 1H), 1.48 (d, 6H), 2.58 (s, 3H), 3.01 (m, 4H), 3.44 (m, 2H), 3.83 (m, 2H), 4.21 (s, 2H), 5.57 (septet, 1H), 6.90 (d, 1H), 6.95 (d, 1H), 7.37 (m, 3H), 7.74 (s, 1H), 8.34 (d, 1H); m/z 470.

Example 133

2-(3-Chloro-4-piperazin-1-yl)anilino-4-(1-isopropyl-2-methyl-1H-imidazol-5-yl)-5-fluoropyrimidine hydrochloride The title compound was prepared from 2-[3-chloro-4-(4-acetylpiperazin-1-yl)anilino]-4-(1-isopropyl-2-methyl-1H-imidazol-5-yl)-5-fluoropyrimidine (Example 117; 4.1 g, 9.1 mmol) by the method of Example 131, and isolated as a brown solid (1.5 g, 94%). NMR: 1.40 (d, 6H), 3.09 (m, 4H), 3.15 (s, 3H), 3.18 (m, 4H), 3.29 (m, 1H), 5.37 (septet, 1H), 7.14 (d, 1H), 7.36 (d, 1H), 7.54 (dd, 1H), 7.78 (d, 1H), 8.54 (d, 1H), 9.58 (s, 1H); m/z 430.

Example 134

2-[3-Chloro-4-(4-hydroxyacetylpiperazin-1-yl)anilino]-4-(1-isopropyl-2-methyl-1H-imidazol-5-yl)-5-fluoropyrimidine The title compound was prepared from 2-(3-chloro-4-piperazin-1-yl)anilino-4-(1-isopropyl-2-methyl-1H-imidazol-5-yl)-5-fluoropyrimidine hydrochloride (Example 133; 0.40 g, 0.86 mmol) by the method of Example 132, and purified by chromatography on silica gel with MeOH:DCM (5:95) to yield a yellow solid (0.25 g, 60%). NMR: 1.47 (d, 6H), 2.61 (s, 3H), 3.01 (m, 4H), 3.44 (m, 2H), 3.84 (m, 2H), 4.22 (s, 2H), 5.55 (septet, 1H), 6.96 (d, 1H), 7.22 (s, 1H), 7.36 (dd, 1H), 7.57 (d, 1H), 7.65 (d, 1H), 8.26 (d, 1H); m/z 488.

Example 135

2-(3-Chloro-4-{4-[(2S)-1-oxopropan-2-ol]piperazin-1-yl}aniline)-4-(1-isopropyl-2-methyl-1H-imidazol-5-yl)-5-fluoropyrimidine The title compound was prepared from 2-(3-chloro-4-piperazin-1-yl)anilino-4-(1-isopropyl-2-methyl-1H-imidazol-5-yl)-5-fluoropyrimidine hydrochloride (Example 133; 0.40 g, 0.86 mmol) by the method of Example 38. The reaction mixture was evaporated under reduced pressure. The residue was diluted with water (60 ml) and extracted with DCM (3×50 ml). The combined organic phases were washed with water (100 ml), then dried and concentrated. The residue was purified by chromatography on silica gel with MeOH:DCM (5:95) to yield the title compound as a yellow solid (0.35 g, 88%). NMR: 1.39 (d, 3H), 1.46 (d, 6H), 2.60 (s, 3H), 2.80 (s, 1H), 3.01 (m, 4H), 3.60 (m, 2H), 3.77 (m, 1H), 3.79 (m, 1H), 4.52 (q, 1H), 5.51 (septet, 1H), 6.96 (d, 1H), 7.37 (dd, 1H), 7.58 (d, 1H), 7.59 (s, 1H), 7.68 (d, 1H), 8.27 (d, 1H); m/z 502.

Example 136

2-[3-Chloro-4-(4-methoxyacetyl)piperazin-1-yl]anilino-4-(1-isopropyl-2-methyl-1H-imidazol-5-yl)-5-fluoropyrimidine The title compound was prepared from 2-(3-chloro-4-piperazin-1-yl)anilino-4-(1-isopropyl-2-methyl-1H-imidazol-5-yl)-5-fluoropyrimidine hydrochloride (Example 133; 0.40 g, 0.86 mmol) by the method of Example 38. The reaction mixture was evaporated under reduced pressure. The residue was diluted with water (100 ml) and extracted with chloroform (3×100 ml). The combined organic phases were concentrated under reduced pressure, then diluted with EtOAc (100 ml) and washed with water (150 ml), then dried and concentrated. The residue was triturated with ether and the solid was purified by chromatography on silica gel with MeOH:DCM (5:95) to yield the title compound as a yellow solid (0.27 g, 62%). NMR: 1.40 (d, 6H), 2.70 (s, 3H), 2.81 (m, 4H), 3.22 (s, 3H), 3.46 (m, 4H), 4.03 (s, 2H), 5.17 (septet, 1H), 7.03 (d, 1H), 7.24 (dd, 1H), 7.72 (d, 1H), 7.95 (s, 1H), 8.69 (s, 1H), 9.78 (s, 1H); m/z 502.

Example 137

1-(4-{[5-fluoro-4-(1-isopropyl-2-methyl-1H-imidazol-5-yl)pyrimidin-2-yl]amino}phenyl)azetidin-3-ol (2Z)-3-(Dimethylamino)-2-fluoro-1-(1-isopropyl-2-methyl-1H-imidazol-5-yl)prop-2-en-1-one (Method 14, 1.54 g, 6.46 mM) and N-[4-(3-hydroxyazetidin-1-yl)phenyl]guanidine bicarbonate salt (Method 39; 2.3 g, 9.7 mM) were stirred and heated in 2-methoxyethanol (17 ml) under nitrogen at 130° C. for 24 hours. The solvent was removed in vacuo and the residue was partitioned between DCM and water. The organic layer was washed with water, dilute sodium bicarbonate, water, saturated sodium chloride and then dried with anhydrous sodium sulphate filtered and evaporated. The crude product was purified by silica chromatography eluting with MeOH:DCM (5:95). The product off the column was triturated with ether, filtered washed with the same solvent and dried to give the title compound as a brown solid (886 mg, 18.3%). NMR 1.35 (d, 6H), 2.5 (s, 3H+H₂O peak) 3.4 (t, 2H), 4.0 (t, 2H), 4.5 (q, 1H), 5.42 (m, 1H), 5.53 (d, 1H), 6.37 (d, 2H), 7.28 (m, 3H), 8.4 (d, 1H), 9.07 (s, 1H); m/z 383.

Example 138

1-(4-{[5-Fluoro-4-(1-isopropyl-2-methyl-1H-imidazol-5-yl)pyrimidin-2-yl]amino}phenyl)azetidin-3-yl methanesulfonate To an ice cooled solution of 1-(4-{[5-fluoro-4-(1-isopropyl-2-methyl-1H-imidazol-5-yl)pyrimidin-2-yl]amino}phenyl)azetidin-3-ol (Example 137; 0.728 g, 1.905 mM) and triethylamine (153 µl, 2.09 mM) in dry DCM (22 ml), mesyl chloride (162 µl, 2.09 mM) was added. The reaction was stirred at 0° C. for 30 minutes and at room temperature for 20 hours. The reaction mixture was diluted with more DCM and extracted in turn with water (twice), saturated sodium chloride, dried with anhydrous sodium sulphate, filtered and evaporated to give the title compound as a brown foam (717 mg, 82%). NMR 1.37 (d, 6H), 2.48 (s, 3H+DMSO), 3.25 (s, 3H), 3.82 (m, 2H), 4.2 (m, 2H), 5.4 (m, 2H), 6.45 (d, 2H), 7.35 (m, 3H), 8.42 (d, 1H), 9.13 (s, 1H); m/z 461.

Example 139

N-[4-(3-Azidoazetidin-1-yl)phenyl]-5-fluoro-4-(1-isopropyl-2-methyl-1H-imidazol-5-yl)pyrimidin-2-amine To a solution of 1-(4-{[5-fluoro-4-(1-isopropyl-2-methyl-1H-imidazol-5-yl)pyrimidin-2-yl]amino}phenyl)azetidin-3-yl methanesulfonate (Example 138; 876 mg, 1.90 mM) in dry DMF (7.3 ml), sodium azide (619 mg, 9.5 mM) was added. The reaction was stirred and heated at 80° C. under nitrogen for 18 hours. The reaction mixture was diluted with EtOAc and the solution extracted with water (twice), saturated sodium chloride and then dried with anhydrous sodium sulphate filtered and evaporated. The crude product was purified by silica chromatography eluting with MeOH:DCM (2:98) to give the title compound as a brown foam (389 mg, 50%). NMR 1.4 (d, 6H), 2.53 (s, 3H+DMSO), 3.65 (m, 2H), 4.1 (m, 2H), 4.44 (m, 1H), 5.4 (m, 1H), 6.44 (d, 2H), 7.33 (m, 3H), 8.35 (d, 1H); m/z 408.

Example 140

N-[4-(3-Aminoazetidin-1-yl)phenyl]-5-fluoro-4-(1-isopropyl-2-methyl-1H-imidazol-5-yl)pyrimidin-2-amine To a solution N-[4-(3-azidoazetidin-1-yl)phenyl]-5-fluoro-4-(1-isopropyl-2-methyl-1H-imidazol-5-yl)pyrimidin-2-amine (Example 139; 382 mg, 938 mM) in THF (10 ml), triphenylphosphine (260 mg, 0.984 mM) was added. The reaction was stirred at room temperature under nitrogen for 24 hours. Water (2.0 ml) was then added and the mixture stirred and heated at 65° C. for 3 hours. Hydrochloric acid (1M, 1.5 ml) was added and the THF removed in vacuo. More water was then added and the solution extracted with EtOAc. Sodium hydroxide (1M, 1.5 ml) was added to the water layer and the solution was extracted with EtOAc. The organic layers were combined, dried with anhydrous sodium sulphate, filtered and evaporated to give the title compound as a yellow foam (324 mg, 91%). NMR (DMSO-$d_6$+$d_4$-acetic acid) 1.38 (d, 6H), 2.5 (s, 3H), 3.73 (m, 2H), 4.05 (m, 3H), 5.43 (m, 1H), 6.45 (d, 2H), 7.33 (s, 1H), 7.4 (d, 2H), 8.4 (d, 1H); m/z 382.

Example 141

N-[1-(4-{[5-Fluoro-4-(1-isopropyl-2-methyl-1H-imidazol-5-yl)pyrimidin-2-yl]amino}phenol)azetidin-3-yl]-2-hydroxyacetamide To a mixture of N-[4-(3-aminoazetidin-1-yl)phenyl]-5-fluoro-4-(1-isopropyl-2-methyl-1H-imidazol-5-yl)pyrimidin-2-amine (Example 140; 107 mg, 0.28 mM) and glycolic acid (26 mg, 0.337 mM) and HOBt hydrate (46 mg, 0.337 mM) in dry DCM (4.0 ml), diisopropylamine (56 µl, 0.337 mM) and EDAC (65 mg, 0.337 mM) were added. The reaction was stirred at room temperature under nitrogen for 72 hours. The DCM was removed in vacuo and the residue dissolved in EtOAc and water. The layers were partitioned and separated. The organic layer was washed in turn with water, dilute sodium bicarbonate (twice), water, saturated sodium chloride and then dried with anhydrous sodium sulphate, filtered and evaporated. The residue was dissolved in MeOH (2.0 ml) and 1.0 molar sodium hydroxide (0.25 ml) added. The solution was stirred at room temperature for 1 hour. The reaction mixture was diluted with EtOAc and water and the layers partitioned and separated. The organic layer was washed with water, saturated sodium chloride, dried with anhydrous sodium sulphate, filtered and evaporated. The crude product was triturated with ether, filtered, washed with ether and dried to give the title compound as a yellow solid (79 mg, 64%). NMR 1.38 (s, 6H), 2.5 (s, 3H+DMSO), 3.64 (t, 2H), 3.8 (d, 2H), 4.03 (t, 2H), 4.63 (m, 1H), 5.37 (t, 1H), 5.45 (m, 1H), 6.4 (d, 2H), 7.33 (m, 3H), 8.28 (d, 1H), 8.4 (d, 1H), 9.08 (s, 1H); m/z 440.

Example 142

N-[1-(4-{[5-Fluoro-4-(1-isopropyl-2-methyl-1H-imidazol-5-yl)pyrimidin-2-yl]amino}phenyl)azetidin-3-yl]acetamide To a stirred solution of N-[4-(3-aminoazetidin-1-yl)phenyl]-5-fluoro-4-(1-isopropyl-2-methyl-1H-imidazol-5-yl)pyrimidin-2-amine (Example 140; 110 mg, 0.29 mM) and triethylamine (44 µl, 0.317 mM) in dry DCM (4.0 ml), acetic anhydride (30 µl, 0.317 mM) was added. The reaction was stirred at room temperature under nitrogen for 2.5 hours. A few drops of MeOH were added and the solution stirred for 10 minutes. The reaction mixture was then diluted with more DCM and the solution extracted in turn with water (twice) and saturated sodium chloride. The organic layer was then dried with anhydrous sodium sulphate, filtered and evaporated. The crude product was triturated with ether, filtered washed with ether and dried to give the title compound as a yellow solid (99 mg, 81%). NMR 1.4 (d, 6H), 1.8 (s, 3H), 2.5 (s, 3H+DMSO), 3.5 (t, 2H), 4.05 (t, 2H), 4.53 (m, 1H), 5.43 (m, 1H), 6.4 (d, 2H), 7.33 (m, 3H), 8.42 (m, 2H), 9.08 (s, 1H); m/z 424.

Example 143

N-[1-(4-{[5-Fluoro-4-(1-isopropyl-2-methyl-1H-imidazol-5-yl)pyrimidin-2-yl]amino}phenyl)azetidin-3-yl]methanesulfonamide To a stirred solution of N-[4-(3-aminoazetidin-1-yl)phenyl]-5-fluoro-4-(1-isopropyl-2-methyl-1H-imidazol-5-yl)pyrimidin-2-amine (Example 140; 110 mg, 0.29 mM) and triethylamine (44 µl, 0.317 mM) in dry DCM (4.0 ml), methanesulphonyl chloride (25 µl, 0.317 mM) was added. The reaction was stirred at room temperature under nitrogen for 24 hours. The reaction was filtered and the filtered solid washed with DCM. This solid which was pure product was retained. The filtrate was taken and more DCM added. The solution was washed in turn with water (twice), saturated sodium chloride and then dried with anhydrous sodium sulphate, filtered and evaporated. The product so obtained was combined with the 1$^{st}$ batch of product and both were triturated with ether, filtered, washed with ether and dried to give the title compound as a yellow solid. NMR 1.4 (d, 6H), 2.6 (s, 3H), 2.9 (s, 3H), 3.55 (t, 2H), 4.13 (t, 2H), 4.25 (m, 1H), 5.37 (m, 1H), 6.4 (d, 2H), 7.33 (d, 2H), 7.58 (d, 1H), 7.75 (d, 1H), 8.5 (d, 1H), 9.22 (s, 1H); m/z 460.

Example 144

(3-Chloro-4-morpholin-4-yl-phenyl)-[4-(3-isopropyl-2-methyl-3H-imidazol-4-yl)-pyrimidin-2-yl]-amine The title compound was prepared using the procedure described in Example 112, employing N-(3-chloro-4-morpholin-4-yl-phenyl)-guanidine carbonate (Method 17; 500 mg, 1.97 mmol), and (2E)-3-(dimethylamino)-1-(1-isopropyl-2-methyl-1H-imidazol-5-yl)prop-2-en-1-one (Method 24 of WO 03/076436; 363 mg, 1.64 mmol). Yield: 412 mg,

Example 145

(3-Chloro-4-morpholin-4-yl-phenyl)-[5-fluoro-4-(3-isopropyl-2-methyl-3H-imidazol-4-yl)-pyrimidin-2-yl]-amine The title compound was prepared using the procedure described in Example 112, employing N-(3-chloro-4-morpholin-4-yl-phenyl)-guanidine carbonate (Method 17; 500 mg, 1.97 mmol), and (2Z)-3-(dimethylamino)-2-fluoro-1-(1-isopropyl-2-methyl-1H-imidazol-5-yl)prop-2-en-1-one (Method 14; 392 mg, 1.64 mmol). Yield: 203 mg, 30% as a white solid; NMR: 1.41 (d, 6H), 2.49 (s, 3H), 2.90 (t, 4H), 3.72 (t, 4H), 5.35 (m, 1H), 7.10 (d, 1H), 7.34 (d, 1H), 7.50 (dd, 1H), 7.73 (d, 1H), 8.52 (d, 1H), 9.51 (s, 1H); m/z 431.

Example 146

N-{4-[(2RS,6SR)-2,6-Dimethylmorpholin-4-yl]phenyl}-5-fluoro-4-(1-isopropyl-2-methyl-1H-imidazol-5-yl)pyrimidin-2-amine (2E)-3-(Dimethylamino)-1-(1-ethyl-2-methyl-1H-imidazol-5-yl)-2-fluoroprop-2-en-1-one (Method 15; 327 mg, 1.37 mmol) and N-[4-(cis-2,6-dimethylmorpholino)phenyl]guanidine bicarbonate salt (Method 20; 510 mg, 1.65 mmol) in 2-methoxyethanol (8 ml) were heated for 17 hours at 110° C. The reaction mixture was evaporated under reduced pressure and the residue purified by chromatography on silica gel with MeOH:DCM:EtOAc (4:48:48) to (10:45:45) to give the title compound, after trituration with isohexane, as a solid (274 mg 47.2%). NMR (CDCl$_3$) 1.26 (d, 6H), 1.44 (d, 6H), 1.68 (s, 2H), 2.39 (t, 2H), 2.58 (s, 3H), 3.39 (d, 2H), 3.82 (m, 2H), 5.57 (sept, 1H), 6.82 (s, 1H), 6.89 (d, 2H), 7.37 (d, 2H), 7.57 (d, 1H), 8.22 (d, 1H); m/z 425.

Example 147

(R)-1-{4-[4-(3-Isopropyl-2-methyl-3H-imidazol-4-yl)-pyrimidin-2-ylamino]-phenyl}-pyrrolidine-2-carboxylic acid cyclopropylamide (R)-1-(4-Guanidino-phenyl)-pyrrolidine-2-carboxylic acid cyclopropylamide (Method 63; 0.29 g, 1.0 mmol) and ((2E)-3-(dimethylamino)-1-(1-isopropyl-2-methyl-1H-imidazol-5-yl)prop-2-en-1-one, (Method 24 of WO 03/076436; 0.15 g, 0.68 mmol) were added to 2-methoxyethanol (4 ml) and heated at 200° C. for 2 hours in the microwave. The solvent was removed in vacuo and the gum was carefully chromatographed eluting with DCM, 1% MeOH/DCM, 2% MeOH/DCM and finally 3% MeOH/DCM to yield a yellow solid (110 mg, 36%). NMR (299.954 MHz, CDCl$_3$) 8.28 (d, 1H), 7.39 (d, 1H), 7.34 (s, 1H), 6.85-6.82 (m, 2H), 6.60-6.57 (m, 3H), 5.61 (septet, 1H), 3.96-3.92 (m, 1H), 3.62 (t, 1H), 3.19 (q, 1H), 2.76-2.67 (m, 1H), 2.56 (s, 3H), 2.30-2.22 (m, 2H), 2.07-1.84 (m, 1H), 1.47 (d, 6H), 0.78-0.70 (m, 2H), 0.45-0.38 (m, 2H); m/z 446.

Example 148

N-(3-Fluoro-4-morpholin-4-ylphenyl)-4-(1-isopropyl-2-methyl-1H-imidazol-5-yl)pyrimidin-2-amine (2E)-3-(Dimethylamino)-1-(1-isopropyl-2-methyl-1H-imidazol-5-yl)prop-2-en-1-one (Method 24 of WO 03/076436); (330 mg, 1.5 mmol) and N-(3-fluoro-4-morpholinophenyl)guanidine bicarbonate salt (Method 23; 540 mg, 1.8 mmol) in 2-methoxyethanol (10 ml) were heated for 49 hours at 100° C. The reaction mixture was evaporated under reduced pressure and the residue purified by chromatography on silica gel with MeOH:DCM (2:98 to 6:94) to give the title compound, after trituration with ether, as a solid (296 mg 50%). NMR (CDCl$_3$): 1.51 (d, 6H), 2.59 (s, 3H), 3.06 (t, 4H), 3.89 (t, 4H), 5.68 (sept, 1H), 6.91 (m, 2H), 7.08 (m, 2H), 7.38 (s, 1H), 7.57 (dd, 1H), 8.32 (d, 1H); m/z 397.

Example 149

5-Fluoro-N-(3-fluoro-4-morpholin-4-ylphenyl)-4-(1-isopropyl-2-methyl-1H-imidazol-5-yl)pyrimidin-2-amine (2E)-3-(Dimethylamino)-2-fluoro-1-(1-isopropyl-2-methyl-1H-imidazol-5-yl)prop-2-en-1-one (Method 14; 360 mg, 1.5 mmol) and N-(3-fluoro-4-morpholinophenyl)guanidine bicarbonate salt (Method 23; 540 mg, 1.8 mmol) in 2-methoxyethanol (10 ml) were heated for 45 hours at 100° C. The reaction mixture was evaporated under reduced pressure and the residue purified by chromatography on silica gel with MeOH:DCM (3:97) to give the title compound, after trituration with ether, as a solid (298 mg 48%). NMR (CDCl$_3$) 1.50 (d, 6H), 2.60 (s, 3H), 3.05 (t, 4H), 3.88 (t, 4H), 5.58 (sept, 1H), 6.90 (m, 2H), 6.95 (d, 1H), 7.08 (dd, 1H), 7.49 (dd, 1H), 7.59 (d, 1H), 8.26 (d, 1H); m/z 415.

Example 150

(R)-1-{4-[5-Fluoro-4-(3-isopropyl-2-methyl-3H-imidazol-4-yl)-pyrimidin-2-ylamino]-phenyl}-pyrrolidine-2-carboxylic acid cylopropylamide (R)-1-(4-Guanidino-phenyl)-pyrrolidine-2-carboxylic acid cyclopropylamide (Method 63) (0.36 g, 1.25 mmol) and (2Z)-3-(dimethylamino)-2-fluoro-1-(1-isopropyl-2-methyl-1H-imidazol-5-yl)prop-2-en-1-one (Method 14; 0.15 g, 0.63 mmol) were added to 2-methoxyethanol (4 ml) and heated at 200° C. for 2 hours in the microwave. The solvent was removed in vacuo and the gum was carefully chromatographed eluting with DCM, 1% MeOH/DCM, 2% MeOH/DCM and finally 3% MeOH/DCM to yield a yellow solid (180 mg, 62%). NMR (400.132 MHz, CDCl$_3$) 8.21 (d, 1H), 7.56 (d, 1H), 7.34 (d, 2H), 6.80 (s, 1H), 6.59 (m, 3H), 5.55 (septet, 1H), 3.62 (t, 1H), 3.21-3.15 (m, 1H), 2.74-2.68 (m, 1H), 2.58 (s, 3H), 2.28-2.22 (m, 2H), 2.05-1.98 (m, 1H), 1.96-1.86 (m, 1H), 1.45 (d, 6H), 0.79-0.72 (m, 2H), 0.44-0.37 (m, 2H); m/z 464.

Example 151

N-[(3R)-1-(4-{[5-Fluoro-4-(1-isopropyl-2-methyl-1H-imidazol-5-yl)pyrimidin-2-yl]amino}phenyl)pyrrolidin-3-yl]acetamide 4-((3R)-Acetamidopyrrolidin-1-yl)phenyl guanidine carbonate (Method 45; 1.25 g, 4.28 mmol) and (2Z)-3-(dimethylamino)-2-fluoro-1-(1-isopropyl-2-methyl-1H-imidazol-5-yl)prop-2-en-1-one (Method 14; 0.79 g, 3.3 mmol) in 2-methoxyethanol (20 ml) were heated at 115° C. for 18 hours under nitrogen. After evaporation under reduced pressure, chromatography on silica gel with MeOH/DCM (100 to 2.5:97.5) gave the title compound, after ether trituration, as a tan solid (612 mg, 43%). NMR: 1.38 (d, 6H), 1.80 (s, 3H), 1.80-

1.92 (m, 1H), 2.12-2.26 (m, 1H), 2.49 (s, 3H), 2.97-3.03 (m, 1H), 3.14-3.25 (m, 1H), 3.29-3.49 (m, 2H), 4.3-4.41 (m, 1H), 5.20-5.32 (m, 1H), 6.50 (d, 2H), 7.30 (s, 1H), 7.32 (d, 2H), 8.09 (d, 1H), 8.39 (s, 1H), 9.05 (s, 1H); m/z 438.

Example 152

N-[(3S)-1-(4-{[5-Fluoro-4-(1-isopropyl-2-methyl-1H-imidazol-5-yl)pyrimidin-2-yl]amino}phenyl)pyrrolidin-3-yl]acetamide The title compound was prepared by an identical procedure to Example 151 above, but using 4-((3S)-acetamidopyrrolidin-1-yl)phenyl guanidine carbonate (Method 51). NMR: 1.37 (d, 6H), 1.81 (s, 3H), 1.78-1.92 (m, 1H), 2.11-2.22 (m, 1H), 2.44 (s, 3H), 2.94-3.06 (m, 1H), 3.14-3.49 (m, 3H), 4.29-4.41 (m, 1H), 5.40-5.43 (m, 1H), 6.49 (d, 2H), 7.30 (s, 1H), 7.32 (d, 2H), 8.09 (d, 1H), 8.40 (d, 1H), 9.03 (s, 1H); m/z 438.

Example 153

N-{4-[(3S)-3-Aminopyrrolidin-1-yl]phenyl}-5-fluoro-4-(1-isopropyl-2-methyl-1H-imidazol-5-yl)pyrimidin-2-amine N-[(3S)-1-(4-{[5-Fluoro-4-(1-isopropyl-2-methyl-1H-imidazol-5-yl)pyrimidin-2-yl]amino}phenyl)pyrrolidin-3-yl]acetamide (Example 152; 0.49 g, 1.12 mmol) in isopropanol (20 ml), water (5 ml) and hydrochloric acid (2 ml) was heated at reflux under nitrogen for 18 hours. After evaporation under reduced pressure, the mixture was dissolved in water (15 ml) and adjusted to pH 9 with aqueous ammonium hydroxide solution. The solution was extracted with DCM (3×15 ml), dried and after evaporation under reduced pressure to give the title compound as a solid (0.42 g, 95%). NMR: 1.38 (d, 6H), 1.61-1.73 (m, 1H), 2.00-2.13 (m, 1H), 2.44 (s, 3H), 2.80-2.88 (m, 1H), 3.12-3.20 (m, 1H), 3.20-3.42 (m, 2H), 3.49-3.60 (m, 1H), 5.40-5.51 (m, 1H), 6.46 (d, 2H), 7.30 (d, 2H), 7.33 (s, 1H), 8.40 (s, 1H), 9.00 (s, 1H); m/z 396.

Example 154

(2S)-N-[(3S)-1-(4-{[5-Fluoro-4-(1-isopropyl-2-methyl-1H-imidazol-5-yl)pyrimidin-2-yl]amino}phenyl)pyrrolidin-3-yl]-2-hydroxypropanamide N-{4-[(3S)-3-Aminopyrrolidin-1-yl]phenyl}-5-fluoro-4-(1-isopropyl-2-methyl-1H-imidazol-5-yl)pyrimidin-2-amine (Example 153; 220 mg, 0.556 mmol), L—lactic acid (61 mg, 0.667 mmol), HOBt mono hydrate (103 mg, 0.667 mmol) and Hunig's base (0.12 ml, 0.667 mmol) in DCM (5 ml) were reacted with EDAC (128 mg, 0.667 mmol) at room temperature under nitrogen for 18 hours. The mixture was diluted with DCM (20 ml) and washed with water (20 ml), 1 N aqueous potassium hydroxide (20 ml) and saturated aqueous sodium chloride (15 ml). The mixture was dried and after evaporation under reduced pressure purified by HPLC on a Phenomenex column, (0-50% acetonitrile/water, 0.2% TFA). The fractions were diluted with water (20 ml), basified with solid potassium carbonate, and extracted twice with EtOAc/DCM (20 ml, 2:1). The solution was washed with saturated aqueous sodium chloride (15 ml), dried and after evaporation under reduced pressure gave the title compound as a yellow solid, (79 mg, 30%). NMR: 1.20 (d, 3H), 1.37 (d, 6H), 1.90-2.04 (m, 1H), 2.11-2.27 (m, 1H), 2.47 (s, 3H), 3.00-3.09 (m, 1H), 3.20-3.47 (m, 3H), 3.91-4.00 (m, 1H), 4.32-4.47 (m, 1H), 5.38 (s, 1H), 5.40-5.49 (m, 1H), 6.49 (d, 2H), 7.30 (s, 1H), 7.32 (d, 2H), 7.76 (d, 1H), 8.40 (d, 1H), 9.06 (s, 1H); m/z 468.

Example 155

N-[(3S)-1-(4-{[5-Fluoro-4-(1-isopropyl-2-methyl-1H-imidazol-5-yl)pyrimidin-2-yl]amino}phenyl)pyrrolidin-3-yl]-2-hydroxyacetamide The title compound was prepared (38 mg, 15%), using a procedure analogous to Example 154, starting from N-{4-[(3S)-3-aminopyrrolidin-1-yl]phenyl}-5-fluoro-4-(1-isopropyl-2-methyl-1H-imidazol-5-yl)pyrimidin-2-amine (Example 153; 220 mg, 0.556 mmol) and glycolic acid (51 mg, 0.667 mmol). NMR: 1.39 (d, 6H), 1.91-2.04 (m, 1H), 2.13-2.25 (m, 1H), 2.44 (s, 3H), 3.04-3.12 (m, 1H), 3.18-3.47 (m, 3H), 3.80 (d, 2H), 4.38-4.47 (m, 1H), 5.32 (t, 1H), 5.40-5.52 (m, 1H), 6.50 (d, 2H), 7.30 (s, 1H), 7.35 (d, 2H), 7.82 (d, 1H), 8.40 (d, 1H), 9.04 (s, 1H); m/z 454.

Example 156

N-{4-[(3R)-3-Aminopyrrolidin-1-yl]phenyl}-5-fluoro-4-(1-isopropyl-2-methyl-1H-imidazol-5-yl)pyrimidin-2-amine The title compound was prepared in identical fashion, (0.45 g, 99%), to Example 153 starting from N-[(3R)-1-(4-{[5-fluoro-4-(1-isopropyl-2-methyl-1H-imidazol-5-yl)pyrimidin-2-yl]amino}phenyl)pyrrolidin-3-yl]acetamide (Example 151). NMR: 1.36 (d, 6H), 1.61-1.76 (m, 1H), 2.00-2.16 (m, 1H), 2.47 (s, 3H), 2.79-2.89 (m, 1H), 3.14-3.41 (m, 3H), 3.28 (brs, 2H), 3.50-3.60 (m, 1H), 5.40-5.52 (m, 1H), 6.44 (d, 2H), 7.31 (d, 2H), 7.35 (s, 1H), 8.39 (d, 1H), 9.00 (s, 1H); m/z 396.

Example 157

(2S)-N-[(3R)-1-(4-{[5-Fluoro-4-(1-isopropyl-2-methyl-1H-imidazol-5-yl)pyrimidin-2-yl]amino}phenyl)pyrrolidin-3-yl]-2-hydroxypropanamide The title compound was prepared (15 mg, 6%), was prepared using a procedure analogous to Example 154 starting from N-{4-[(3R)-3-aminopyrrolidin-1-yl]phenyl}-5-fluoro-4-(1-isopropyl-2-methyl-1H-imidazol-5-yl)pyrimidin-2-amine (Example 156; 220 mg, 0.556 mmol) and L—lactic acid (61 mg, 0.667 mmol). NMR: 1.20 (d, 3H), 1.36 (d, 6H), 1.89-2.01 (m, 1H), 2.14-2.22 (m, 1H), 2.43 (s, 3H), 3.02-3.10 (m, 1H), 3.14-3.48 (m, 3H), 3.92-4.03 (m, 1H), 4.34-4.46 (m, 1H), 5.35 (d, 2H), 5.41-5.53 (m, 1H), 6.49 (d, 2H), 7.30 (s, 1H), 7.32 (d, 2H), 8.40 (d, 1H), 9.05 (s, 1H); m/z 468.

Example 158

N-[(3R)-1-(4-{[5-Fluoro-4-(1-isopropyl-2-methyl-1H-imidazol-5-yl)pyrimidin-2-yl]amino}phenyl)pyrrolidin-3-yl]-2-hydroxyacetamide The title compounds was prepared (38 mg, 15%), was prepared using a procedure analogous to Example 155 starting from N-{4-[(3R)-3-aminopyrrolidin-1-yl]phenyl}-5-fluoro-4-(1-isopropyl-2-methyl-1H-imidazol-5-yl)pyrimidin-2-amine (Example 156; 220 mg, 0.556 mmol) and glycolic acid (51 mg, 0.667 mmol). NMR: 1.39 (d, 6H), 1.92-2.04 (m, 1H), 2.14-2.26 (m, 1H), 2.44 (s, 3H), 3.04-3.13 (m, 1H), 3.18-3.49 (m, 3H), 3.80 (d, 2H), 4.46-4.51 (m, 1H), 5.34 (t, 1H), 5.42-5.51 (m, 1H), 6.49 (d, 2H), 7.31 (d, 1H), 7.35 (d, 2H), 7.82 (d, 1H), 8.41 (d, 1H), 9.06 (s, 1H); m/z 454.

Example 159

(S)-1-{4-[5-Fluoro-4-(3-isopropyl-2-methyl-3H-imidazol-4-yl)-pyrimidin-2-ylamino]-phenyl}-pyrrolidine-2-carboxylic acid dimethylamide (S)-1-(4-Guanidino-phenyl)-pyrrolidine-2-carboxylic acid dimethylamide (Method 54; 0.5 g, 1.82 mmol) and (2Z)-3-(dimethylamino)-2-fluoro-1-(1-isopropyl-2-methyl-1H-imidazol-5-yl)prop-2-en-1-one (Method 14; 0.2 g, 0.83 mmol) were heated at reflux in butanol (7 ml) overnight. LCMS indicated only 7% product. The reaction was transferred to a microwave tube and heated at 200° C. for 2 hours. LCMS indicated 15% starting material and mainly product. The solvent was removed in vacuo and chromatographed. The product was purified by HPLC and the required fractions were combined and basified with $K_2CO_3$ (0.5 g), extracted with DCM (2×50 ml), dried and the solvent removed in vacuo to yield a yellow solid (101 mg, 31%). NMR (400.132 MHz, $CDCl_3$) 8.18 (d, 1H), 7.56 (d, 1H), 7.24 (d, 2H), 6.69 (s, 1H), 6.42 (d, 2H), 5.59 (septet, 1H), 4.51 (dd, 1H), 3.64 (dt, 1H), 3.41 (q, 1H), 3.16 (s, 3H), 2.98 (s, 3H), 2.56 (s, 3H), 2.38-2.28 (m, 1H), 2.25-2.14 (m, 1H), 2.08-1.98 (m, 2H), 1.39 (t, 6H); m/z 452.

Example 160

(R)-1-{4-[5-Fluoro-4-(3-isopropyl-2-methyl-3H-imidazol-4-yl)-pyrimidin-2-ylamino]-phenyl}-pyrrolidine-2-carboxylic acid methylamide (R)-1-(4-Guanidino-phenyl)-pyrrolidine-2-carboxylic acid methylamide (Method 59; 0.22 g, 0.82 mmol) and (2Z)-3-(dimethylamino)-2-fluoro-1-(1-isopropyl-2-methyl-1H-imidazol-5-yl)prop-2-en-1-one (Method 14; 0.15 g, 0.63 mmol) were added to 2-methoxyethanol (4 ml) and heated at 200° C. for 2 hours in the microwave. Solvent was removed in vacuo and chromatographed. The product was passed purified by HPLC, and the required fractions were combined and basified with $K_2CO_3$ (0.5 g), extracted with DCM (2×50 ml), dried and solvent removed in vacuo to yield a yellow solid (110 mg, 40%). NMR (400.132 MHz, $CDCl_3$) 8.21 (d, 1H), 7.56 (d, 1H), 7.34 (d, 2H), 6.79 (s, 1H), 6.60 (d, 2H), 6.56 (s, 1H), 5.56 (septet, 1H), 3.99 (t, 1H), 3.64 (t, 1H), 3.20 (q, 1H), 2.80 (d, 3H), 2.58 (s, 3H), 2.29-2.24 (m, 2H), 2.06-1.89 (m, 2H), 1.45 (d, 6H); m/z 438.

Example 161

(R)-1-{4-[4-(3-Isopropyl-2-methyl-3H-imidazol-4-yl)-pyrimidin-2-ylamino]-phenyl}-pyrrolidine-2-carboxylic acid methylamide (R)-1-(4-Guanidino-phenyl)-pyrrolidine-2-carboxylic acid methylamide (Method 59; 0.27 g, 1.0 mmol) and of (2E)-3-(dimethylamino)-1-(1-isopropyl-2-methyl-1H-imidazol-5-yl)prop-2-en-1-one, (Method 24 of WO 03/076436; 0.15 g, 0.68 mmol) were added to 2-methoxyethanol (4 ml) and heated at 200° C. for 2 hours in the microwave. The solvent was removed in vacuo and the gum was carefully chromatographed eluting with DCM, 1% MeOH/DCM, 2% MeOH/DCM and finally 3% MeOH/DCM to yield a yellow solid (101 mg, 35%). NMR (400.132 MHz, $CDCl_3$) 8.28 (d, 1H), 7.39 (d, 2H), 7.34 (s, 1H), 6.89 (s, 1H), 6.83 (d, 1H), 6.61-6.57 (m, 3H), 5.62 (septet, 1H), 3.99 (t, 1H), 3.65 (t, 1H), 3.24-3.17 (m, 1H), 2.80 (d, 3H), 2.55 (s, 3H), 2.29-2.24 (m, 2H), 2.06-1.89 (m, 2H), 1.46 (d, 6H); m/z 420.

Example 162

N-[(3R)-1-(4-{[4-(1-Isopropyl-2-methyl-1H-imidazol-5-yl)pyrimidin-2-yl]amino}phenyl)pyrrolidin-3-yl]acetamide 4-((3R)-Acetamidopyrrolidin-1-yl)phenyl guanidine trifluoroacetate salt (Method 70; 1.79 g, 4.55 mmol), (2E)-3-(dimethylamino)-1-(1-isopropyl-2-methyl-1H-imidazol-5-yl)prop-2-en-1-one (Method 24 of WO 03/076436; 1.01 g, 4.55 mmol) in 2-methoxyethanol (20 ml) and DIPEA (1.74 ml, 10 mmol) were heated at 115° C. for 20 hours under nitrogen. After evaporation under reduced pressure, chromatography on silica gel with MeOH/DCM (100 to 5:95) gave the title compound, after ether trituration, as a yellow solid (165 mg, 9%). NMR: 1.39 (d, 6H), 1.75-1.90 (m, 1H), 1.80 (s, 3H), 2.11-2.22 (m, 1H), 2.44 (s, 3H), 2.98-3.02 (m, 1H), 3.16-3.48 (m, 3H), 4.28-4.37 (m, 1H), 5.64-5.75 (m, 1H), 6.50 (d, 2H), 6.89 (d, 1H), 7.35 (s, 1H), 7.37 (d, 1H), 8.09 (d, H), 8.98 (s, H) m/z: 420.

Example 163

N-[(3R)-1-(2-Fluoro-4-{[4-(1-isopropyl-2-methyl-1H-imidazol-5-yl)pyrimidin-2-yl]amino-2-fluoro}phenyl)pyrrolidin-3-yl]acetamide The title compound (0.24 g, 10%), was prepared by an analogous route to Example 162, starting from 2-fluoro-4-((3R)-acetamidopyrrolidin-1-yl)phenyl guanidine carbonate (Method 69, 1.16 g, 5.23 mmol) and (2E)-3-(dimethylamino)-1-(1-isopropyl-2-methyl-1H-imidazol-5-yl)prop-2-en-1-one, (Method 24 of WO 03/076436, 2.43 g, 7.84 mmol). NMR: 2.41 (d, 6H), 1.70-1.86 (m, 1H), 1.80 (s, 3H), 2.07-2.18 (m, 1H), 2.46 (s, 3H), 3.04-3.12 (m, 1H), 3.19-3.28 (m, 1H), 3.32-3.49 (m, 2H), 4.22-4.39 (m, 1H), 5.62-5.72 (m, 1H), 6.68 (t, 1H), 6.98 (d, 2H), 7.21 (d, 1H), 7.39 (s, 1H), 7.50 (d, 1H), 8.07 (d, 1H), 8.32 (d, 1H), 9.24 (s, 1H); m/z 438.

Preparation of Starting Materials

Method 1

N-{4-[4-(Methylsulphonyl)piperazin-1-yl]phenyl}guanidine

1-Methylsulphonyl-4-(4-nitrophenyl)piperazine [J. Med. Chem. 20 (8) 987-996 (1977)] (24 g) in EtOH (250 ml) was hydrogenated over 10% Pd/carbon (2.4 g) at ambient temperature and pressure. The reaction was filtered and the catalyst and insoluble solid were washed with MeOH:2N hydrochloric acid (100:100 ml). Evaporation under reduced pressure gave the aniline hydrochloride as an orange solid (19.8 g 81%). M/z 256.

A mixture of the aniline (4.7 g 16.1 mmol) and cyanamide (800 mg 19.0 mmol) in EtOH (25 ml) and 1,4-dioxane (25 ml) were heated at 90° C.-95° C. for a total of 19 hours. Extra cyanamide (450 mg) and EtOH (10 ml) were added after 5.5 hours. The reaction mixture was evaporated under reduced pressure. Water (100 ml) was added to the residue before basifying with 40% sodium hydroxide (pH>11). The solid was filtered off, washed with a little cold water, dried on a filter then transferred to a beaker. The residue was triturated with acetone (50 ml), filtered and air dried to give the title compound (3.2 g 58%). NMR: 2.89 (s, 3H), 3.08 (m, 4H), 3.21 (m, 4H), 3.30 (b s, 4H), 6.73 (d, 2H), 6.73 (d, 2H); m/z 298.

Method 2

N-[4-(4-Acetylpiperazin-1-yl)phenyl]guanidine bicarbonate salt

1-Acetyl-4-(4-nitrophenyl)piperazine [J. Med. Chem. 20 (8) 987-996 (1977)] (20.8 g) in EtOH (200 ml) was hydrogenated over 10% Pd/carbon (2.1 g) at ambient temperature and pressure. The catalyst was filtered off, washed with EtOH (500 ml) and evaporation under reduced pressure to give the aniline as a purple solid, 22 g (still wet).

The aniline (5.0 g 22.8 mmol) was stirred in dry 1,4-dioxane (55 ml) and EtOH (20 ml). 4N HCl in dioxane (6.0 ml 25 mmol) was added then, after 3 to 4 minutes, cyanamide (1.6 g 38.1 mmol) and extra EtOH (4 ml) were added. The reaction was heated at 95° C. for 17.5 hours then extra cyanamide (300 mg) and 4N HCl/dioxane (2 ml) were added. The reaction was continued with heating for 6 hours. After evaporation under reduced pressure, the solid was triturated with ether (2×70 ml) and air dried. The solid was dissolved in water (40 ml), slowly added saturated sodium hydrogen carbonate solution (75 ml) with stirring. After 21 hour, the solid was collected by filtration, washed with acetone (2×40 ml) and dried under vacuum. (5.7 g 77%). NMR: 2.01 (s, 3H), 2.98 (t, 2H), 3.05 (t, 2H), 2.9-3.8 (v b s, exchangeables), 3.54 (m, 4H), 6.81 (d, 2H), 6.88 (d, 2H); m/z 262.

Method 3

(2E)-2-Chloro-3-(dimethylamino)-1-(1-isopropyl-2-methyl-1H-imidazol-5-yl)prop-2-en-1-one Benzyltrimethylammonium dichloroiodate (2.6 g 7.5 mmol) was added in portions to a stirred solution of (2E)-3-(dimethylamino)-1-(1-isopropyl-2-methyl-1H-imidazol-5-yl)prop-2-en-1-one (Method 24 of WO 03/076436; 1.1 g 5 mmol) in MeOH/DCM (15/30 ml) at room temperature. After 1 hour water (10 ml) and DCM (20 ml) were added followed after a further 30 minutes by saturated sodium hydrogen carbonate solution (20 ml). The organics were separated, re-extracted the aqueous with DCM (25 ml). The combined organics were washed with 5% (w/v) sodium thiosulphate solution (30 to 35 ml) and brine (25 ml), dried (Na$_2$SO$_4$) and evaporated to give the title compound as an oil (crude yield 1.68 g still wet). M/z 256.

Method 4

N-[4-(Morpholino)phenyl]guanidine bicarbonate salt

4-Morpholino aniline (1.78 g 10 mmol) and cyanamide (420 mg 10 mmol) were stirred in 1,4-dioxane (17.5 ml). 7N HCl in 1,4-dioxane (2.5 ml) was slowly added before heating at 95° C. for 11 hours. The reaction mixture was evaporated under reduced pressure and the solid triturated with ether before air-drying overnight. This solid was treated with water (20 ml) and stirred during slow addition of saturated aqueous sodium hydrogen carbonate solution (15 ml). The solid was collected by filtration, washed with acetone (15 ml) and air dried to give the title compound 2.3 g 80%. NMR 2.95 (4H, m), 3.39 (exchangeables, v brs), 3.68 (4H, m), 6.68 (2H, d), 6.71 (2H, d); m/z 221.

Method 5

2-Amino-5-chloro-4-(1-isopropyl-2-methyl-1H-imidazol-5-yl)pyrimidine

A solution of 2-amino-4-(1-isopropyl-2-methyl-1H-imidazol-5-yl)pyrimidine (Method 39 of WO 03/076436; 0.5 g, 2.3 mmol) and N-chlorosuccinimide (0.4 g, 3 mmol) in acetic acid (5 ml) was stirred at 65° C. under nitrogen for 2 hours. Then the reaction mixture was allowed to cool down to room temperature and the solvent was removed under vacuum. The crude was taken up in EtOAc and water then portions of solid potassium carbonate were added to this stirred biphasic solution until pH 8-9 was reached. The two layers were separated, the aqueous layer was extracted once with EtOAc then the organics were combined, washed with brine and dried. Removal of the solvent left a residue, which was purified on silica (MeOH/DCM/EtOAc, from 0/50/50 to 6/47/47). Triturating the foam in ether gave a white solid, which was filtered off. (0.49 g, 85%). NMR (CDCl$_3$): 1.51 (d, 6H), 2.55 (s, 3H), 4.85 (septuplet, 1H), 5.01 (b s, 2H), 7.48 (s, 1H), 8.31 (s, 1H); m/z 252 ($^{35}$Cl), 254 ($^{37}$Cl); m/z 250 ($^{35}$Cl), 252 ($^{37}$Cl).

Method 6

4-[N-(Propionyl)-N-(isopropyl)amino]-5-methylisoxazole

Triethylamine (1.0 eq.) was added dropwise over 45 mins to a solution of N-isopropyl-5-methylisoxazol-4-amine (Method 1 of WO 03/76436; 258 g, 1.0 eq.) and n-propionyl chloride (1.0 eq) in DCM (8.6 vol.eq.) at −3° C. The reaction was then stirred at 0° C. for 20 mins and then left to warm to room temperature overnight. Water (10 vol.eq) was added and the mixture was then stirred for 30 mins. The organic layer was separated and washed with water (2×10 vol.eq.), 2M HCl (3×10 vol.eq.), brine (10 vol.eq.), dried, filtered and the solvent was then removed in vacuo from the filtrate to leave a yellow oil which crystallised on standing (330 g, 91%). NMR 0.91 (3H, t), 0.95 (6H, b s), 1.9 (2H, q), 2.35 (3H, s), 4.8 (1H, septuplet), 8.61 (1H, s).

Method 7

N-[(E)-1-Acetyl-2-aminoethenyl]-N-isopropylpropanamide

4-[N-(Propionyl)-N-(isopropyl)amino]-5-methylisoxazole (Method 6; 330 g, 1.0 eq.) was stirred under hydrogen (1.0 eq), with 10% palladium on carbon (0.1 eq.) in EtOH (10 vol.eq.) at 25° C. overnight. The catalyst was removed by filtration and the EtOH was removed in vacuo to leave an off white solid (351 g, 98%). This was used without further purification.

Method 8

1-Isopropy-2-ethyl-5-acetylimidazole

N-[(E)-1-Acetyl-2-aminoethenyl]-N-isopropylpropanamide (Method 7; 373 g, 1.0 eq.) was stirred with sodium hydroxide (1.4 eq.) in EtOH (4 vol.eq.). The reaction was heated to reflux (85° C.) and stirred overnight. Ammonium chloride (2.0 eq.) was then added and this was stirred for 2 hours (the consistency of the reaction changed to a fine precipitate). The reaction was then allowed to cool, the solid was filtered off and discarded, and the solvent was then removed in vacuo. Acetone was then added to the residue, the solid was filtered off and discarded. The solvent was then removed in vacuo. Prep chromatography was then performed by eluting with 5% MeOH/DCM, to leave a brown oil (290 g, 86%). NMR 1.23 (3H, t), 1.43 (6H, d), 2.40 (3H, s), 2.77 (2H, q), 5.0 (1H, b s), 7.87 (1H, s).

Method 9

5-(3-Dimethylaminoprop-2-en-1-oyl)-1-isopropyl-2-ethylimidazole

1-Isopropy-2-ethyl-5-acetylimidazole (Method 8; 290 g, 1.0 eq.) was stirred with DMF DMA (2.0 eq.) in DMF (15 vol.eq.). The reaction was heated to 130° C. and stirred overnight. The reaction was allowed to cool and the solvent removed in vacuo. The residue was triturated with ether and the brown solid filtered off, washed with ether, this process was repeated. The filtrates were then combined and purified by prep chromatography eluting with 5% MeOH/DCM to give a yellow solid (223 g, 59%). NMR 1.24 (3H, t), 1.46 (6H, d), 2.73 (2H, q), 2.96 (6H, b s), 5.09 (1H, septuplet), 5.56 (1H, d), 7.51 (1H, s), 7.53 (1H, d).

Method 10

4-(N-Butyryl-N-ethylamino)-5-methylisoxazole

To a stirred, ice cooled solution of 4-ethylamino-5-methylisoxazole (Method 5 of WO 03/76436; 49.6 g, 305 mM) and triethylamine (77.0 g, 763 mM, 107 ml) in DCM (800 ml), was slowly added a solution of n-butyryl chloride (35.5, 333 mM, 35 ml) in DCM (100 ml). There was a moderate exotherm. The solution was allowed to warm to ambient temperature and stir for 1 hour. The reaction mixture was washed with water, 2N HCl, brine, sat. NaHCO$_3$ and brine. It was dried and the solvent was evaporated to give the title compound as an oil, which crystallized to a waxy solid (45.1 g, 75%). NMR (300 Mz, DMS0-d6): 0.78 (t, 3H), 0.96 (t, 3H), 1.44 (sext, 2H), 1.93 (t, 2H), 2.33 (s, 3H), 3.49 (q, 2H), 8.68 (s, 1H); m/z 197.

Method 11

N-[(E)-1-Acetyl-2-aminoethenyl]-N-ethylbutanamide

A solution of 4-(N-butyryl-N-ethylamino)-5-methylisoxazole (Method 10; 45 g, 230 mM) in EtOH (1.5 l) was hydrogenated over 10% Pd/C (11.25 g) at 4 bar. The catalyst was filtered off and the solution was evaporated. The residue was triturated with ether and the crystalline intermediate was filtered off (33.94 g). This was used without further purification.

Method 12

1-Ethyl-2-propyl-5-acetylimidazole

A solution of N-[(E)-1-acetyl-2-aminoethenyl]-N-ethylbutanamide (Method 11; 33.9 g, 171 mM) and NaOH (8.2 g, 205 mM) in EtOH (400 ml) was heated under reflux for 4 hours. NH$_4$Cl (11.9 g, 222 mM) was added to the hot solution, which was allowed to cool and stir for 48 hours. The reaction mixture was filtered and the solution was evaporated. The residue was taken into ether and filtered again. The solution was evaporated to give the title compound as a yellow oil (30.55 g, 74%). NMR (300 Mz, DMS0-d6): 0.92 (t, 3H), 1.17 (t, 3H), 1.70 (sext, 2H), 2.37 (s, 3H), 2.64 (t, 2H), 4.23 (q, 2H), 7.83 (s, 1H); m/z 181.

Method 13

5-(3-Dimethylaminoprop-2-en-1-oyl)-1-ethyl-2-propylimidazole

A solution of 1-ethyl-2-propyl-5-acetylimidazole (Method 12; 30.5 g, 169 mM) and DMF DMA (49.7 g, 338 mM, 58 ml) in DMF (100 ml) was stirred at 130° C. for 18 hours, allowing distillation of the EtOH generated. On cooling, the product crystallized from the reaction mixture and was filtered and washed with ether (20.94 g). A second crop was obtained on evaporating the solvent and triturating with ether (8.8 g) (29.74 g, 75%). NMR (300 Mz, DMS0-d6): 0.92 (t, 3H), 1.18 (t, 3H), 1.70 (sext, 2H), 2.60 (t, 2H), 2.94 (brs, 6H), 4.30 (q, 2H), 5.56 (d, 1H), 7.50 (d, 1H), 7.56 (s, 1H); m/z 236.

Method 14

(2Z)-3-(Dimethylamino)-2-fluoro-1-(1-isopropyl-2-methyl-1H-imidazol-5-yl)prop-2-en-1-one To a stirred solution of (2E)-3-(dimethylamino)-1-(1-isopropyl-2-methyl-1H-imidazol-5-yl)prop-2-en-1-one, (Method 24 of WO 03/076436; 5.53 g, 25 mmol) in MeOH (100 ml) at ambient temperature, was added in portions over 5 mins, Selectfluor (14.16 g, 40 mmol). The temperature was maintained at 25-30° C. by slight cooling. After stirring for 90 min the reaction mixture was cooled in ice/acetone and filtered. The filtrate was evaporated under reduced pressure and the residue was taken into DCM. It was washed with aq. ammonia, brine, dried over anhydrous Na$_2$SO$_4$ and evaporated under reduced pressure. The title compound was isolated by MPLC on silica gel using two separate columns (10% EtOH/EtOAc, then 3.5% EtOH/DCM) as a golden viscose oil, which crystallized on standing over several weeks. Yield=2.50 g (42%). NMR (300 Mz): 1.40 (d, 6H), 2.38 (s, 3H), 3.05 (s, 6H), 4.70 (septet, 1H), 6.96 (d, 1H), 7.08 (s, 1H); $^{19}$F NMR (376 MHz): −166.7 (d); m/z 240.

Method 15

(2Z)-3-(Dimethylamino)-1-(1-ethyl-2-methyl-1H-imidazol-5-yl)-2-fluoroprop-2-en-1-one The title compound was prepared by the procedure of Method 14 above on a 46 mM scale of (2E)-3-(dimethylamino)-1-(1-ethyl-2-methyl-1H-imidazol-5-yl)prop-2-en-1-one (Method 16 of WO 02/20512). The title compound was isolated by MPLC on silica gel using two separate columns (5% EtOH/DCM, then 10% EtOH/EtOAc) and crystallized readily on trituration with ether. Yield=3.93 g (38%). NMR (300 Mz): 1.2 (t, 3H), 2.38 (s, 3H), 3.05 (s, 6H), 4.18 (q, 2H), 6.96 (d, 1H), 7.34 (s, 1H); $^{19}$F NMR (376 MHz) −168.2 (d); m/z 226.

Method 16

(2Z)-1-(1-Cyclobutyl-2-methyl-1H-imidazol-5-yl)-3-(dimethylamino)-2-fluoroprop-2-en-1-one The title compound was prepared from (2E)-1-(1-cyclobutyl-2-methyl-1H-imidazol-5-yl)-3-(dimethylamino)prop-2-en-1-one (Method 37 of WO 03/076435; 3.0 g) by the procedure of Method 14. Purification by silica gel chromatography eluting with EtOH/EtOAc (5:95 to 10:90) afforded the title compound as a yellow oil (1.64 g, 51%). NMR (CDCl$_3$): 1.73-1.88 (m, 2H), 2.47 (s, 3H), 2.45-2.55 (m, 4H), 3.10 (s, 6H), 5.00 (quintet, 1H), 6.87 (d, 1H), 7.23 (d, 1H); m/z 252.

Method 17

N-(3-Chloro-4-morpholin-4-yl-phenyl-guanidine bicarbonate salt

The title compound was prepared using the procedure described above for Method 4 using N-(4-amino-2-chlorophenyl)morpholine (1.1 g, 5.19 mmol), cyanamide (273 mg, 6.49 mmol), 4.0M HCl in dioxane (1.62 ml, 6.49 mmol) and dioxane (30 ml). Yield: 820 mg, 50%. NMR: 2.85 (t, 4H), 3.70 (t, 4H), 6.73 (dd, 1H), 6.81 (d, 1H), 7.00 (d, 1H).

Method 18

1-(Cis-2,6-dimethylmorpholino)-4-nitrobenzene

1-Fluoro-4-nitrobenzene (4.9 g, 34.75 mmol) was added to cis-2,6-dimethylmorpholine (44.4 g, 38.26 mmol) and anhydrous potassium carbonate (2.5 g, 18.12 mmol) in acetonitrile (50 ml). The reaction was heated under reflux for 19 hours, cooled, filtered and the solid washed with acetonitrile. Evaporation of the filtrate gave the title compound as a yellow solid. (8.1 g, 99%) NMR (CDCl$_3$) 1.28 (d, 6H), 2.61 (t, 2H), 3.66 (td, 2H), 3.76 (m, 2H), 6.82 (d, 2H), 8.13 (d, 2H); m/z 237.

Method 19

4-(Cis-2,6-dimethylmorpholino)aniline 1-(Cis-2,6-dimethylmorpholino)-4-nitrobenzene (Method 18, 8 g) in EtOH (100 ml) was reduced with hydrogen over 10% palladium/carbon (800 mg) at 50° C. After filtering off the catalyst and washing with EtOH, evaporation of the filtrate gave the title compound as a red/brown oil, which started to solidify after several days (quantitative yield). NMR (CDCl$_3$) 1.23 (d, 6H), 2.33 (t, 2H), 3.25 (d, 2H), 3.81 (m, 2 h), 6.65 (d, 2H), 6.79 (d, 2H); m/z 207.

Method 20

N-[4-(Cis-2,6-dimethylmorpholino)phenyl]guanidine bicarbonate salt 4-(Cis-2,6-dimethylmorpholino)aniline (Method 19; 6 g, 29.10 mmol) and cyanamide (1.5 g, 35.71 mmol) were stirred in 1,4-dioxane (45 ml). 4N HCl in 1,4-dioxane (8.8 ml, 35.2 mmol) was slowly added before heating at 100° C. for 1.75 hours. The reaction mixture was evaporated under reduced pressure and the residue triturated with ether. The resulting gum was treated with water (30 ml) and stirred during slow addition of saturated aqueous sodium hydrogen carbonate solution (40 ml). The solid was collected by filtration, washed with acetone (2×25 ml) and air dried to give the title compound (6.4 g 71%). NMR 1.15 (d, 6H), 2.21 (t, 2H), 3.48 (td, 2H), 3.68 (m, 2H), 6.85 (d, 2H), 6.89 (brd, 2H); m/z 249.

Method 21

1-Fluoro-2-morpholino-5-nitrobenzene 1,2-Difluoro-4-nitrobenzene (8.0 g, 50 mmol) was added to morpholine (4.85 g, 55.7 mmol) and anhydrous potassium carbonate (3.85 g, 27.9 mmol) in acetonitrile (75 ml). The reaction was heated at 85° C. for 3 hours, cooled, filtered and the solid washed with EtOAc (50 ml). Evaporation of the filtrate, trituration with isohexane and filtration gave the title compound as a solid (11.2 g, 98%). NMR (CDCl$_3$): 3.28 (t, 4H), 3.88 (t, 4H), 6.92 (t, 1H), 7.92 (dd, 1H), 8.00 (m, 1H); m/z 227.

Method 22

3-Fluoro-4-morpholinoaniline

1-Fluoro-2-morpholino-5-nitrobenzene (Method 21; 9 g) in EtOH:EtOAc (50:50 ml) was reduced with hydrogen over 10% palladium/carbon (800 mg). After filtering off the catalyst and washing with EtOH, evaporation of the filtrate gave the title compound as a brown solid (quantitative yield). NMR (CDCl$_3$) 2.96 (t, 4H), 3.55 (brs, 2H), 3.84 (t, 4H), 6.41 (d/s, 2H), 6.79 (t, 1H); m/z 197.

Method 23

N-(3-Fluoro-4-morpholinophenyl)guanidine bicarbonate salt

3-Fluoro-4-morpholinoaniline (Method 22; 7.8 g, 39.8 mmol) and cyanamide (2.1 g, 50 mmol) were stirred in 1,4-dioxane:EtOH (75:7.5 ml). 4N HCl in 1,4-dioxane (11.9 ml, 47.6 mmol) was slowly added before heating at 95° C. for 6 hours. The reaction mixture was evaporated under reduced pressure and the residue triturated with ether. The resulting solid was treated with water (35 ml) and stirred during slow addition of saturated aqueous sodium hydrogen carbonate solution (60 ml). The solid was collected by filtration, washed with cold water (10 ml) then acetone (2×25 ml) and air dried to give the title compound (10.9 g 91%) NMR 2.90 (t, 4H), 3.72 (t, 4H), 5.24 (brs, 4H), 6.52 (d/s, 1H), 6.54 (t, 1H), 6.87 (t, 1H); m/z 239.

Method 24

1-Acetyl-4-(2-chloro-4-nitrophenyl)piperazine

2-Chloro-1-fluoro-4-nitrobenzene (10 g, 57 mmol) and 1-acetylpiperazine (14.6 g, 114 mmol) were heated neat at 55° C. for 1 h. Then the reaction mixture was allowed to cool down to room temperature. The viscous orange solution was diluted with EtOAc and water. The organics were washed with water (3 times), brine, dried and evaporation of the solvent gave an orange oil which was triturated with isohexane. After evaporation of solvent the title compound was obtained as a yellow solid which was dried overnight in vac oven at 50° C. (15.68 g, 97%). It was used without further purification. NMR (400 MHz) 2.03 (d, 3H), 3.18 (dt, 4H), 3.62 (m, 4H), 7.30 (d, 1H), 8.17 (dd, 1H), 8.26 (d, 1H); m/z 284-286.

Method 25

1-Acetyl-4-(2-methyl-4-nitrophenyl)piperazine

1-Butyl-3-methylimidazolium tetrafluoroborate (1.75 g, 7.74 mmol) was added to a stirred solution of 1-fluoro-2-methyl-4-nitrobenzene (12 g, 77.35 mmol) and 1-acetylpiperazine (39.7 g, 309.4 mmol) in acetonitrile (3 ml). The reaction mixture was then heating at 95° C. overnight. The reaction mixture was allowed to cool down to room temperature. The solution was diluted with EtOAc and water. The precipitate formed was filtered off to give a solid corresponding to the required product. The organics were washed with water (4 times), brine, dried and evaporation of solvent to give a solid. Both solids were combined and after trituration with isohexane/ether and filtration, the title compound was obtained as a yellow solid which was dried in vac oven overnight at 50° C. (19.61 g, 96%). NMR (400 MHz) 2.06 (s, 3H), 2.38 (s, 3H), 2.99 (dt, 4H), 3.61 (m, 4H), 7.14 (d, 1H), 8.04 (dd, 1H), 8.07 (d, 1H); m/z 264.

Method 26

1-Acetyl-4-(2-fluoro-4-nitrophenyl)piperazine

A stirred solution of 1-(2-fluoro-4-nitrophenyl)piperazine (15 g, 66.6 mmol) in DCM (160 ml) was cooled to 0° C. Triethylamine was then added (11.23 ml, 79.92 mmol) followed by dropwise addition of acetyl chloride (5.68 ml, 79.92 mmol). The solution was allowed to warm to ambient temperature and stir for 1.5 hour. The reaction mixture was diluted with DCM, washed with water, sat. sodium hydrogen carbonate and brine. It was dried and the solvent was evaporated to give the title compound as a solid which was dried in vac oven overnight at 50° C. (17.46 g, 98%). NMR (400 MHz) 2.05 (s, 3H), 3.30 (dt, 4H, under $H_2O$ signal), 3.61 (m, 4H), 7.18 (t, 1H), 8.02 (d, 1H), 8.02 (dd, 1H); m/z 268.

Method 27

(3R,5S)-3,5-Dimethyl-1-(4-nitrophenyl)piperazine

1-Fluoro-4-nitrobenzene (10 g, 70.87 mmol) and (2R,6S)-2,6-dimethylpiperazine (17 g, 148.83 mmol) were heated in acetonitrile (25 ml) at 70° C. for 2 h. The solution was concentrated in vacuo, then the residue was partitioned between DCM and water+sat. sodium hydrogen carbonate. The organic extract was washed with water (4 times), brine, dried and concentrated to give the title compound as a yellow solid which was dried in vac oven overnight at 50° C. (16.13 g, 97%). NMR (400 MHz) 1.04 (d, 6H), 2.39 (m, 2H), 2.77 (m, 2H), 3.89 (dd, 2H), 7.02 (d, 2H), 8.03 (d, 2H); m/z 236.

Method 28

(2S,5R)-2,5-Dimethyl-1-(4-nitrophenyl)piperazine

1-Fluoro-4-nitrobenzene (6 g, 42.52 mmol) and (2R,5S)-2,5-dimethylpiperazine (21.9 g, 191.34 mmol) were heated in acetonitrile (20 ml) at 100° C. for 11 h. The solution was concentrated in vacuo, then the residue was partitioned between DCM and water+sat. sodium hydrogen carbonate. The organic extract was washed with water (4 times), brine, dried and concentrated. Chromatography on silica gel with MeOH: DCM (1:99 to 5:95) gave the title compound as an oil which solidified on standing overnight (8.32 g, 83%). NMR (400 MHz) 1.08 (d, 3H), 1.16 (d, 3H), 2.55 (dd, 1H), 3.18 (m, 2H), 3.34 (m, 2H), 3.95 (m, 1H), 6.91 (d, 2H), 8.03 (d, 2H); m/z 236.

Method 29

(2R,6S)-1-Acetyl-2,6-dimethyl-4-(4-nitrophenyl)piperazine

The title compound was prepared from (3R,5S)-3,5-dimethyl-1-(4-nitrophenyl)piperazine (Method 27, 16 g, 68.027 mmol) and acetyl chloride (8.22 ml, 115.65 mmol) by the procedure of Method 26. It was obtained as a solid which was dried in vac oven overnight at 50° C. (20.5 g, 109%, contaminated with solvent). NMR (400 MHz) 1.19 (brd, 6H), 2.08 (s, 3H), 3.21 (brd, 2H), 4.00 (d, 2H), 4.34 (v brs, 2H), 7.08 (d, 2H), 8.06 (d, 2H); m/z 278.

Method 30

(2R,5S)-1-Acetyl-2,5-dimethyl-4-(4-nitrophenyl)piperazine

The title compound was prepared from (2S,5R)-2,5-dimethyl-1-(4-nitrophenyl)piperazine (Method 28, 8.22 g, 34.95 mmol) and acetyl chloride (4.5 ml, 62.91) by the procedure of Method 26. It was obtained as an oil which solidified on standing overnight (11.39 g, >100%, contaminated with solvent) NMR (400 MHz) 1.13 (m, 6H), 3.07 (m, 1H), 3.33 (m, 1H), 3.68 (m, 1H), 4.25 (m, 2H), 4.69 (m, 1H), 7.00 (d, 2H), 8.05 (d, 2H); m/z 278.

Method 31

N-[4-(4-Acetylpiperazin-1-yl)-3-methylphenyl]guanidine bicarbonate salt

1-Acetyl-4-(2-methyl-4-nitrophenyl)piperazine (Method 25; 19.5 g, 74.06 mmol) in EtOH (400 ml) was hydrogenated over 10% Pd/carbon (2 g) at ambient temperature and pressure. The catalyst was filtered off, washed with EtOH (500 ml) and evaporation under reduced pressure to give the aniline as a beige/purple solid which was dried in vac oven overnight at 50° C. (17 g, 98%).

The aniline (15.5 g, 66.44 mmol) was stirred in dry 1,4-dioxane (120 ml) and EtOH (20 ml). 4N HCl in dioxane (19.93 ml, 79.73 mmol) was then added followed by cyanamide (4.5 g, 106.3 mmol). The reaction was heated at 100° C. for 2.5 hours under nitrogen, then extra cyanamide (838 mg, 19.93 mmol) was added and the reaction was heated for 5 further hours. After evaporation under reduced pressure, the solid-gum was triturated with ether and solvent re-evaporated. The solid-gum was dissolved in water (small volume), slowly added an excess of saturated sodium hydrogen carbonate solution with stirring. After 1 hour, the solid was collected by filtration and dried in vac oven overnight at 60° C. to give the title compound. (20.07 g, 90%). NMR (400 MHz) 2.04 (s, 3H), 2.22 (s, 3H), 2.75 (dt, 4H), 3.30 (brs, 2H, under $H_2O$ signal), 3.56 (m, 4H), 5.97 (v brs, 3H), 6.66 (dd, 1H), 6.70 (d, 1H), 6.90 (d, 1H); m/z 276.

Methods 32-33

The following compounds were prepared by the procedure of Method 31 using the appropriate nitro compound.

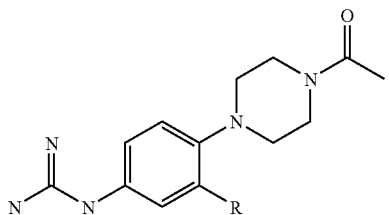

| Meth | R | NMR (400 MHz) | m/z | SM |
|---|---|---|---|---|
| 32[1] | Cl | 2.05 (s, 3H), 2.85 (dt, 4H), 3.29 (s, 1H, under $H_2O$ signal), 3.57 (m, 4H), 5.13 (s, 3H), 6.68 (dd, 1H), 6.79 (d, 1H), 6.98 (d, 1H) | 296–298 | Method 24 |
| 33[2] | F | 2.03 (s, 3H), 2.87 (dt, 4H), 3.29 (s, 2H, under $H_2O$ signal), 3.56 (m, 4H), 5.15 (brs, 3H), 6.53 (m, 2H), 6.87 (t, 1H) | 280 | Method 26 |

[1]Only 1.4 eq cyanamide used, no extra added and only 5.5 h heating. Preparation of free base: salt dissolved in small amount of water followed by addition of NaOH aq (2.5 M) (~22 ml). Precipitate formed filtered off to give a dark yellow solid which was dried in vac oven overnight at 50° C. (13.34 g, 100%).
[2]Extra cyanamide and HCl added and left heating overnight. (14.14 g, 68%).

Method 34

N-[4-((3R,5S)-4-Acetyl-3,5-dimethylpiperazin-1-yl)phenyl]guanidine

The title compound was prepared from (2R,6S)-1-acetyl-2,6-dimethyl-4-(4-nitrophenyl)piperazine (Method 29, 16.44 g, 66.5 mmol) and cyanamide (5.03 g, 119.7 mmol) by the procedure of Method 31 and heating overnight at 95° C. The bicarbonate salt was dried in vac oven at 60° C. overnight. As it was still wet, it was redissolved in MeOH and acetone and evaporation of solvent gave the title compound as a brown solid (18.6 g, 80%). NMR (400 MHz) 1.3 (brs, 6H), 2.05 (s, 3H), 2.70 (brd, 2H), 3.35 (m, 4H under $H_2O$ signal), 3.90-4.60 (v brs, 2H), 5.50-6.40 (v brs, 2H), 6.75 (d, 2H), 6.85 (d, 2H); m/z 290.

Method 35

N-[4-((2S,5R)-4-Acetyl-2,5-dimethylpiperazin-1-yl)phenyl]guanidine

The title compound was prepared from (2R,5S)-1-acetyl-2,5-dimethyl-4-(4-nitrophenyl)piperazine (Method 30, 6.5 g, 26.29 mmol) and cyanamide (2.43 g, 57.84 mmol) by the procedure of Method 31 and heating for 10 h at 95° C. The bicarbonate salt was dried in vac oven at 60° C. overnight. It was obtained as a solid (10.23 g, >100% contaminated with solvent). M/z 290.

Method 36

1-(4-Nitrophenyl)-azetidin-3-ol

A stirred mixture of 4-fluoro-nitrobenzene (12.70 g, 90 mM), 3-hydroxyazetidine hydrochloride (10.85 g, 99 mM) and anhydrous potassium carbonate in acetonitrile (250 ml) was heated under reflux for 6 hr. On cooling, some crystallisation occurred. The reaction mixture was diluted to 1.4 l with water and the crystallised material was filtered off, washed with water and dried. The title compound was a yellow crystalline solid (14.8 g, 85%). NMR: 3.73 (m, 2H), 4.25 (m, 2H), 4.60 (m, 1H), 5.77 (d, 1H), 6.43 (d, 2H), 8.00 (d, 2H); m/z 195.

Method 37

1-(4-Aminophenyl)azetidin-3-ol

A stirred solution of 1-(4-nitrophenyl)-azetidin-3-ol (Method 36; 15.15 g, 87 mM) in EtOH (250 ml) was hydrogenated over 10% Pd/C (1.5 g) for 18 hrs at atmospheric pressure. The reaction mixture was filtered and the filtrate was evaporated and triturated with ether giving the title compound as a grey crystalline solid. Much of the product had precipitated from the reaction mixture and been filtered off with catalyst. This was stirred with DMF (100 ml) for 15 mins and the catalyst filtered off. The filtrate was evaporated (Hi-Vac) and triturated with a little EtOH. The second crop of product was filtered off, washed with ether and dried. NMR: 3.35 (m+water, 2H), 3.90 (t, 2H), 4.32 (s, 2H), 4.45 (m, 1H), 5.41 (d, 1H), 6.20 (d, 2H), 6.45 (d, 2H); m/z 165.

Method 38 di-tert-Butyl((E)-{[4-(3-hydroxyazetidin-1-yl)phenyl]amino}methylylidene)biscarbamate To a solution of {[(Z)-tert-butoxycarbonylimino]-trifluoromethanesulfonyl-methyl}-carbamic acid tert-butyl ester (13.62 g, 34.8 mM) and triethylamine (4.9 ml, 34.8 mM) in dry DCM (183 ml), 1-(4-aminophenyl)azetidin-3-ol (Method 37; 6.0 g, 36.5 mM) was added. The solution was stirred at room temperature under nitrogen for 48 hours. The reaction mixture was diluted with more DCM and washed with water (twice), saturated sodium bicarbonate solution (twice), water and saturated sodium chloride. The solution was then dried with anhydrous sodium sulphate, filtered and evaporated. The crude product was triturated with ether/isohexane (2:1), filtered washed with the same solvent and dried to give the title compound as a yellow solid (11.77 g, 83%). NMR 1.4 (s, 9H), 1.5 (s, 9H), 3.47 (t, 1H), 4.02 (t, 2H), 4.5 (m, 1H), 5.55 (d, 1H), 6.38 (d, 2H), 7.23 (d, 2H), 9.75 (s, 1H), 11.46 (m, 1H); m/z 407.

Method 39

N-[4-(3-Hydroxyazetidin-1-yl)phenyl]guanidine bicarbonate salt

A solution of di-tert-butyl((E)-{[4-(3-hydroxyazetidin-1-yl)phenyl]amino}methylylidene)biscarbamate (Method 38; 250 mg, 0.62 mM) in TFA (4.5 ml) and water (0.52 ml) was stirred at room temperature overnight. The water and excess TFA were removed in vacuo. The crude salt was dissolved in MeOH (5 ml) and macroporous polystyrene carbonate resin (0.49 g of capacity 3.0 m.equ per g) solid supported reagent was added and the mixture was gently stirred at room temperature for 4 hours. The resin was filtered off and washed with MeOH and the filtrate evaporated to give the title compound as a brown glass (45 mg, 77%). NMR 3.47 (t, 2H), 4.05 (t, 2H), 4.54 (m, 1H), 6.42 (d, 2H), 7.0 (d, 2H); m/z 207.

Method 40 tert-Butyl[(3R)-1-(4-nitrophenyl)pyrrolidin-3-yl]carbamate tert-Butyl(3R)-pyrrolidin-3-ylcarbamate (4.54 g, 24.4 mmol), 4-fluoronitrobenzene (3.78 g, 24 mmol) and potassium carbonate (3.54 g 25.6 mmol) in acetonitrile (70 ml) were heated under reflux for 18 hours. After evaporation under reduced pressure, the mixture was dissolved in DCM (200 ml), and washed with water (100 ml) and saturated sodium chloride solution (25 ml). The solution was dried and filtered. After evaporation under reduced pressure, chromatography on silica gel eluting with DCM gave the title compound (7.19 g, 97%). NMR: 1.39 (s, 9H), 1.87-1.98 (m, 1H), 2.09-2.21 (m, 1H), 3.15-3.23 (m, 1H), 3.32-3.44 (m, 1H), 3.45-3.51 (m, 1H), 3.53-3.61 (m, 1H), 4.09-4.21 (m, 1H), 6.57 (d, 2H), 7.21 (s, 1H), 8.01 (d, 2H); m/z ($MH^+$—$C_4H_8$) 252.

Method 41

(3R)-1-(4-Nitrophenyl)pyrrolidin-3-amine trifluoroacetate salt tert-Butyl[(3R)-1-(4-nitrophenyl)pyrrolidin-3-yl]carbamate (Method 40; 1.0 g, 3.26 mmol) in DCM (15 ml) was reacted with TFA (7.5 ml) at room temperature for 18 hours. Pouring into cold ether (200 ml) gave on filtration the title compound (0.97 g, 93%). NMR: 2.03-2.17 (m, 1H), 2.22-2.44 (m, 1H), 3.40-3.60 (m, 3H), 3.68-3.74 (m, 1H), 3.95-4.08 (m, 1H), 6.66 (d, 2H), 8.08 (d, 2H), 8.14 (s, 2H).

Method 42

N-[(3R)-1-(4-Nitrophenyl)pyrrolidin-3-yl]acetamide (3R)-1-(4-Nitrophenyl)pyrrolidin-3-amine trifluoroacetate salt (Method 41; 0.96 g, 3 mmol) and sodium acetate (0.245 g, 3 mmol) in acetic acid (10 ml) were reacted with acetic anhydride (0.57 ml, 6 mmol) for 18 hours at room temperature. After filtration and washing with ether gave the title compound as a yellow solid (0.63 g, 84%). NMR: 1.79 (s, 3H), 1.85-1.98 (m, 1H), 2.09-2.23 (m, 1H), 3.19-3.30 (m, 1H), 3.39-3.52 (m, 2H), 3.55-3.67 (m, 1H), 4.30-4.43 (m, 1H), 6.60 (d, 2H), 8.04 (d, 2H), 8.15 (d, 1H); m/z 250.

Method 43

N-[(3R)-1-(4-Aminophenyl)pyrrolidin-3-yl]acetamide mono hydrochloride

N-[(3R)-1-(4-nitrophenyl)pyrrolidin-3-yl]acetamide (Method 42; 4.5 g, 18 mmol) hydrogenated over 10% palladium/carbon at room temperature and 1 atmosphere pressure in absolute alcohol (200 ml). After filtration of the catalyst and evaporation at reduced pressure gave N-[(3R)-1-(4-aminophenyl)pyrrolidin-3-yl]acetamide as a red oil (3.75 g, 95%). NMR (CDCl$_3$): 1.97 (s, 3H), 1.89-2.03 (m, 1H), 2.22-2.34 (m, 1H), 2.54 (s, 2H), 3.06-3.27 (m, 2H), 3.34-3.48 (m, 2H), 4.52-4.68 (m, 1H), 5.79 (brs, 1H), 6.48 (d, 2H), 6.69 (d, 2H); m/z 220. Treatment with 4M hydrogen chloride in 1,4-dioxane gave the title compound (4.21 g, 96%). LCMS: m/z 220.

Method 44 di-tert-Butyl[(E)-({4-[(3R)-3-(acetylamino)pyrrolidin-1-yl]phenyl}amino)methylylidene]biscarbamate N-[(3R)-1-(4-aminophenyl)pyrrolidin-3-yl]acetamide mono hydrochloride (Method 43; 2.47 g, 9.67 mmol) and Hunigs base (2.02 ml, 1.16 mmol) were reacted with di-tert-butyl [(Z)-1H-pyrazol-1-ylmethylylidene]biscarbamate (2.95 g, 9.5 mmol) in THF (50 ml) at room temperature for 72 hours. After evaporation under reduced pressure, chromatography on silica gel with EtOAc/isohexane (50:50 to 100) gave the title compound as a yellow oil (3.06 g, 69%). NMR: 1.39 (s, 9H), 1.52 (s, 9H), 1.81 (s, 3H), 1.82-1.93 (m, 1H), 2.11-2.24 (m, 1H), 3.00-3.08 (m, 1H), 3.21-3.51 (m, 3H), 4.29-4.40 (m, 1H), 6.50 (d, 2H), 7.29 (d, 2H), 8.12 (d, 1H), 9.74 (s, 1H), 11.49 (s, 1H); m/z 462.

Method 45

4-((3R)-Acetamidopyrrolidin-1-yl)phenyl guanidine carbonate

[(E)-({4-[(3R)-3-(acetylamino)pyrrolidin-1-yl]phenyl}amino)methylylidene]biscarbamate (Method 44; 3.06 g, 6.6 mmol), was reacted with TFA (20 ml) in DCM (100 ml) at room temperature under nitrogen for 18 hours. After evaporation under reduced pressure, the residue was dissolved in MeOH (40 ml) and treated with macroporous polystyrene carbonate resin (0.49 g of capacity 3.0 m.equ per g) (6 g), and was stirred for 4 hours. The mixture was filtered and washed with MeOH. Evaporation under reduced pressure gave the title compound as a grey solid (1.25 g, 65%). NMR: 1.80-1.94 (m, 1H), 1.83 (s, 3H), 2.09-2.22 (m, 1H), 2.96-3.09 (m, 1H), 3.19-3.29 (m, 1H), 3.30-3.39 (m, 1H), 3.40-3.52 (m, 1H), 4.28-4.41 (m, 1H), 6.52 (d, 2H), 6.91 (d, 2H), 7.32 (brs, 4H), 8.13 (d, 1H); m/z 262.

Method 46 tert-Butyl[(3S)-1-(4-nitrophenyl)pyrrolidin-3-yl]carbamate

The title compound was prepared by the procedure of Method 40 starting from tert-butyl (3S)-pyrrolidin-3-ylcarbamate (6.11 g, 74%). NMR: 1.36 (s, 9H), 1.83-1.98 (m, 1H), 2.08-2.20 (m, 1H), 3.12-3.24 (m, 1H), 3.31-3.51 (m, 2H), 3.52-3.65 (m, 1H), 4.09-4.23 (m, 1H), 6.58 (d, 2H), 7.20 (s, 1H), 8.01 (d, 2H); m/z 198 (MH$^+$—C$_4$H$_8$).

Method 47

(3S)-1-(4-Nitrophenyl)pyrrolidin-3-amine trifluoroacetate salt

The title compound was prepared by the procedure of Method 41 starting from tert-butyl[(3S)-1-(4-nitrophenyl)pyrrolidin-3-yl]carbamate (Method 46) (6.6 g, 100%). NMR: 2.03-2.19 (m, 1H), 2.20-2.40 (m, 1H), 3.25-3.75 (m, 3H), 3.94-4.04 (m, 1H), 4.38 (brs, 2H), 6.64 (d, 2H), 8.08 (d, 2H), 8.24 (s, 3H): m/z 208.

Method 48

N-[(3S)-1-(4-Nitrophenyl)pyrrolidin-3-yl]acetamide

The title compound was prepared by the procedure of Method 42 starting from (3S)-1-(4-nitrophenyl)pyrrolidin-3-amine trifluoroacetate salt (Method 47) (4.2 g, 93%). NMR: 1.80 (s, 3H), 1.86-1.98 (m, 1H), 2.11-2.24 (m, 1H), 3.15-3.28 (m, 1H), 3.37-3.55 (m, 2H), 3.64-3.70 (m, 1H), 4.32-4.44 (m, 1H), 6.61 (d, 2H), 8.04 (d, 2H), 8.15 (d, 1H): m/z 250.

Method 49

N-[(3S)-1-(4-Aminophenyl)pyrrolidin-3-yl]acetamide

The title compound was prepared by the procedure of Method 43 starting from N-[(3S)-1-(4-nitrophenyl)pyrrolidin-3-yl]acetamide (Method 48). NMR: 1.79 (s, 3H), 1.69-1.88 (m, 1H), 2.07-2.20 (m, 1H), 2.82-2.93 (m, 1H), 3.01-3.14 (m, 1H), 3.16-3.38 (m, 2H), 4.25-4.36 (m, 1H), 6.31 (d, 2H), 6.51 (d, 2H), 8.08 (d, 1H)+EtOH.

Method 50 di-tert-Butyl[(E)-({4-[(3R)-3-(acetylamino)pyrrolidin-1-yl]phenyl}amino)methylylidene]biscarbamate The title compound was prepared by the procedure of Method 44 starting from N-[(3S)-1-(4-aminophenyl)pyrrolidin-3-yl]acetamide (Method 49) (4.16 g, 45%). NMR: 1.31-1.56 (brs, 18H), 1.80 (s, 3H), 1.82-1.93 (m, 1H), 2.07-2.21 (m, 1H), 3.00-3.08 (m, 1H), 3.19-3.40 (m, 2H), 3.43-3.49 (m, 1H), 4.30-4.41 (m, 1H), 6.50 (d, 2H), 7.26 (d, 2H), 7.57 (s, 2H), 8.10 (d, 1H); m/z 462.

Method 51

4-((3S)-Acetamidopyrrolidin-1-yl)phenyl guanidine carbonate

The title compound was prepared by the procedure of Method 45 starting from di-tert-butyl[(E)-({4-[(3R)-3-(acetylamino)pyrrolidin-1-yl]phenyl}amino)methylylidene]biscarbamate (Method 50) (2.26 g, 86%). NMR: 1.79 (s, 3H), 1.79-1.89 (m, 1H), 2.09-2.21 (m, 1H), 2.97-3.02 (m, 1H), 3.16-3.23 (m, 1H), 3.27-3.44 (m, 3H), 4.26-4.37 (m, 1H), 6.20-6.25 (m, 1H), 6.46 (d, 2H), 6.79 (d, 2H), 7.57 (d, 2H), 8.09 (d, 1H); m/z 262.

Method 52

(R)-1-(4-Nitro-phenyl)-pyrrolidine-2-carboxylic acid dimethylamide

4-Fluoronitrobenzene (0.47 g, 3.34 mmol), potassium carbonate (1.39, 10 mmol) and (R)-pyrrolidine-2-carboxylic acid dimethylamide (0.50, 3.52 mmol) were pre-mixed in acetonitrile (40 ml) and heated at reflux for 36 hours. The reaction was quenched with saturated ammonium chloride (40 ml), extracted with DCM (2×100 ml), dried and solvent removed in vacuo to yield the title compound as a yellow solid. Ether was added and the solid was stirred, filtered and dried (0.85 g, 96%). M/z 264.

Method 53

(S)-1-(4-Amino-phenyl)-pyrrolidine-2-carboxylic acid dimethylamide (R)-1-(4-Nitro-phenyl)-pyrrolidine-2-carboxylic acid dimethylamide (Method 52; 0.85 g) was dissolved in MeOH (50 ml), to this was added ammonium formate (1.0 g, 16 mmol) and palladium (0.1 g). The reaction was heated at reflux for 60 minutes (reaction decolourised). MeOH was removed in vacuo and saturated ammonium chloride (50 ml) was added. The system was extracted with DCM (2×100 ml), dried and solvent was removed in vacuo to yield the title compound as a brown gum (0.67 g, 87%). The product rapidly turned black on exposure to air. The product was used immediately without any purification.

Method 54

(S)-1-(4-Guanidino-phenyl)-pyrrolidine-2-carboxylic acid dimethylamide

To (S)-1-(4-Amino-phenyl)-pyrrolidine-2-carboxylic acid dimethylamide (Method 53; 0.67 g) was added acetonitrile (20 ml) and EtOH (2 ml). HCl in dioxane (0.86 ml, 3.48 mmol) was added and the reaction was stirred for 10 minutes, HCl salt precipitated. Cyanamide (0.2 g, 4.9 mmol) was added and the reaction was heated at reflux over the weekend. The black reaction was filtered and the black HCl salt was dissolved in water (5 ml) and basified with $NaHCO_3$ (20 ml) solution. No solid was observed; the aqueous was further basified to pH 14 with KOH, extracted with DCM (2×100 ml), dried and solvent removed in vacuo to yield the title compound as a black gum (0.50 g, 63%). M/z 276.

Method 55

(R)-1-(4-Nitro-phenyl)-pyrrolidine-2-carboxylic acid

Proline (3.5 g, 30.4 mmol), 4-iodonitrobenzene (7.2 g, 28.9 mmol), $Pd(PPh_3)_4$ (1.7 g, 5 mol %), copper iodide (0.3 g, 5 mol %), benzyltriethylammonium chloride (11.9 g, 52 mmol), triethylamine (8.3 ml, 60 mmol) and potassium carbonate (4.2 g, 30 mmol) were pre-mixed in DMF (60 ml)/water (6 ml). The reaction was heated at 80° C. for 8 hours. The DMF was removed in vacuo and the remaining black gum was dissolved in DCM, acidified with 2.0 N HCl (50 ml), extracted with DCM (3×100 ml), dried and solvent removed in vacuo to yield a black tar. The tar was dissolved in a minimum amount of DCM (7 ml) and loaded onto a 50 g silica column, the system was eluted with 20% EtOAc/isohexane, then 60% EtOAc/iso-hexane and finally 100% EtOAc. The title compound was obtained as an orange gum. NMR (299.954 MHz, $CDCl_3$) 8.13 (d, 2H), 6.52 (d, 2H), 4.41 (d, 1H), 3.66 (t, 1H), 3.49 (q, 1H), 2.47-2.29 (m, 2H), 2.25-2.12 (m, 2H); m/z 237.

Method 56

(R)-1-(4-Nitro-phenyl)-pyrrolidine-2-carboxylic acid methylamide

To (R)-1-(4-Nitro-phenyl)-pyrrolidine-2-carboxylic acid (Method 55; 1.8 g, 7.6 mmol) in DCM (50 ml) was added HATU (3.2 g, 8.4 mmol) and DIPEA (2.0 ml, 11.4 mmol). The reaction was stirred for 10 minutes before the addition of methylamine (2.0 N in THF, 5.0 ml, 15 mmol); the reaction was stirred for 1 hour before being quenched with water (50 ml). The reaction was extracted with DCM (3×100 ml), dried and solvent removed in vacuo to yield a yellow gum. Purification was achieved via column chromatography eluting with 20% EtOAc/isohexane, 60% EtOAc/isohexane and finally 100% EtOAc. The title compound was obtained as an orange gum; (1.4 g, 74%). NMR (299.954 MHz, $CDCl_3$) 8.10 (d, 2H), 6.56 (d, 2H), 6.24 (s, 1H), 4.20 (t, 1H), 3.75 (t, 1H), 3.40 (q, 1H), 2.80 (d, 3H), 2.36-2.29 (m, 2H), 2.13-2.05 (m, 2H); m/z 250.

Method 57

(R)-1-(4-Amino-phenyl)-pyrrolidine-2-carboxylic acid methylamide (R)-1-(4-Nitro-phenyl)-pyrrolidine-2-carboxylic acid methylamide (Method 56; 1.2 g, 4.8 mmol) was dissolved in MeOH (50 ml), to this was added ammonium formate (1.5 g, 24 mmol) and palladium (0.1 g). The reaction was heated at reflux for 60 minutes; reaction decolourised. MeOH was removed in vacuo and saturated ammonium chloride (50 ml) was added, the system was extracted with DCM (2×100 ml), dried and solvent removed in vacuo to yield the title compound as a brown gum (1.0 g, 95%). Product rapidly turned black on exposure to air. The product was used immediately without any purification.

Method 58

1-[4-({(E)-[(tert-Butoxycarbonyl)amino][(tert-butoxycarbonyl)imino]methyl}amino)phenyl]-N-methyl-D-prolinamide To (R)-1-(4-amino-phenyl)-pyrrolidine-2-carboxylic acid methylamide (Method 57; 1.0 g, 4.5 mmol) in DCM (60 ml) was added di-tert-butyl[(Z)-1H-pyrazol-1-ylmethylylidene]biscarbamate (1.7 g, 5.5 mmol) in one portion. The reaction was stirred overnight before removal of the solvent in vacuo. The residue was purified via column chromatography eluting with 20% EtOAc/isohexane, 50% EtOAc/iso-hexne and finally 100% EtOAc. The title compound was obtained as a white foam (1.9 g, 91%).

Method 59

(R)-1-(4-Guanidino-phenyl)-pyrrolidine-2-carboxylic acid methylamide

To 1-[4-({(E)-[(tert-butoxycarbonyl)amino][(tert-butoxycarbonyl)imino]methyl}amino)phenyl]-N-methyl-D-prolinamide (Method 58; 1.9 g) was added DCM (60 ml) and TFA (20 ml). The reaction was stirred for 4 hours before removal of the solvent in vacuo. The reaction was basified with 2.0N KOH (20 ml) and extracted with DCM (2×50 ml). Product failed to extract in to DCM, the aqueous was reduced down to 90% of the initial volume and re-extracted with DCM (3×200 ml), dried and solvent removed in vacuo to yield the title compound as a brown solid (0.84 g, 78%). NMR (299.955 MHz) 7.79 (q, 1H), 7.57 (s, 1H), 7.18 (s, 2H), 7.03 (d, 2H), 6.48 (d, 2H), 3.91 (d, 1H), 3.58-3.54 (m, 1H), 3.17 (q, 1H), 2.56 (d, 3H), 2.19-2.09 (m, 2H), 2.01-1.89 (m, 2H); m/z 261.

Method 60

(R)-1-(4-Nitro-phenyl)-pyrrolidine-2-carboxylic acid cyclopropylamide

To (R)-1-(4-nitro-phenyl)-pyrrolidine-2-carboxylic acid (Method 55; 1.8 g, 7.6 mmol) in DCM (50 ml) was added HATU (3.2 g, 8.4 mmol) and DIPEA (2.0 ml, 11.4 mmol). The reaction was stirred for 10 minutes before the addition of methylamine (0.84 g, 15 mmol); the reaction was stirred for 1 hour and then quenched with water (50 ml). The reaction was extracted with DCM (3×100 ml), dried and solvent removed in vacuo to yield a yellow gum. Purification was achieved via column chromatography eluting with 20% EtOAc/isohexane, 60% EtOAc/isohexane and finally 100% EtOAc. The title compound was obtained as a yellow solid (1.4 g, 74%). NMR (299.954 MHz, CDCl$_3$) δ 8.13 (d, 2H), 6.55 (d, 2H), 6.06 (s, 1H), 4.14 (t, 1H), 3.70 (t, 1H), 3.38 (q, 1H), 2.75-2.66 (m, 1H), 2.36-2.29 (m, 2H), 2.17-1.95 (m, 2H), 0.82-0.73 (m, 2H), 0.46-0.35 (m, 2H); m/z 276.

Method 61

(R)-1-(4-Amino-phenyl)-pyrrolidine-2-carboxylic acid cyclopropylamide (R)-1-(4-Nitro-phenyl)-pyrrolidine-2-carboxylic acid cyclopropylamide (Method 60; 142 g, 5.1 mmol) was dissolved in MeOH (50 ml), to this was added ammonium formate (1.6 g, 26 mmol) and palladium (0.1 g). The reaction was heated at reflux for 60 minutes; reaction decolourised. MeOH was removed in vacuo and saturated ammonium chloride (50 ml) was added, the system was extracted with DCM (2×100 ml), dried and solvent removed in vacuo to yield the title compound as a brown gum (1.20 g, 96%). Product rapidly turned black on exposure to air. The product was used immediately without any purification; m/z 246.

Method 62

1-[4-({(E)-[(tert-Butoxycarbonyl)amino][(tert-butoxycarbonyl)imino]methyl}amino)phenyl]-N-cyclopropyl-D-prolinamide (R)-1-(4-Amino-phenyl)-pyrrolidine-2-carboxylic acid cyclopropylamide (Method 61; 1.2 g, 4.9 mmol) in DCM (60 ml) was added di-tert-butyl[(Z)-1H-pyrazol-1-ylmethylylidene]biscarbamate (1.9 g, 6.1 mmol) in one portion. The reaction was stirred overnight before removal of the solvent in vacuo. The residue was purified via column chromatography eluting with 20% ethylactetate/isohexane, 50% EtOAc/isohexane and finally 100% EtOAc. The title compound was obtained as a white foam (2.0 g, 81%). NMR (299.954 MHz, CDCl$_3$) 11.63 (s, 1H), 10.09 (s, 1H), 7.60 (s, 1H), 7.40 (d, 2H), 6.45 (m, 3H), 3.92 (t, 1H), 3.59 (t, 1H), 3.19 (q, 1H), 2.69 (m, 1H), 2.29-2.22 (m, 2H), 2.03-1.84 (m, 2H), 1.53 (s, 9H), 1.49 (s, 9H), 0.80-0.68 (m, 2H), 0.44-0.32 (m, 2H); m/z 488.

Method 63

(R)-1-(4-Guanidino-phenyl)-pyrrolidine-2-carboxylic acid cyclopropylamide

To 1-[4-({(E)-[(tert-butoxycarbonyl)amino][(tert-butoxycarbonyl)imino]methyl}amino)phenyl]-N-cyclopropyl-D-prolinamide (Method 62; 2.0 g) was added DCM (60 ml) and TFA (20 ml). The reaction stirred for 4 hours before removal of the solvent in vacuo. To the gum was added DCM (75 ml) and macroporous polystyrene carbonate resin (0.49 g of capacity 3.0 m.equ per g) solid supported reagent (20 g), the reaction was slowly stirred overnight. The reaction was filtered and the solvent removed in vacuo to yield very little product. A white solid was present in the filter cup, this was dissolved in MeOH, the resin was also added to the MeOH, the system was stirred for 10 minutes before being filtered, the solvent was removed in vacuo to yield the title compound as a white solid (0.90 g, 75%). NMR (299.954 MHz, CDCl$_3$) δ 7.26 (s, 3H), 6.85 (d, 2H), 6.49 (d, 2H), 3.93 (d, 1H), 3.62-3.60 (m, 1H), 3.17 (q, 1H), 2.70-2.62 (m, 1H), 2.32-2.14 (m, 2H), 2.00-1.92 (m, 2H), 0.76-0.63 (m, 2H), 0.42 (q, 2H); m/z 287.

Method 64 tert-Butyl[(3R)-1-(2-fluoro-4-nitrophenyl)pyrrolidin-3-yl]carbamate

The title compound was prepared by an analogous route to Method 40 starting from tert-butyl(3R)-pyrrolidin-3-ylcarbamate (5.40 g, 74%). NMR: 1.36 (s, 9H), 1.81-1.94 (m, 1H), 2.02-2.16 (m, 1H), 3.30-3.42 (m, 1H), 3.48-3.59 (m, 1H), 3.69-3.79 (m, H), 4.02-4.17 (m, 1H), 6.72 (t, 1H), 7.18 (brs, 1H), 7.92 (d, 2H); m/z 270 (MH$^+$—C$_4$H$_8$).

Method 65

(3R)-1-(2-Fluoro-4-nitrophenyl)pyrrolidin-3-amine trifluoroacetate salt

The title compound was prepared by an analogous route to Method 41 starting from tert-butyl[(3R)-1-(2-fluoro-4-nitrophenyl)pyrrolidin-3-yl]carbamate (Method 64) (5.12 g, 94%). NMR: 2.01-2.14 (m, 1H), 2.20-2.36 (m, 1H), 3.53-4.01 (m, 4H), 6.80 (t, 1H), 7.96 (d, 2H), 8.18 (s, 3H); m/z 226.

Method 66

N-[(3R)-1-(2-Fluoro-4-nitrophenyl)pyrrolidin-3-yl]acetamide

The title compound was prepared by an analogous route to Method 42 starting from (3R)-1-(2-fluoro-4-nitrophenyl)pyrrolidin-3-amine trifluoroacetate salt (Method 65) (3.78 g, 90%). NMR: 1.80 (s, 3H), 1.85-1.94 (m, 1H), 2.05-2.19 (m, 1H), 3.32-3.42 (m, 1H), 3.51-3.71 (m, 2H), 3.73-3.82 (m, H), 4.28-4.36 (m, 1H), 6.72 (t, 1H), 7.38-7.92 (n, 2H), 8.11 (d, 1H); m/z 268.

Method 67

N-[(3R)-1-(4-Amino-2-fluorophenyl)pyrrolidin-3-yl]acetamide

The title compound was prepared by an analogous route to Method 43 starting from N-[(3R)-1-(2-fluoro-4-nitrophenyl)pyrrolidin-3-yl]acetamide (Method 66) (2.62 g, 76%). NMR: 1.64-1.76 (m, 1H), 1.79 (s, 3H), 2.02-2.16 (m, 1H), 2.87-2.92 (m, H), 2.99-3.05 (m, 1H), 3.16-3.32 (m, 2H), 4.16-4.28 (m, 1H), 4.68 (brs, 2H), 6.22-6.33 (m, 1H), 6.35 (d, 2H), 6.73 (d, 1H), 8.02 (d, H); m/z 238.

Method 68 di-tert-Butyl[(E)-({2-fluoro-4-[(3R)-3-(acetylamino)pyrrolidin-1-yl]phenyl}amino)methylylidene]biscarbamate The title compound was prepared by an analogous route to Method 44 starting from N-[(3R)-1-(4-amino-2-fluorophenyl)pyrrolidin-3-yl]acetamide (Method 67). NMR: 1.39 (brs, 9H), 1.46 (brs, 9H), 1.79 (s, 3H), 1.70-1.87 (m, 1H), 2.02-2.16 (m, 1H), 3.09-3.16 (m, 1H), 3.22-3.34 (m, 1H), 3.38-3.47 (m, 1H), 3.51-3.56 (m, 1H), 4.24-4.32 (m, 1H), 6.68 (t, 1H), 7.08 (d, 1H), 7.41 (d, 1H), 8.08 (d, 1H), 8.89 (brs, 1H), 9.83 (brs, 1H), 11.41 (brs, 1H); m/z 480.

Method 69

2-Fluoro-4-((3R)-acetamidopyrrolidin-1-yl)phenyl guanidine carbonate

The title compound was prepared by an analogous route to Method 45 starting from di-tert-butyl[(E)-({2-fluoro-4-[(3R)-3-(acetylamino)pyrrolidin-1-yl]phenyl}amino)methylylidene]biscarbamate (Method 68) (2.43 g, 86%). NMR: 1.75-1.86 (m, 1H), 1.80 (s, 3H), 2.06-2.18 (m, 1H), 3.21-3.38 (m, 2H), 3.50-3.60 (m, 1H), 4.21-4.34 (m, 1H), 6.72 (t, 1H), 6.89 (d, 1H), 7.00 (d, 1H), 7.29 (brs, 3H), 8.08 (d, 1H), 9.50 (s, 1H).

Method 70

4-((3R)-Acetamidopyrrolidin-1-yl)phenyl guanidine trifluoroacetate salt

N-[(3R)-1-(4-aminophenyl)pyrrolidin-3-yl]acetamide mono hydrochloride (Method 44, 3.31 g, 15 mmol), di-tert-butyl[(Z)-1H-pyrazol-1-ylmethylylidene]biscarbamate (5.91 g, 15 mmol) and triethylamine (4.17 ml, 30 mmol) in DCM (50 ml) were heated at 40° C. for 18 hours. After evaporation under reduced pressure, chromatography on silica gel with ethyl acetate/isohexane (50:50 to 100) gave di-tert-butyl[(E)-({4-[(3R)-3-(acetylamino)pyrrolidin-1-yl]phenyl}amino)methylylidene]biscarbamate, which was dissolved in DCM (80 ml) and treated with TFA (15 ml) at ambient temperature for 18 hours under nitrogen. After evaporation under reduced pressure, the residue was dissolved in MeOH (20 ml) and diluted with ether. The title compound was collected by filtration as an off white solid (1.79 g, 30% over two steps). NMR: 1.80 (s, 3H), 1.81-1.93 (m, 1H), 2.10-2.27 (m, 1H), 2.99-3.06 (m, 1H), 3.19-3.51 (m, 3H), 4.27-4.39 (m, 1H), 6.52 (d, 2H), 7.03 (d, 2H), 7.16 (s, 3H), 8.10 (d, 1H), 9.36 (s, 1H).

Example 164

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

The invention claimed is:
1. A compound of formula (I):

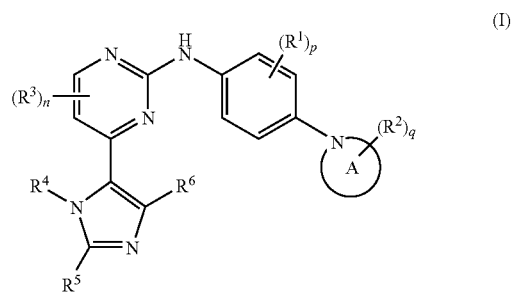

wherein:
Ring A is a nitrogen linked 4-7 membered saturated ring which optionally contains an additional nitrogen, oxygen or sulphur atom; wherein if Ring A contains an additional nitrogen atom that nitrogen may be optionally substituted by $R^7$;

$R^1$ is halo, nitro, cyano, hydroxy, amino, carboxy, carbamoyl, mercapto, $C_{1-6}$alkyl, $C_{1-6}$alkoxy, $C_{2-6}$alkenyl or $C_{2-6}$alkynyl;

p is 0-4; wherein the values of $R^1$ may be the same or different;

$R^2$ is selected from halo, nitro, cyano, hydroxy, trifluoromethoxy, amino, carboxy, carbamoyl, mercapto, azido, sulphamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, carbocyclyl-$R^{34}$—, heterocyclyl-$R^{35}$—, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$sulphamoyl; wherein $R^2$ independently may be optionally substituted on carbon by one or more $R^8$; or $R^2$ is —$NHR^9$, —$NR^{10}R^{11}$ or —O—$R^{12}$;

q is 0-2; wherein the values of $R^2$ maybe the same or different;

$R^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N—($C_{1-3}$alkyl)amino, N,N—($C_{1-3}$alkyl)$_2$amino, $C_{1-3}$alkanoylamino, N—($C_{1-3}$alkyl)carbamoyl, N,N—($C_{1-3}$alkyl)$_2$carbamoyl, $C_{1-3}$alkylS(O)$_a$ wherein a is 0 to 2, N—($C_{1-3}$alkyl)sulphamoyl or N,N—($C_{1-3}$alkyl)$_2$sulphamoyl; wherein $R^3$ may be independently optionally substituted on carbon by one or more $R^{13}$;

n is 0 to 2, wherein the values of $R^3$ may be the same or different;

$R^4$ is hydrogen, $C_{1-6}$alkyl, $C_{2-6}$alkenyl, $C_{2-6}$alkynyl, carbocyclyl or a carbon-linked heterocyclyl; wherein $R^4$ may be optionally substituted on carbon by one or more $R^{14}$; and wherein if said heterocyclyl contains an —NH— moiety that nitrogen may be optionally substituted by a group selected from $R^{15}$;

$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, $C_{3-8}$cycloalkyl or a 4-7 membered saturated heterocyclic group; wherein $R^5$ and $R^6$ independently of each other may be optionally substituted on carbon by one or more $R^{16}$; and wherein if a 4-7 membered saturated heterocyclic group contains an —NH— moiety that nitrogen may be optionally substituted by a group selected from $R^{17}$;

$R^7$, $R^9$, $R^{10}$, $R^{11}$ and $R^{12}$ are independently selected from $C_{1-6}$alkyl, $C_{1-6}$alkanoyl, $C_{1-6}$alkylsulphonyl, $C_{2-6}$alkenylsulphonyl, $C_{2-6}$alkynylsulphonyl, $C_{1-6}$alkoxycarbonyl, carbamoyl, N—($C_{1-6}$alkyl)carbamoyl, N,N—($C_{1-6}$alkyl)carbamoyl, carbocyclyl, heterocyclyl, carbocyclyl-$R^{18}$— or heterocyclyl-$R^{19}$—; wherein $R^7$, $R^9$, $R^{10}$, $R^{11}$ and $R^{12}$ may be independently optionally substituted on carbon by a group selected from $R^{20}$; and wherein if said heterocyclyl contains an —NH— moiety that nitrogen may be optionally substituted by $R^{21}$;

$R^{14}$ and $R^{20}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkoxy$C_{1-6}$alkoxy, $C_{1-6}$alkoxy$C_{1-6}$alkoxy$C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl, heterocyclyl, carbocyclyl $C_{1-6}$alkyl-$R^{22}$, heterocyclyl$C_{1-6}$alkyl-$R^{23}$—, carbocyclyl-$R^{24}$— or heterocyclyl-$R^{25}$—; wherein $R^{14}$ and $R^{20}$ may be independently optionally substituted on carbon by one or more $R^{26}$; and wherein if said heterocyclyl contains an —NH— moiety that nitrogen may be optionally substituted by a group selected from $R^{27}$;

$R^{18}$, $R^{19}$, $R^{22}$, $R^{23}$, $R^{24}$, $R^{25}$, $R^{34}$ or $R^{35}$ are independently selected from —O—, —N($R^{28}$)—, —C(O)—, —N($R^{29}$)C(O)—, —C(O)N($R^{30}$)—, —S(O)$_s$—, —SO$_2$N($R^{31}$)— or —N($R^{32}$)SO$_2$—; wherein $R^{28}$, $R^{29}$, $R^{30}$, $R^{31}$ and $R^{32}$ are independently selected from hydrogen or $C_{1-6}$alkyl and s is 0-2;

$R^{15}$, $R^{17}$, $R^{21}$ and $R^{27}$ and are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^{15}$, $R^{17}$, $R^{21}$ and $R^{27}$ independently of each other may be optionally substituted on carbon by on or more $R^{33}$; and $R^8$, $R^{13}$, $R^{16}$, $R^{26}$ and $R^{33}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

2. A compound of formula (I) as claimed in claim 1 wherein:

Ring A is a nitrogen linked 4-7 membered saturated ring which optionally contains an additional nitrogen or oxygen atom; wherein if Ring A contains an additional nitrogen atom that nitrogen may be optionally substituted by $R^7$; wherein $R^7$ is selected from $C_{1-6}$alkanoyl, $C_{1-6}$alkylsulphonyl, $C_{2-6}$alkenylsulphonyl, carbocyclyl-$R^{18}$— or heterocyclyl-$R^{19}$—; wherein $R^7$ may be independently optionally substituted on carbon by a group selected from $R^{20}$; and wherein if said heterocyclyl contains an —NH-moiety that nitrogen may be optionally substituted by $R^{21}$;

$R^{18}$ and $R^{19}$ are —C(O)—;

$R^{20}$ is selected from halo, cyano, hydroxy, $C_{1-6}$alkoxy, $C_{2-6}$alkynyloxy, $C_{1-6}$alkanoyloxy, N,N—($C_{1-6}$alkyl)$_2$ amino, $C_{1-6}$alkylS(O)$_a$ wherein a is 2 or heterocyclyl; wherein $R^{20}$ may be optionally substituted on carbon by one or more $R^{26}$;

$R^{21}$ is $C_{1-6}$alkyl; and $R^{26}$ is hydroxy;

or a pharmaceutically acceptable salt thereof.

3. A compound of formula (I) as claimed in claim 1 wherein $R^1$ is halo or $C_{1-6}$alkyl or a pharmaceutically acceptable salt thereof.

4. A compound of formula (I) as claimed in claim 1 wherein p is 0 or 1 or a pharmaceutically acceptable salt thereof.

5. A compound of formula (I) as claimed in claim 1 wherein:

$R^2$ is selected from hydroxy, amino, azido, $C_{1-6}$alkyl, N—($C_{1-6}$alkyl)carbamoyl, N,N—($C_{1-6}$alkyl)$_2$carbamoyl, carbocyclyl-$R^{34}$—, —$NHR^9$ or —O—$R^{12}$;

$R^9$ and $R^{12}$ are independently selected from $C_{1-6}$alkanoyl or $C_{1-6}$alkylsulphonyl; wherein $R^9$ and $R^{12}$ may be independently optionally substituted on carbon by a group selected from $R^{20}$;

$R^{20}$ is hydroxy; and $R^{34}$ is —N($R^{29}$)C(O)—; wherein $R^{29}$ is hydrogen;

or a pharmaceutically acceptable salt thereof.

6. A compound of formula (I) as claimed in claim 1 wherein $R^3$ is halo or a pharmaceutically acceptable salt thereof.

7. A compound of formula (I) as claimed in claim 1 wherein n is 0 or 1 or a pharmaceutically acceptable salt thereof.

8. A compound of formula (I) as claimed in claim 1 wherein:
$R^4$ is $C_{1-6}$alkyl or carbocyclyl; wherein $R^4$ may be optionally substituted on carbon by one or more $R^{14}$; wherein $R^{14}$ is carbocyclyl;
or a pharmaceutically acceptable salt thereof.

9. A compound of formula (I) as claimed in claim 1 wherein:
$R^5$ and $R^6$ are independently selected from hydrogen or $C_{1-6}$alkyl; wherein $R^5$ and $R^6$ independently of each other may be optionally substituted on carbon by one or more $R^{16}$; wherein
$R^{16}$ is selected from methoxy;
or a pharmaceutically acceptable salt thereof.

10. A compound of formula (I), as claimed in claim 1, wherein:
Ring A, $R^2$ and q together form piperazin-1-yl, morpholino, 4-mesylpiperazin-1-yl, 4-acetylpiperazin-1-yl, 4-(2-acetoxyacetyl)piperazin-1-yl, 4-(2-hydroxyacetyl)piperazin-1-yl, 4-(2-chloroacetyl)piperazin-1-yl, 4-(2-methoxyacetyl)piperazin-1-yl, (3-methoxypropanoyl)piperazin-1-yl, (3-hydroxy-3-methylbutanoyl)piperazin-1-yl, (3-hydroxy-2,2-dimethylpropanoyl)piperazin-1-yl, ((R)-3-methyl-2-hydroxybutanoyl)piperazin-1-yl, ((S)-3-methyl-2-hydroxybutanoyl)piperazin-1-yl, 4-(2-dimethylaminoacetyl)piperazin-1-yl, 4-[2-(dimethylamino)ethylsulphonyl]piperazin-1-yl, 4-[2-(methoxy)ethylsulphonyl]piperazin-1-yl, 4-[2-(hydroxy)ethylsulphonyl]piperazin-1-yl, 4-(cyclopropylcarbonyl)piperazin-1-yl, 4-(1-hydroxycyclopropylcarbonyl)piperazin-1-yl, 4-(1-cyanocyclopropylcarbonyl)piperazin-1-yl, 4-(2-hydroxy-2-methylpropanoyl)piperazin-1-yl, 4-((R)-2-hydroxypropanoyl)piperazin-1-yl, 4-((S)-2-hydroxypropanoyl)piperazin-1-yl, 4-((R)-2-methoxypropanoyl)piperazin-1-yl, 4-((S)-2-methoxypropanoyl)piperazin-1-yl, 4-((R)-tetrahydrofuran-2-ylcarbonyl)piperazin-1-yl, 4-((S)-tetrahydrofuran-2-ylcarbonyl)piperazin-1-yl, 4-(isobutyryl)piperazin-1-yl, 4-((R)-2-hydroxybutanoyl)piperazin-1-yl, 4-((S)-2-hydroxybutanoyl)piperazin-1-yl, (R)-3-acetylaminopyrrolidin-1-yl, (S)-3-acetylaminopyrrolidin-1-yl, (R)-2-(cyclopropylaminocarbonyl)pyrrolidin-1-yl, (R)-2-(N-methylcarbamoyl)pyrrolidin-1-yl, (S)-2-(N,N-dimethylcarbamoyl)pyrrolidin-1-yl, 4-(ethenylsulphonyl)piperazin-1-yl, 4-[2-(2-propyn-1-yloxy)acetyl]piperazin-1-yl, 4-(tetrahydrofuran-3-ylcarbonyl)piperazin-1-yl, 4-(3-dimethylaminopropanoyl)piperazin-1-yl, 4-[2-(N-methyl-N-hydroxymethylamino)acetyl]piperazin-1-yl, 4-[3-hydroxy-2-(hydroxymethyl)propanoyl]piperazin-1-yl, 4-[2-(1,2,3,4-tetrazol-1-yl)acetyl]piperazin-1-yl, 4-[2-(1,2,3,4-tetrazol-5-yl)acetyl]piperazin-1-yl, 4-(1-methyl-L-prolyl)piperazin-1-yl, 4-[2-(mesyl)acetyl]piperazin-1-yl, 4-(2,2-difluoroacetyl)piperazin-1-yl, 4-[2-(pyrrolidin-1-yl)acetyl]piperazin-1-yl, 4-[2-(morpholino)acetyl]piperazin-1-yl, 4-[2-(diethylamino)acetyl]piperazin-1-yl, 4-(propionyl)piperazin-1-yl, 4-(3-hydroxypropionyl)piperazin-1-yl, 4-[2-(azetidin-1-yl)acetyl]piperazin-1-yl, (R)-3-aminopyrrolidin-1-yl, (S)-3-aminopyrrolidin-1-yl, (3R,5S)-4-acetyl-3,5-dimethylpiperazin-1-yl, (2S,5R)-4-acetyl-2,5-dimethylpiperazin-1-yl, (2RS,6SR)-2,6-dimethylmorpholin-4-yl]phenyl, 3-hydroxyazetidin-1-yl, 3-acetylaminoazetidin-1-yl, 3-(2-hydroxyacetylamino)azetidin-1-yl, 3-mesylaminoazetidin-1-yl, 3-mesyloxyazetidin-1-yl, 3-azidoazetidin-1-yl, 3-aminoazetidin-1-yl, (3R)-3-{[(2S)-2-hydroxypropanoyl]amino}pyrrolidin-1-yl, (3S)-3-{[(2S)-2-hydroxypropanoyl]amino}pyrrolidin-1-yl, (3S)-3-(glycoloylamino)pyrrolidin-1-yl and (3R)-3-(glycoloylamino)pyrrolidin-1-yl;

$R^1$ is fluoro, chloro or methyl;

p is 0 or 1;

$R^2$ is selected from hydroxy, amino, azido, methyl, N-methylcarbamoyl, N,N-dimethylcarbamoyl, acetamido, {[(2S)-2-hydroxypropanoyl]amino}, glycoloylamino, mesylamino, 2-hydroxyacetamido, mesyloxy or N-cyclopropylcarbamoyl;

q is 0-2; wherein the values of $R^2$ maybe the same or different;

$R^3$ is 5-fluoro or 5-chloro;

n is 0 or 1;

$R^4$ is ethyl, isopropyl, isobutyl, cyclobutyl or cyclopropylmethyl; and $R^5$ and $R^6$ are independently selected from hydrogen, methyl, ethyl, methoxymethyl, propyl;

or a pharmaceutically acceptable salt thereof.

11. A compound of formula (I), as claimed in claim 1, selected from:

2-{4-[4-(2-hydroxyacetyl)piperazin-1-yl]anilino}-4-(1-isopropyl-2-methyl-1H-imidazol-5-yl)-5-fluoropyrimidine hydrochloride;

2-{4-[4-(2-hydroxyacetyl)piperazin-1-yl]anilino}-4-(1-isopropyl-2-methyl-1H-imidazol-5-yl)pyrimidine;

(2S)-1-[4-(4-{[5-fluoro-4-(1-isopropyl-2-methyl-1H-imidazol-5-yl)pyrimidin-2-yl]amino}phenyl)piperazin-1-yl]-1-oxopropan-2-ol;

2-[4-(morpholino)anilino]-4-(1-isopropyl-2-methyl-1H-imidazol-5-yl)-5-fluoropyrimidine;

2-{4-[4-(acetyl)piperazin-1-yl]anilino}-4-(1-isopropyl-2-methyl-1H-imidazol-5-yl)-5-fluoropyrimidine;

2-[4-(4-acetylpiperazin-1-yl)anilino]-4-(1-isopropyl-2-methyl-1H-imidazol-5-yl)pyrimidine;

5-fluoro-4-(1-isopropyl-2-methyl-1H-imidazol-5-yl)-N-{4-[4-(methoxyacetyl)piperazin-1-yl]phenyl}pyrimidin-2-amine;

N-[4-(4-acetylpiperazin-1-yl)-3-fluorophenyl]-5-fluoro-4-(1-isopropyl-2-methyl-1H-imidazol-5-yl)pyrimidin-2-amine;

N-[4-(4-acetylpiperazin-1-yl)-3-fluorophenyl]-4-(1-isopropyl-2-methyl-1H-imidazol-5-yl)pyrimidin-2-amine; and (2R)-1-[4-(4-{[5-fluoro-4-(1-isopropyl-2-methyl-1H-imidazol-5-yl)pyrimidin-2-yl]amino}phenyl)piperazin-1-yl]-1-oxopropan-2-ol;

or a pharmaceutically acceptable salt thereof.

12. A process for preparing a compound of formula (I), as claimed in claim 1, or a pharmaceutically acceptable salt thereof, which process:

Process a) reacting a pyrimidine of formula (II):

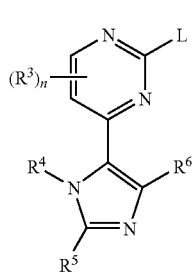
(II)

wherein L is a displaceable group; with an aniline of formula (III):

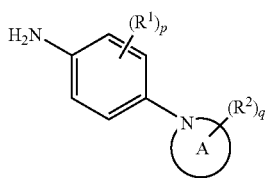
(III)

or

Process b) reacting a compound of formula (IV):

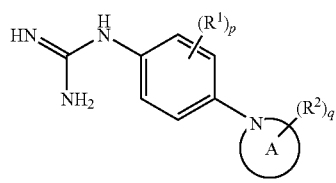
(IV)

with a compound of formula (V):

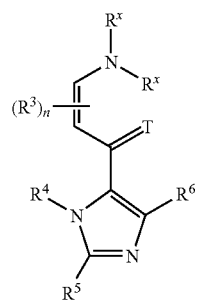
(V)

wherein T is O or S; $R^x$ may be the same or different and is selected from $C_{1-6}$alkyl; or Process c) reacting a pyrimidine of formula (VI):

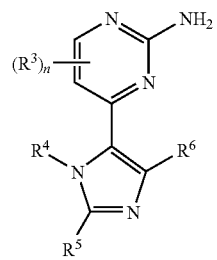
(VI)

wherein X is a displaceable group; with a heterocyclyl of formula (VII):

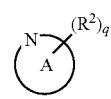
(VII)

or

Process d) for compounds of formula (I); reacting a pyrimidine of formula (VIII)

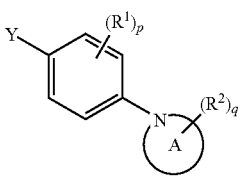
(VIII)

with a compound of formula (IX):

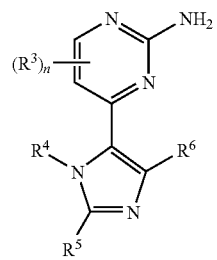
(IX)

where Y is a displaceable group;
and thereafter optionally:
i) converting a compound of the formula (I) into another compound of the formula (I);
ii) removing any protecting groups; and/or
iii) forming a pharmaceutically acceptable salt.

13. A pharmaceutical composition which comprises a compound of formula (I) or a pharmaceutically acceptable salt thereof, as claimed in claim 1, in association with a pharmaceutically-acceptable diluent or carrier.

14. A method of treating rheumatoid arthritis, in a warm-blooded animal, in need of such treatment which comprises administering to said animal an effective amount of a compound of formula (I) or a pharmaceutically acceptable salt thereof, as claimed in claim 1.

15. A method of treating rheumatoid arthritis in a warm-blooded animal, in need of such treatment which comprises administering to said animal an effective amount of a compound of formula (I) or a pharmaceutically acceptable salt thereof, as claimed in claim 1, wherein the animal is man.

* * * * *

UNITED STATES PATENT AND TRADEMARK OFFICE
CERTIFICATE OF CORRECTION

PATENT NO.        : 7,655,652 B2                                         Page 1 of 1
APPLICATION NO. : 10/586954
DATED             : February 2, 2010
INVENTOR(S)       : Andrews et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 630 days.

Signed and Sealed this

Twenty-third Day of November, 2010

David J. Kappos
*Director of the United States Patent and Trademark Office*